US007527957B2

(12) United States Patent
Sibbesen et al.

(10) Patent No.: US 7,527,957 B2
(45) Date of Patent: May 5, 2009

(54) METHODS OF ALTERING THE SENSITIVITY OF A XYLANASE TO A XYLANASE INHIBITOR

(75) Inventors: Ole Sibbesen, Bagsvaerd (DK); Jens Frisbaek Sørensen, Aarbus (DK)

(73) Assignee: Danisco A/S, Copenhagen (DK)

( * ) Notice: Subject to any disclaimer, the term of this patent is extended or adjusted under 35 U.S.C. 154(b) by 142 days.

(21) Appl. No.: 11/170,653

(22) Filed: Jun. 28, 2005

(65) Prior Publication Data

US 2005/0271769 A1 Dec. 8, 2005

Related U.S. Application Data

(60) Division of application No. 10/237,386, filed on Sep. 9, 2002, which is a continuation-in-part of application No. PCT/IB01/00426, filed on Mar. 8, 2001.

(30) Foreign Application Priority Data

| Mar. 8, 2000 | (GB) | ................................ | 0005585.5 |
| Jun. 27, 2000 | (GB) | ................................ | 0015751.1 |

(51) Int. Cl.
| C12N 9/24 | (2006.01) |
| C12N 15/00 | (2006.01) |
| C12N 5/04 | (2006.01) |
| C12P 19/04 | (2006.01) |
| C12P 21/06 | (2006.01) |
| C07H 21/04 | (2006.01) |

(52) U.S. Cl. .................... 435/200; 435/101; 435/320.1; 435/419; 435/69.1; 536/23.2

(58) Field of Classification Search ........................ None
See application file for complete search history.

(56) References Cited

U.S. PATENT DOCUMENTS

| 5,306,633 | A | * | 4/1994 | Gottschalk et al. | ........... | 435/200 |
| 5,736,384 | A |   | 4/1998 | Fukunaga et al. | | |
| 5,759,840 | A |   | 6/1998 | Sung et al. | | |
| 5,866,408 | A | * | 2/1999 | Sung et al. | ................... | 435/278 |
| 6,682,923 | B1 |  | 1/2004 | Bentzien et al. | | |

FOREIGN PATENT DOCUMENTS

| AU | 200016766 | 12/1999 |
| AU | 5132700 | 11/2000 |
| EP | 0 585 617 | 10/1997 |
| EP | 0585617 | 10/1997 |
| EP | 0 979 830 | 2/2000 |
| EP | 0979830 | 2/2000 |
| NL | 0979830 A1 * | 8/1998 |
| WO | WO 91/19782 | 12/1991 |
| WO | WO 00/39289 | 7/2000 |

OTHER PUBLICATIONS

Simoinen et al., 2 nd European Symposium on Enzymes in Grain Processing, 8-1- Dec. 1999, pp. 55-61, Helsinki, Finland. (In IDS).*
W.R. McLauchlan et al., "Xylanase Inhibitors From Cereals: Implications for Baking, Brewing and Plant Technology", STN International, Accession No. 2001:287270, 2000, pp. 55-61.
W. R. McLauchlan et al., "A Novel Class of Protein From Wheat Which Inhibits Xylanases[1]", Biochem J., vol. 338, 1999, pp. 441-446.
A. Sapag et al., "The Endoxylanases From Family 11: Computer Analysis of Protein Sequences Reveals Important Structural and Phylogenetic Relationships", Journal of Biotechnology, vol. 95, 2002, pp. 109-131.
F.D.L. Esteves et al., "Acidophilic Adaptation of Family 11 endo-β-1, 4-Xylanases: Modeling and Mutational Analysis", Protein Science, vol. 13, 2004, pp. 1209-1218.
P.R. Kumar et al., The Tertiary Structure of 1.59 Å Resolution and the Proposed Amino Acid Sequence of a Family-11 Xylanase From the Thermophilic Fungus *Paecilomyces varioti* Bainier, J. Mol. Biol., vol. 295, 2000, pp. 581-593.
McLaughlin et al., "Xylanase Inhibitors from Cereals: Implications for Baking, Brewing and Plant Technology," In 2nd *European Symposium on Enzymes In Grain Processing*, Eds.: Simoinen, T. and Tenkanen, M., VTT Symposium 207, Finland, 2000, pp. 55-61, Accession No. 2001:287270.
McLauchlan et al., A Novel Class of Protein from Wheat Which Inhibits Xylanases, Biochem J. (1999) 338, 441-446.
McLauchlan et al., Xylanase Inhibitors form Cereals: Implications for Baking, Brewing and Plant Technology, VTT Symposium (2002), 207, 55-61.
Anneli Törrönen et al., "The Two Major Xylanases From *Trichoderma reesei*: Characterization of Both Enzymes and Genes", Biotechnology, 1992, vol. 10, pp. 1461-1465.
Ute Krengel et al., "Three-dimensional Structure of Endo-1,4-β-xylanase 1 from *Aspergillus niger*: Molecular Basis for its Low pH Optimum", J. Mol. Biol., 1996, vol. 263, pp. 70-78.
Kiyoshi Ito et al., "Cloning and Sequencing of the *xynC* Gene Encoding Acid Xylanase of *Aspergillus kawachii*", Biosci. Biotech. Biochem., 1992, vol. 56, No. 8, pp. 1338-1340.
Accession No. Q9UUQ2: Kimura et al. "Purification, characterization, and molecular cloning of acidophilic xylanase from penicillium sp.40". Biosci. Blotechnol. Biochem. 2000. 64(6): 1230-1237.
Accession No. BAA19744: Kimura et al. "Cloning and sequence of xylanase G1 gene from Aspergillus oryzae KBN616". Unpublished; Direct submission on Apr. 11, 1997.
Accession No. D63381: Iefuji et al. "Acis xylanase from yeast Cryptococcus sp. S-2: purification, characterization, cloning and sequencing." Biosci. Biotechnol. Biochem. 1996 60(8): 1331-1338.
Ngo et al. The Protein Folding Problem and Tertiary Structure Prediction, Merz et al. (ed), Berkhauser, Boston, MA, p. 433, 492-495.

* cited by examiner

*Primary Examiner*—Richard Hutson
*Assistant Examiner*—Ganapathirama Raghu
(74) *Attorney, Agent, or Firm*—Frommer Lawrence & Haug LLP; Thomas J. Kowalski

(57) ABSTRACT

The present invention relates to a variant xylanase polypeptide, or fragment thereof having xylanse activity, comprising one or more amino acid modifications such that the polypeptide or fragment thereof has an altered sensitivity to a xylanase inhibitor as compared with parent enzyme.

22 Claims, 5 Drawing Sheets

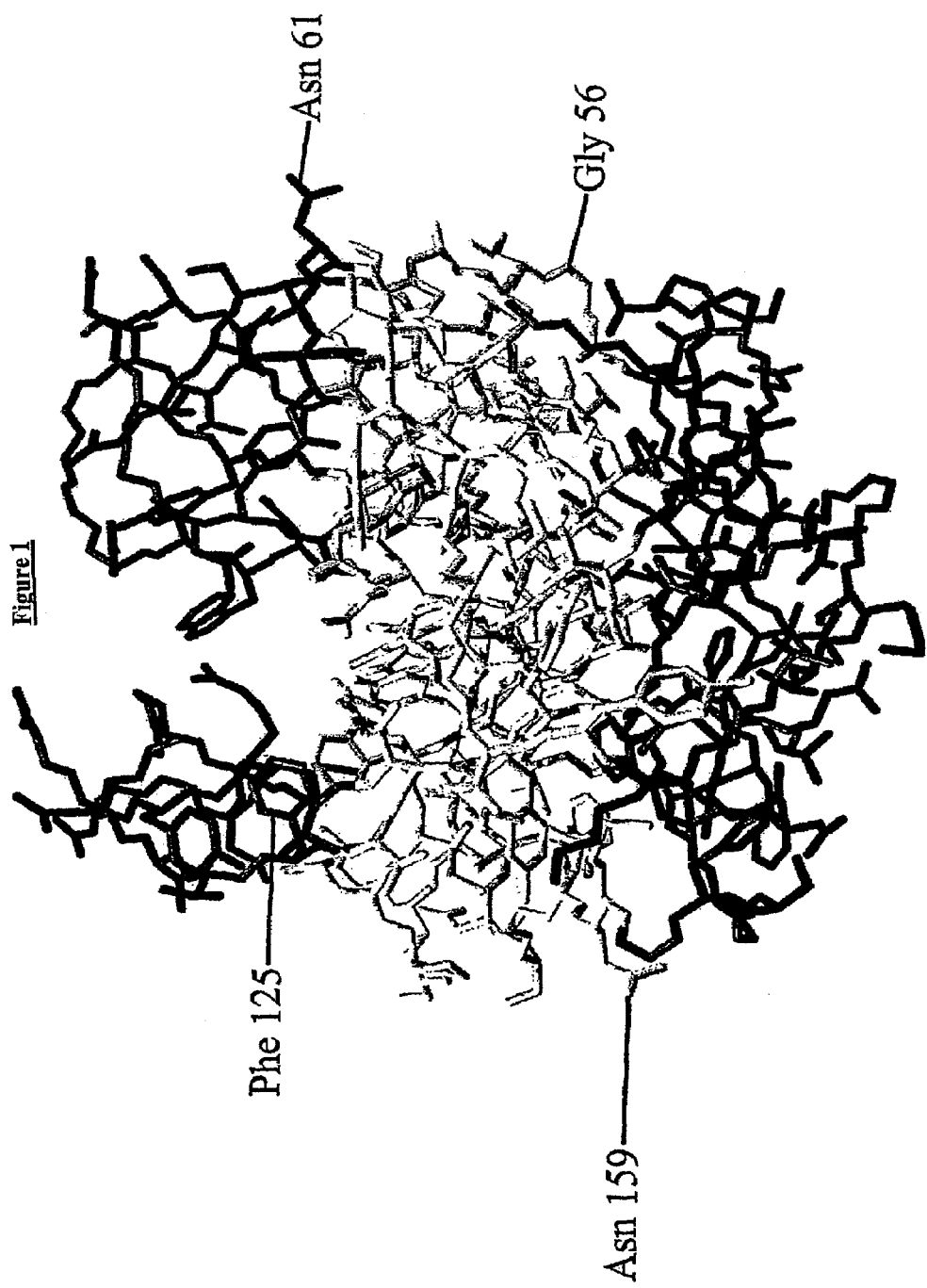

```
                                   91        105 106       120 121       135 136           150 151            165 166            180
B. subtilis xylA                   WQNWTDGGGIVNAVN GSGGNYSVNWS--NT GNFVVGKGWTTG--- -SPFRTINYNAGVW APNGNG--YLTLYGW TRS-PLIEYYVVDSW     113
B. circulans xylA                  WQNWTDGGGIVNAVN GSGGNYSVNWS--NT GNFVVGKGWTTG--- -SPFRTINYNAGVW APNGNG--YLTLYGW TRS-PLIEYYVVDSW     113
B. stearothermophilus xylA         WQYWTDGGGMVNAVN GPGGNYSVTWQ--NT GNFVVGKGWTVG--- -SNRVINYNAGIW EPSGNG--YLTLYGW TRN-ALIEYYVVDSW      111
A. caviae xylA                     WQNWTDGGGTVNAVN GSGGNYSVSWQ--NT GNFVVGKGWTYG--- -TNRVVNYNAGVF APSGNG--YLTFYGW TRN-ALIEYYVVDSW      112
C. carbonum xyl1                   WSWWSDGGARATYTN GAGGSYSVSWG--SG GNLVGGKGWNP--- -GTARTITYSGTY NYNGNS--YLAVYGW TRN-PLVEYYVVENF     122
H. turcicum xyl1                   WSWWSDGGARATYTN GAGGSYSVSWG--TG GNLVGGKGWNP--- -GTARTITYSGTY NPNGNS--YLAIYGW TRN-PLIEYYVVENF    128
A. pisi xyl                        YSWWTDGGAQATYTN GAGGSYSVNWK--TG GNLVGGKGWNP--- -GAARTITYSGTY SPSGNS--YLAVYGW TRN-PLIEYYVVENF      128
S. commune xylA                    YSWWTDGAGDATYQN NGGGSYTLTWSG-NN GNLVGGKGWNP--- -GAASRSISYSGTY QPNGNS--YLSVYGW TRS-SLIEYIVESY       96
T. lanuginosus xylA                YSWWSDGGAQATYTN LEGGTYEISWG--DG GNLVGGKGWNP--- -GLNARAIHFEGVY QPNGNS--YLAVYGW TRN-PLIEYIVENF     124
C. carbonum xyl2                   YSWWTDGGGSAQYTM GEGGSRYSVTWR--NT GNFVGGKGWNP--- -GSGRVINYGGAF NPQGNG--YLAVYGW TRN-PLVEYYVIESY    132
C. sativus xyl2                    YSWWTDGGGSAQYTM GEGSRYSVTWR---NT GNFVGGKGWNP--- -GTGRVINYGGAF NPQGNG--YLAVYGW TRN-PLVEYYVIESY    132
H. insolens xyl1                   YSWWSDGGGQQYTN LEGSRYQVRNR--NT GNFVGGKGWNP--- -GTGRINYNFSGSY NPQGNG--YLAVYGW TRN-PLVEYYVIESY    128
M. grisea xyl22                    YSWWTDGASPVQYQN GNGGSYSVQWQ--SG GNFVGGKGWMP--- -GGSKSITYSGTF NPVNMGNAYICIYGW TQN-PLVEYYILENY    133
C. gracile cgxA                    YSFWTDGGGTVNYQN GAGGSYSVQWQ--NC GNFVGGKGWNP--- -GAARTINFSGTF SPQGNG--YLAIYGW TQN-PLVEYYIVESF    122
T. reesei xyl2(2)                  HSYWNDGHSGVTYTN GPGGQFSVNWS--NS GNFVGGKGWQP--- -GTKNKVINFSGSY NPNGNS--YLSVYGW SRN-PLIEYYIVGNF    126
T. reesei, ALKO2721 Xyl2           YSYWNDGHGGVTYTN GPGGQFSVNWS--NS GNFVGGKGWQP--- -GTKNKVINFSGSY NPNGNS--YLSVYGW SRN-PLIEYYIVENF    126
T. reesei xyl1                     YSYWNDGHGGVTYTN GPGGQFSVNWS--NS GNFVGGKGWQP--- -GTKNKVINFSGSY NPNGNS--YLSVYGW SRN-PLIEYYIVENF    126
T. reesei xyl1                     YSWWTDGASPVQYQN GNGGSYSVQWQ--SG GNFVGGKGWMP--- -GGSKSITYSGTF NPVNMGNAYICIYGW TQN-PLIEYYILENY    125
C. gracile cgxB                    YSYWNDGHSGVTYTN GGGGSFTVNWS--NS GNFVAGKGWQP--- -GTKNKVINFSGSY NPNGNS--YLSIYGW SRN-PLIEYYIVENF     93
T. harzianum xylD                  YSYWNDGHSGVTYTN GAGGSFSVNWA--NS GNFVGGKGWNM--- -GSSRVINFSGSY NPNGNS--YLSVYGW SKN-PLIEYYIVENF    128
T. viride xyl                      YSFWTDGQNVQYTN EAGGQYSVTWS--GN GNWVGGKGWNM--- -GS-ARTINYTANY NPNGNS--YLAVYGW TRN-PLIEYYIVENF     124
C. gracile cgxB                    YSFWTDGGDVTYTN GDAGAYTVEWE--NV GNFVGGKGWNP--- -GSAQDITYSGTF TPSGNG--YLSVYGW TTD-PLIEYYIVESY     142
A. niger xyl2                      YSFWTNGGTVQYTN GAAGFYSVTWE--NC GDFTSGKGWST--- -GSARDITFEGTF NPSGNA--YLSVYGW TTS-PLVEYYILEDY     132
Penicillium sp 40 xylA             YSFWTDGGGSVSMNL NGGGSYSTQWT--NC GNFVAGKGWGN--- -GRRRTVRYSGYF NPSGNG--YGCLYGW TSN-PLVEYYIVDNW    133
Streptomyces sp xyl                YSFWTDGGGSVSMNL ASGGSYGTSWT--NC GNFVAGKGWAN--- -GARRTVNYSGSF NPSGNA--YLTLYGW TAN-PLVEYYIVDNW    133
Streptomyces sp xyl1               YSFWTDAPGTVTMNT GAGGNYSTQWS--NT GNFVAGKGWAT--- -GRRRTVNYSGTF NPSGNA--YLALYGW SQN-PLVEYYIVDNW    136
S. thermocyaneoviolaceus xylB      YSFWTDAQGTVSMDL GSGGTYSTQWR--NT GNFVAGKGWST--- -GRRKTVNYSGTF NPSGNA--YLTLYGW TTG-PLIEYYIVDNW    134
S. viridosporus T7A svxA           YSFWTDAPGTVSMEL GPGGNYSTWR---NT GNFVAGKGWAT--- -GRRRTVTYSASF NPSGNA--YLTLYGW TRN-PLVEYYIVESW    135
T. fusca xyl                       YSFWTDAPGTVSMNL GSGGNYSTSWS--NT GNFVAGKGWST--- -GSARTISYSGTF NPSGNA--YLAVYGW SHD-PLVEYYIVDSW    135
C. pachnodae xyl11A                YSFWTDNGGDVEYTN GNGGQYSVKWT--NC DNFVAGKGWST--- -GSAKTVTYSGEW ESNSNS--YVSLYGW TQN-PLVEYYIVDKY    124
A. oryzae XylG1                    SSYWADYG-NTRYSC GAGGHYDLSWG--NG GNVVAGRGWKP--- -ASPRAVTYSGSW QCNGNC--YLSVYGW TIN-PLVEYYIVENY    119
C. purpurea xyl                    YTFWKDSG-DASMGL QAGGRYTSQWSN-GT NNWVGGKGWNP--- -GG-PKVVTYSGSY NVDNSQNSYLALYGW TRS-PLIEYYVIESY    122
C. mixtus xyl                      YTFWKDSG-DASMTL LSGGRYQSSWGN-ST NNWVGGKGWNP--- -GNNSRVISYSGSY GVDSSQNSYLALYGW TRS-PLIEYYIVESY    123
P. fluorescens cellulosa xyl       YAFWKDSG-SAIFTL ESGGRYAGNWTT-ST NNWVGGKGWNP--- -GNSWRTVNYSGYY GINEYANSYLSLYGW TTN-PLIEYYIVESY    114
P. cochleariae xyl                 YVQNYNGNLGDFTYD ESAGTFSMYWEDGVS SDFVVGLGWTT--- -GS-SNAITYSAEY SASGSS-SYLAVYGW VNY-PQAEYIVEDY     85
A. kawachi xylC                    YVQNYNGNLGDFTYD ESAGTFSMYWEDGVS SDFVVGLGWTT--- -GS-SSTITYSAEY SASGSA-SYLAVYGW VNY-PQAEYIVEDY    113
A. niger xyl1                      YVQNYNGNLGAFSYN EGAGTFSMYWQQGVS NDFVVGLGRST--- -GS-SNPITYSASY SASGG--SYLAVYGW VNS-PQAEYVVEAY    112
A. tubigensis xyl1                 YVQNYNGNVANFEYS QYDGTFSVNWNG--N TDFVCGLGWTV--- -GT-GRIITYSGSY NPGYSG-SYQAIYGW TGQGSLSEYYVLDNY  108
P. purpurogenum xylB               YDQNYQT-GGQVSYS PSNTGFSVNWNT--Q GSFTGFSVNWNT--Q -GS-SAPINFGGSF SVNSGT-GLLSVYGW STN-PLVEYYIMEDN  108
Cryptococcus sp S-2 xyl-CS2        FELWKDYG-NTSMTL NNGGAFSASWNNIGN ALFRKGKKFDSTKTH HQ-LGNISINYNAAF NPGGNS--YLCVYGW TQS-PLAEYYIVESW   133
T. reesei xyl2                     YELWKDYG-NTSMTL NNGGAFSAGWNNIGN ALFRKGKKFDSTRTH HQ-LGNISINYNASF NPGGNS--YLCVYGW TQS-PLAEYYIVDSW   127
B. pumilus xylA(1)                 YELWKDYG-NTSMTL KNGGAFSCQWSNIGN ALFRKGFKFNDIQTY KQ-LGNISVNYDCNY QPYGNS--YLCVYGW TSS-PLVEYYIVDSW   159
B. pumilus xylA(2)                 FEYWKDTG-NGTMVL KDGGAFSCEWSNINN ILFRKGFKYDETKTH DQ-LGYITVTYSCNY QPNGNS--YLGVYGW TSN-PLVEYYIIESW   129
C. acetobutylicum XylB             YEFWKDSGGSGSMTL NSGGTFSAQWSNVNN IILFRKGKKFDEIQTH QQ-IGNMSINYGATY NPNGNS--YLTVYGW TVD-PLVEFYIVDSW   129
C. thermocellum XylB               YELWKDTG-TTSMLL LGGGKFSCSWSNINN CLFRIGKKWNCQYEW WE-LGTVLVNYDVDY YLCIYGW...              TRN-PLVEYYIVESW    127
Bacillus sp 41M-1 xylJ             -----------MTL LGGGKFSCNWSNIGN ALFRIGKKWDCTKTW QQ-LGTISVAYNVDY RPNGNS--YMCVYGW TRS-PLIEYYIVDSW    116
P. multivesiculatum xylA           YELWKOKG-DTEMTI NEGGTFSCKWSNINN ALFRKGKKFDCTKTY KE-LGNISVKYGVDY QPDGNS--YMCVYGW TID-PLVEYYIVESW    74
P. multivesiculatum xyl            YELWKDTG-NTTMTV DTGGRFSCQWSNINN ALFRTGKKFS--TAW NQ-LGTVKIITYSATY NPNGNS--YLCIYGW SRN-PLVEFYIVESW   154
R. albus xylA                      YELWKDTG-NTIMTV YTQGRFSCQWSNINN ALFRIGKKYN--QNW QS-LGTIRITYSATY NFNGNS--YLCIYGW STN-PLVEFYIVESW    112
Caldicellulosiruptor sp xylD       YEMWNNCNGQQASMN PGAGSFTCSWSNIEN FLARMGKNYDSQKKN YKAFGNIVLTYDVEY TPRGNS--YMCVYGW TRN-PLMEYYIVEGW    125
D. thermophilum xynB                                                                                                                129
R. flavefaciens xylA                                                                                                                
P. stipitis xylA                   YDRWTDLVGELEVRE LKHVWSHRTYSLCDL SCSTVLDSNS---- -------MFSLGKGWQAIS SROGVG----ATVVGW TRSPLLIEYYVVDSW   151
```

```
                      181       195 196         210 211         225 226         240 241       255 256         270
B. subtilis xylA      GTYRPTGTYKG---- TVKSDGGTYDIYTTT RYNAPSIDGDRTTFT QYWSVRQSKRPTG--- -------SNATITF SNHVNAWKSHGMNLG 189
B. circulans xylA     GTYRPTGTYKG---- TVKSDGGTYDIYTTT RYNAPSIDGDRTTFT QYWSVRQSKRPTG--- -------SNATITF TNHVNAWKSHGMNLG 189
B. stearothermophilus xylA GTYRATGNYESG--- TVNSDGGTYDIYTTM RYNAPSIDG-TQTFP QFWSVRQSKRPTG--- -------SNVSITF SNHVNAWRSKGMNLG 187
A. caviae xylA        GTYRPTGTYKG---- TVNSDGGTYDIYTTM RYNAPSIDG-TQTFP QYWSVRQSKRPTG--- -------VNSTITF SNHVNAWPSKGMYLG 187
C. carbonum xyl1      GTYDPSSQS--QNKG TVTSDGSSYKIAQST RTNQPSIDG-TRTFQ QYWSVRQNKRSSG--- -------SVNM KTHFDAWASKGMNLG 196
H. turcicum xyl1      GTYDPSSQA--QNKG TVTSDGSSYKIAQST RTNQPSIDG-TRTFQ QYWSVRQNKRSSG--- -------SVNM KTHFDAWASKGMNLG 202
A. pisi xyl           GTYDPSSQA--TYKG SVTADGSSYKIAQTQ RTNQPSIDG-TQTFQ QYWSVRQNKRSSG--- -------SVNM KTHFDAWAAKGMKLG 202
S. commune xylA       GSYDFSSAA--SHKG SVTCNGATYDILSTW RYNAPSIDG-TQTFE QFWSVRNPKKAPG-  S------ISGTVDV QCHFDAWKGLGMNLG 175
T. lanuginosus xylA   GTYDPSSGA--TDLG TVSECDGSIYRLGKTT RVNAPSIDG-TQTFD QYWSVRQDKRTSG-- -------TVQT GCHFDAWARAGLNVN 198
C. carbonum xyl2      GTYNPSSGA--QIKG SFQTDGGTYNVAVST RYNQPSIDG-TRTFQ QYWSVRTQKRVGG-- -------SVNM QNHFNAWSRYGLNLG 206
C. sativus xyl2       GTYNPSSGA--QVKG SFQTDGGTYNVAVST RYNQPSIDG-TRTFQ QYHSVRQQKRVGG-- -------SVNM QNHFNAWSRYGLNLG 206
H. inselens xyl1      GTYNPGSQA--QYKG TFYTDGDQYDFVSI RVNQPSIDG-TRTFQ QYWSIRKNKRVGG-- -------SVNM QNHFNAWQQCHGMPLG 202
M. grisea xyl22       GEYNPGNSA--QSRG TLQAAGTYTLHEST RVNQPSIEG-TRTFQ QYWAIRCQKRMSG-- -------TVNT GEFQAWERAGMRMG 207
C. gracile cgxA       GTYDPSSQA--SKFG TIQQDGSTYTIAKTT RVNQPSIEG-TSTFD OFWSVRQNHRSSG-- -------SVNV AAHFNAWAQAGLKLG 196
T. reesel xyl2(2)     GTYNPSTGA--TKLG EVTSDGSVYDIYRTQ RVNQPSIIG-TAFFY QYWSVRRNHRSSG--- -------SVNT ANHFNAWAQQGLTLG 200
T. reesel, ALKO2721 Xyl2 GTYNPSTGA--TKLG EVTSDGSVYDIYRTQ RVNQPSIIG-TAFFY QYWSVRRNHRSSG--- -------SVNT ANHFNAWAQQGLTLG 200
T. reesel xyl1        GTYNPSTGA--TKLJG EVTSDGSVYDIYRTQ RVNQPSIIG-TAFFY QYWSVRRNHRSSG--- -------SVNT ANHFNAWAQQGLTLG 199
T. harzianum xylD     GTYNPSTGT--TKLG EVTSDGSVYDIYRTO RVNQPSIIG-TAFFY QYWSVRRNHRSSG--- -------RSRL RTTSNAWRNLGLTLG 167
C. viride xyl         GTYNPSTGA--TRIG SVTTDGSCYDIYRTQ RVNQPSIEG-TSTFY QFWSVRQNKRSGG--- -------SVNM AAHFNAWAAAGLOLG 200
C. gracile cgxB       GDYNPGSGG--TYKG TVTSDGSVYDIYTAT RVNAASIQG-TATFT QYWSVRQNKRVG--- -------GTVTT SNHFNAWAKLGMNLG 197
A. niger xyl2         GDYNPGNSM--TYKG TVYSDGGTYDIYEHQ QVNAPSIQG-TATEN QYWSIRQNTRSS--- -------GTVTT ANHFNAWAKLGMNLG 202
Penicillium sp 40 xylA GSYRPTG---BYRG TVYSDGGTYKIYKTT RTNAPSVEG-TRTFD QYWSVRQSKVIGS-- -------GTITI GNHFDANARAGMNLG 198
Streptomyces sp xyl   GTYRPTG-----TYKG TVYSDGGTYDVYQTT RVNAPSVEG-TKTFN QYWSVRQSKRTG--- -------GSTTA GNHFDAWARYGMPLG 215
Streptomyces sp xyl1  GTYRPTG-----TYKG TVYSDGGTYDIYMTT RYNAPSIEG-TKIFD QYWSVRQNKRTG--- -------GTITT GNHFDAWAAHGMPLG 204
S. thermocyaneoviolaceus xylB GTYRPTG--KYKG TVTSDGGTYDIYKIT RVNAPSIEG-TKIFD QYFSVRNPKKGFG-- -------GTITT GNHFDAWANGMNLG 205
S. viridosporus T7A svxA GTYRPTG----TYMG TVTTDGGTYDIYKTT RYNAPSIEG-TRTFD QYWSVRQSKRTS--- -------GTITA GNHFDAWARHGMHLG 208
T. fusca xyl          GTYRPTG----TPMG TVNSDGGTYDIYKTT RTNEPSIIG-TSTFT QYFSVRESTRISG--- -------GTITA ANHFNAWASHGMNLG 206
A. pachnodae xyl1A    GDYDPSTGA--TELG TVESDGGTYKIYKTT RENAPSIEG-TATFT QYWSVRQSGRVG--- -------GVITT ANHFNAWAWASHGMNLG 207
A. oryzae XylG1       GNYNPSAGA--QRRG QVTADGSIYDIYIST CHNQPSILG-TNTFH QYWSIRRNKRVGG-- -------GTITA QNHFDAWANVGLQLG 198
C. purpurea xyl       GSNPASCSGGTDYG SFQSDGATYNVARCQ RVCQPSIDG-TQTFY QYFSVRSPKKGFG-- -------TVST GVHFNAWRSLGMPLG 193
C. mixtus xyl         GSYNPASCSGGTDYG SLYSDGSYQVCTBT QYNQPSIVG-TTTFP QYFSVRQNMKRSSG-- Q------ISGTITT ANHFNFWASKGLNLG 202
P. fluorescens cellulosa xyl GSYSPLNCPGGTDEG SFTSGATYQVRKCR RTNAPSIIG-TQSFD QYFSVRTPKKGFG-- N------ISGTITF ANHVNFWASKGLNLG 203
P. cochleariae xyl    GDYNPCSS--ATSLG TVYSDGSTYQVCTDT RTNEPSITG-TSTFT QYFSVRESTRISG--- Q------VSGSVNF ADHVQYWASKGLPLG 194
A. kawachi xylC       GDYNPCSS--ATSLG TVYSDGSTYQVCTDT RTNEPSITG--TSTFT QYFSVRESTRKTSG-- -------TVTV ANHFNFWAQHGFGNS 159
A. niger xyl1         GDYNPCSS--ATSLG TVYSDGSTYQVCTDT RINEPSITG-TSTFT QYFSVRESTRTSG--- -------TVTV ANHFNFWAQHGFGNS 187
A. tubigensis xyl1    GNYNPCSSGSATNLG TVSSDGGTYQVCTBT QYNQPSITG-TSTFT QFFSVRQGSRISG--- -------TVTI ANHFNFWANDGFGNS 186
P. purpurogenum xylB  GGYNPCTGSGTQLG SLYSDGSYQVCTBT QYNQPSIVG-TTTFP QYFSVRQNMKRSSG-- -------SVNM QNHFNYAQHGFPNR 184
Cryptococcus sp S-2 xyl-CS2 GSYSPLNCPGGTDEG SFTSGGATYQVRKCR RINAPSIIG-TQSFD QYISVRNSPRTSG--- -------TVTV QNHFNAWASLGLHLG 205
T. reesel xyl2        -HNYPAQG---TVKG TVTSDGAITYTWENT RVNEPSIGQ-TAFEN QYISVRQTKRTS--- -------GTASV SEHFKKWESLGMPMG 199
B. pumilus xyla(1)    GTYRPTG----TYKG SFYADGGTYDIYETT RVNQPSIIG-DAFFK QYWSVRQTKRTS--- -------GTVSV SAHFRKWSLGMPMG 199
B. pumilus xyla(2)    GTYRPTG----ATKG TVYSDGGTYDIYETT RVNQPSIIG-TAFFQ QYWSVRQNKRSSG-- -------GTVSV SAHFRKWSLGMPMG 199
C. acetobutylicum XylB GSWRPPG---TSKG TITVDGGTYDIYETT RINQPSIQG-NTTFK QYWSVRTSKRTS--- -------GTISV SKHFAAWESKGMPLG 232
C. thermocellum XylB  GTWRPPGA---TPKG TITVDGGTYEIYETT RVNQPSIKG-TAFFQ QYWSVRTSKRTS--- -------GTISV TEHFKAWERLGMKMC 202
Bacillus sp 41M-1 xylJ GSWRPPG----TSKG TITVDGGTYDIYETT RINQPSIKG-NTTFK QYWSVRTSKRTS--- -------GTSV SEHFRAWESLGWNMG 200
P. multivesiculatum xylA GSWRPPGA---TPKG TIIVDGGTYDIYVTD RYEOPSIDG-TKTFD QYWSVRDQKPTGDGT -------GTSV NHHFYNNWQEMGLKVG 189
P. multivesiculatum xyl GSWRPPGSN-S-MG TINVDGGTYDIYVTD RINQPSIDC-TTTFK QFWSVRTQKKT---- -------SGVISV SKHFBAWTSKGLNLG 147
R. albus xylA         GSWRPGAA--ESLG TVTVDGGTYDIYKTT RYEOPSIDC-TKTFD QYWSVRQDKPTGDGT K------IEGTISI SKHFDAWEQVGLTIG 234
Caldicellulosiruptor sp xylD GNWRPPG-A-TSLG QVTIDGGTYDIYRTT RVNQPSIVG-TATFD QYWSVRTSKRTS--- -------RCTVHV TDHFKAWAAKGLNLG 185
D. thermophilum xynB  GDWRPPGND-GEVKG TVSANGNYDIRRTM RYNQPSIDG-TATFP QYWSVRQTSGSANNQ TN-----YMKGTDV TKHFDAWSAAGLDMS 198
R. flavefaciens xylA  GSYHPSNIT--GTFV TVKCDGGTYDIYTNV RVNAPSIEG-TTFT QYWSVRQSATIQLAV IKPLTLQMAITITF SNHFDAWKTMTLEAT 238
```

Figure 2D

```
                                         271        285 286        300 301        315 316        330 331        345 346        360
B. subtilis xylA                         SNWAYQVMATEGYQS SGGSSNVTVW----- --------------- --------------- --------------- ---  213
B. circulans xylA                        SNWAYQVMATEGYQS SGGSNVTVW------ --------------- --------------- --------------- ---  213
B. stearothermophilus xylA               SSWAYQVLATEGYQS SGRSNVTVW------ --------------- --------------- --------------- ---  211
A. caviae xylA                           NSWSYQVMATEGYQS SGNANVTVW------ --------------- --------------- --------------- ---  211
C. carbonum xyl1                         -QHYYQIVATEGYFS TGNAQITVNCP---- --------------- --------------- --------------- ---  221
H. turcicum xyl1                         -SHYYQIVATEGYFS SGSASITVNCP---- --------------- --------------- --------------- ---  227
A. pisi xyl                              -THNYQIVATEGYFS SGSAQITVNCA---- --------------- --------------- --------------- ---  227
S. commune xylA                          SEHNYQIVATEGYQS SGTATITVTAS---- --------------- --------------- --------------- ---  201
T. lanuginosus xylA                      GDHYYQIVATEGYFS SGYARITVADVG--- --------------- --------------- --------------- ---  225
C. carbonum xyl2                         -QHYYQIVATEGYQS SGSSDIYVQTQ---- --------------- --------------- --------------- ---  231
C. sativus xyl2                          -QHYYQIVATEGYQS SGSSDIYVQTQ---- --------------- --------------- --------------- ---  231
H. insolens xyl1                         -QHYYQVVATEGYQS SGESDIYVQTH---- --------------- --------------- --------------- ---  227
M. grisea xyl22                          -NHNYMIVATEGYRS AGNSNINVQTPA--- --------------- --------------- --------------- ---  233
C. gracile cgxA                          -SHNYQIVAVEGYFS SGSSSITVS------ --------------- --------------- --------------- ---  219
T. reesei xyl2(2)                        -TMDYQIVAVEGYFS SGSASITVS------ --------------- --------------- --------------- ---  223
T. reesei, ALKO2721 Xyl2                 -TMDYQIVAVEGYFS SGSASITVS------ --------------- --------------- --------------- ---  223
T. reesei xyl1                           -TMDYQIVAVEGYFS SGSASITVS------ --------------- --------------- --------------- ---  222
T. harzianum xylD                        -TMDYQIVAVEGYFS SGSASITVS------ --------------- --------------- --------------- ---  190
T. viride xyl                            -TLDYQIIAVEGYFS SGNANINVS------ --------------- --------------- --------------- ---  223
C. gracile cgxB                          -THDYQIVATEGYYS SGSATVNVGASSDGS TGGGSTGGGSTNVSF --------------- --------------- ---  241
A. niger xyl2                            THN-YQIVATEGYQS SGSSSITVQ------ --------------- --------------- --------------- ---  225
Penicillium sp 40 xylA                   SFN-YQIVSTEGYES SGSSTITVS------ --------------- --------------- --------------- ---  221
Streptomyces sp xyl                      QFQYYMIMATEGYQS SGSSNITVSG----- --------------- --------------- --------------- ---  240
Streptomyces sp xyl1                     SFNYYMIMATEGYQS SGSSSISVS------ --------------- --------------- --------------- ---  228
S. thermocyaneoviolaceus xylB            TFN-YMILATEGYQS SGSSNITVGDSGGDN GGGGG---------- --------------- --------------- ---  292
S. viridosporus T7A svxA                 NHN-YMIMATEGYQS SGSSTITVSESGSGG GGGGG---------- --------------- --------------- ---  286
T. fusca xyl                             THD-YMIMATEGYQS SGSSNVTLGTSGGGN PGGGN---------- --------------- --------------- ---  295
C. pachnodae xyl11A                      RHD-YQILATEGYQS SGSSNIITGSTSGGG GSGGG---------- --------------- --------------- ---  293
A. oryzae XylG1                          THN-YMILATEGYKS SGSATITVE------ --------------- --------------- --------------- ---  221
C. purpurea xyl1                         -TYDYMIVATEGFRS SGSASITVS------ --------------- --------------- --------------- ---  216
C. mixtus xyl                            -NEDYMVLATEGYQS RGSSDITVSEGTGT  TSSSV---------- --------------- --------------- ---  290
P. fluorescens cellulosa xyl             -NHNYQVLATEGYQS SGSSDITVSEGTSGG GTSSV---------- --------------- --------------- ---  292
P. cochleariae xyl                       -THAHQIFATEGYQS SGFADITVS------ --------------- --------------- --------------- ---  217
A. kawachi xylC                          DFN-YQVMAVEAWSG AGSASVTIS------ --------------- --------------- --------------- ---  182
A. niger xyl1                            DFN-YQVMAVEAWSG AGSASVTISS----- --------------- --------------- --------------- ---  211
A. tubigensis xyl1                       DFN-YQVVAVEAWSG TGTASVTVSA----- --------------- --------------- --------------- ---  210
P. purpurogenum xylB                     NFN-YQVLAVEAWSG SGNANMKLISG---- --------------- --------------- --------------- ---  208
Cryptococcus sp S-2 xyl-CS2              NFN-YQVLAVEGFSG SGNANVYGSNTLTIGG APS------------ --------------- --------------- ---  209
T. reesei xyl2                           QMN-YQVVAVEGWGG SGSASQSVSN----- --------------- --------------- --------------- ---  229
B. pumilus xylA(1)                       -KMYETALTVEGYRS NGSANVMTNQLMTR- --------------- --------------- --------------- ---  227
B. pumilus xylA(2)                       -KMYETAFTVEGYQS SGSANVMTNQLFIGN --------------- --------------- --------------- ---  228
C. acetobutylicum XylB                   -KMHETAFNIEGYQS SGKADVNSMSINIGK --------------- --------------- --------------- ---  261
C. thermocellum XylB                     -KMYEALVVEGYQS  SGKADVTSMTITVGN --------------- --------------- --------------- ---  277
Bacillus sp 41M-1 xylJ                   -NMYEVALITVEGYQS SGSANVYGSNTLTIGG Q-------------- --------------- --------------- ---  268
P. multivesiculatum xylA                 -KVYEASLNIEGYQS AGSATVNKNEVVQT- --------------- --------------- --------------- ---  217
P. multivesiculatum xyl                  -LMYEASLITIEGYQS SGSATVNQNDVTGG- --------------- --------------- --------------- ---  175
R. albus xylA                            -NMYEVALNIEGYQS NGQATIYENELTVDG NY------------- --------------- --------------- ---  303
Caldicellulosiruptor sp xylD             -TIDQITLCVEGYQS SGSANITQNTFTIGG SSSGSSNGSNNG--- --------------- --------------- ---  274
D. thermophilum xynB                     -TIDQITLCVEGYQS SGSANITQNTFSQG- -----SSSGSS---- --------------- --------------- ---  273
R. flavefaciens xylA                     GTLYEVSLNIEGYRS NGSANVKSVSVTQGG SDNGGQQQNNDW--- --------------- --------------- ---  255
P. stipitis xylA                         HSTEGYFSSGITEQ  PHQPHRNTWATSLIS QTKHTARSLPIN--- --------------- --------------- ---  328
```

METHODS OF ALTERING THE SENSITIVITY OF A XYLANASE TO A XYLANASE INHIBITOR

REFERENCE TO RELATED APPLICATIONS

This application is a divisional of U.S. patent application Ser. No. 10/237,386 filed Sep. 9, 2002, which is a continuation-in-part of PCT/IB01/00426, filed Mar. 8, 2001, designating the U.S., published Sep. 13, 2001 as WO 01/66711 and claiming priority from GB 0005585.5 filed Mar. 8, 2000 and GB 0015751.1 filed Jun. 27, 2000, All of the above-mentioned applications, as well as all documents cited herein and documents referenced or cited in documents cited herein, are hereby incorporated by reference.

FIELD OF THE INVENTION

The present invention relates to mutant xylanase enzymes having an altered sensitivity to xylanase inhibitors. The present invention also relates to the use of these mutant enzymes in processing plant materials.

BACKGROUND TO THE INVENTION

For many years, endo-β-1,4-xylanases (EC 3.2.1.8) (referred to herein as xylanases) have been used for the modification of complex carbohydrates derived from plant cell wall material. It is well known in the art that the functionality of different xylanases (derived from different micro organisms or plants) differs enormously.

Comprehensive studies characterising the functionality of xylanases have been done on well characterised and pure substrates (Kormelink et al., 1992). These studies show that different xylanases have different specific requirements with respect to substitution of the xylose backbone of the arabinoxylan (AX). Some xylanases require three un-substituted xylose residues to hydrolyse the xylose backbone; others require only one or two. The reasons for these differences in specificity is thought to be due to the three dimensional structure within the catalytic domains, which in turn is dependent on the primary structure of the xylanase, i.e. the amino acid sequence. However, the translation of these differences in the amino acid sequences into differences in the functionality of the xylanases, has up until now not been documented when the xylanase acts in a complex environment, such as plant material.

The xylanase substrates found in wheat (wheat flour), have traditionally been divided into two fractions: The water unextractable AX (WU-AX) and the water extractable AX (WE-AX). The WU-AX:WE-AX ratio is approx. 70:30 in wheat flour. There have been numerous explanations as to why there are two different fractions of AX. The older literature (D'Appolonia and MacArthur (1976) and Montgomery and Smith (1955)) describes quite high differences in the substitution degree between WE-AX and WU-AX. The highest degree of substitution was found in WE-AX. This was used to explain why some of the AX was extractable. The high degree of substitution made the polymer soluble, compared to a lower substitution degree, which would cause hydrogen bonding between polymers and consequently precipitation.

The difference between the functionality of different xylanases has been thought to be due to differences in xylanase specificity and thereby their preference for the WU-AX or the WE-AX substrates.

In some applications (e.g. bakery) it is desirable to produce high molecular weight (HMW) soluble polymers from the WU-AX fraction. Such polymers have been correlated to a volume increase in bread making (Rouau, 1993; Rouau et al., 1994 and Courtin et al., 1999).

In other applications it is desirable to modify the HMW WU-AX, making the molecular weight lower, reducing their hydrocolloid effect and hence water-binding in the product (crackers, flour separation, etc.)

These different applications require different functionalities of the xylanases used to do the job. As mentioned above, the difference in functionality has been explained by the different substrate specificities of the xylanases.

SUMMARY OF THE INVENTION

By contrast to earlier studies, we have now shown that other factors are more important in determining xylanase functionality than the substrate specificity of the xylanases determined on pure well-characterised substrates. The data presented herein show that endogenous xylanase inhibitors dictate the functionality of the xylanases currently used in, for example, wheat flour systems. This means that a xylanase that normally modifies the WU-AX, giving increased dough liquid viscosity in a wheat flour system, has a different functionality if the endogenous xylanase inhibitor is absent in the wheat flour. Thus, our findings indicate that the design and application of uninhibited xylanases, for example, using site-directed mutagenesis could be a way to mimic the absence of xylanase inhibitors in various plant materials, giving new xylanases with completely new functionality. Such xylanases would be very effective in applications where a reduction in viscosity is required. The uninhibited xylanase would act rapidly on the AX, and be primarily influenced by its specific activity, rather than by endogenous inhibitors. From our studies, we consider that the inhibitory effects are likely to be far more important than the specific activity. Indeed our results show for the first time that there are 10 to 50 fold differences in inhibition levels between the family 11 xylanases.

Furthermore, we have gone on to design and test a series of xylanases modified by site-directed mutagenesis to demonstrate that xylanases can be produced that have reduced sensitivity to xylanase inhibitors present in plant materials. In particular, we have identified a number of residues in family 11 xylanases which influence the degree of inhibition of the xylanase.

Thus, it will be possible to produce variant xylanases having reduced sensitivity to xylanase inhibitors and hence altered functionality. This will, for example, allow a reduction in the amount of xylanase required in a number of applications such as animal feed, starch production, bakery, flour separation (wetmilling) and, paper and pulp production.

Accordingly, the present invention provides a variant xylanase polypeptide, or fragment thereof having xylanase activity, comprising one or more amino acid modifications such that the polypeptide or fragment thereof has an altered sensitivity to a xylanase inhibitor as compared with the parent enzyme.

Here, the "parent enzyme" is the xylanase enzyme from which the variant xylanase enzyme is derived or derivable. With respect to the term "derivable", the variant need not necessarily be derived from the parent enzyme. Instead, the variant could be prepared, for example, by use of recombinant DNA techniques that utilise nucleotide sequence(s) encoding said variant xylanase sequence—i.e. here the nucleotide sequence(s) are similar to mutated nucleotide sequence(s) but they are not prepared by mutation of the parent nucleotide sequence(s). The variant may even be prepared by chemically modifying a parent enzyme.

For some embodiments the parent enzyme is the wild type enzyme. The term "wild type" is a term of art understood by skilled persons and includes a phenotype that is characteristic of most of the members of a species occurring naturally and contrasting with the phenotype of a mutant. Thus, in the present context, the wild type enzyme may be a form of the enzyme naturally found in most members of the relevant species. Generally, the relevant wild type enzyme in relation to the variant polypeptides of the invention is the most closely related corresponding wild type enzyme in terms of sequence homology. For example, for the particular mutant xylanases described in the examples, the corresponding wild type enzyme is the wild type *B. subtilis* xylanase A, more specifically the wild type *B. subtilis* xylanase A published by Paice et al., 1986 and shown as SEQ I.D. 1. However, where a particular wild type sequence has been used as the basis for producing a variant polypeptide of the invention, this will be the corresponding wild type sequence regardless of the existence of another wild type sequence that is more closely related in terms of amino acid sequence homology.

For some embodiments, preferably the variant polypeptide is derived from a family 11 xylanase.

One of our surprising findings is that in our studies so far a mutation in the xylanase active site has no measurable effect on inhibition against the xylanase inhibitor. This is in direct contrast to the mutation(s) that are made outside of the active site—which mutations are discussed in more detail below.

In a preferred aspect the amino acid modification is of one or more surface amino acid residues.

In a more preferred aspect the amino acid modification is of one or more solvent accessible residues. Here, the solvent is water.

In a more preferred aspect the amino acid modification is of one or more surface residues outside of the active site.

In a highly preferred aspect the amino acid modification is of one or more surface residues outside of the active site and which is/are at least 8% solvent accessible. Here, the solvent is water.

In a highly preferred aspect the amino acid modification is of one or more surface residues outside of the active site and which is/are at least 10% solvent accessible. Here, the solvent is water.

Solvent accessibility can be determined using Swiss-Pdb-Viewer (version 3.5b1), which can be located via the internet at web pages maintained by Glaxo Wellcome Experimental Research.

The surface amino acids of xylanase enzymes are determinable by a person skilled in the art.

By way of example, the *B. subtilis* amino acid sequence for xylanase A is shown as SEQ I.D. No. 1. With respect to this sequence, the surface amino acid residues are:

Ala1-Trp6, Asn8, Thr10-Gly23, Asn25, Ser27, Asn29, Ser31-Asn32, Gly34, Thr43-Thr44, Ser46-Thr50, Asn52, Asn54, Gly56-Asn61, Asn63, Arg73-Leu76, Thr87-Arg89, Thr91-Lys95, Thr97, Lys99, Asp101-Gly102, Thr104, Thr109-Thr111, Tyr113-Asn114, Asp119-Thr124, Thr126, Gln133-Asn141, Thr143, Thr145, Thr147-Asn148, Asn151, Lys154-Gly157, Asn159-Leu160, Ser162-Trp164, Gln175, Ser177, Ser179, Asn181, Thr183, Trp185.

As indicated, the surface amino acids of other xylanase enzymes (such as *Thermomyces lanuginosus* xylanase A, whose coding nucleotide sequence is presented as SEQ ID No. 9) are determinable by a person skilled in the art.

Hence, for some aspects the present invention encompasses a variant xylanase polypeptide, or fragment thereof having xylanase activity, which variant xylanase polypeptide or fragment comprises one or more amino acid modifications at any one of amino acid residues:

Ala1-Trp6, Asn8, Thr10-Gly23, Asn25, Ser27, Asn29, Ser31-Asn32, Gly34, Thr43-Thr44, Ser46-Thr50, Asn52, Asn54, Gly56-Asn61, Asn63, Arg73-Leu76, Thr87-Arg89, Thr91-Lys95, Thr97, Lys99, Asp101-Gly102, Thr104, Thr109-Thr111, Tyr113-Asn114, Asp119-Thr124, Thr126, Gln133-Asn141, Thr143, Thr145, Thr147-Asn148, Asn151, Lys154-Gly157, Asn159-Leu160, Ser162-Trp164, Gln175, Ser177, Ser179, Asn181, Thr183, Trp185 of the *B. subtilis* amino acid sequence shown as SEQ I.D. No. 1 or its/their equivalent positions in other homologous xylanase polypeptides.

Thus, in one embodiment, the present invention provides a variant xylanase polypeptide, or fragment thereof having xylanase activity, comprising one or more amino acid modifications at any one of amino acid residues numbers:

11, 12, 13, 15, 17, 29, 31, 32, 34, 113, 114, 119, 120, 121, 122, 123, 124 and 175 of the *B. subtilis* amino acid sequence shown as SEQ I.D. No. 1 or their equivalent positions in other homologous xylanase polypeptides.

In one embodiment, the present invention provides a variant xylanase polypeptide or fragment thereof having xylanase activity, comprising one or more amino acid modifications at any one of amino acid residues numbers 11, 12 and 13 of the *B. subtilis* amino acid sequence shown as SEQ I.D. No. 1 or their equivalent positions in other homologous xylanase polypeptides.

Specific preferred examples of modifications made are presented in the Examples section herein.

For some embodiments, preferably the variant xylanase polypeptide, or fragment thereof having xylanase activity, comprises one or more amino acid modifications at any one of amino acid residues numbers: 8, 9, 10, 11, 12, 13, 14, 15, 16, 17, 18, 29, 30, 31, 32, 33, 34, 35, 36, 37, 61, 62, 63, 111, 112, 113, 114, 115, 116, 117, 118, 119, 120, 121, 122, 123, 124, 125, 173, 174, 175, 176, 177, 178 of the *B. subtilis* amino acid sequence shown as SEQ I.D. No. 1 or their equivalent positions in other homologous xylanase polypeptides.

For convenience, we sometimes refer to the amino acid residues numbers: 8, 9, 10, 11, 12, 13, 14, 15, 16, 17, 18, 29, 30, 31, 32, 33, 34, 35, 36, 37, 61, 62, 63, 111, 112, 113, 114, 115, 116, 117, 118, 119, 120, 121, 122, 123, 124, 125, 173, 174, 175, 176, 177, 178 as BAND 1.

FIG. 1 shows the 3-D structure of *B. subtilis* xylanase having the amino acid sequence shown as SEQ I.D. No. 1. BAND 1 is depicted in FIG. 1 as the upper layer of the molecule and extends approximately 13 Ångstroms from the top of the molecule when the molecule is orientated as shown in FIG. 1. BAND 1 ends with the residue Phe 125 on the left hand side when viewing FIG. 1 and with the residue Asn 61 on the right hand side when viewing FIG. 1.

In addition, or in the alternative, for some embodiments, preferably the variant xylanase polypeptide, or fragment thereof having xylanase activity, comprises one or more amino acid modifications at any one of the other amino acid residues.

Preferably said other modifications may occur at any one or more of amino acid residues numbers: 3, 4, 5, 6, 7, 19, 20, 21, 22, 23, 24, 25, 26, 27, 28, 38, 39, 40, 41, 42, 43, 44, 45, 55, 56, 57, 58, 59, 60, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 108, 109, 110, 126, 127, 128, 129, 130, 131, 158, 159, 160, 161, 162, 163, 164, 165, 166, 167, 168, 169, 170, 171, 172, 179, 180, 181, 182, 183 of the *B. subtilis* amino acid sequence shown as SEQ I.D. No. 1 or their equivalent positions in other homologous xylanase polypeptides.

For convenience, we sometimes refer to the amino acid residues numbers: 3, 4, 5, 6, 7, 19, 20, 21, 22, 23, 24, 25, 26, 27, 28, 38, 39, 40, 41, 42, 43, 44, 45, 55, 56, 57, 58, 59, 60, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 108, 109, 110, 126, 127, 128, 129, 130, 131, 158, 159, 160, 161, 162, 163, 164, 165, 166, 167, 168, 169, 170, 171, 172, 179, 180, 181, 182, 183 of the *B. subtilis* amino acid sequence shown as BAND 2.

Preferably said other modifications may occur at any one or more of the surface amino acid residues numbers: 3, 4, 5, 6, 19, 20, 21, 22, 23, 25, 27, 43, 44, 56, 57, 58, 59, 60, 73, 74, 75, 76, 87, 89, 91, 92, 93, 94, 109, 110, 126, 159, 160, 162, 163, 164, 179, 181, 183 of the *B. subtilis* amino acid sequence shown as SEQ I.D. No. 1 or their equivalent positions in other homologous xylanase polypeptides.

Preferably, the present invention encompasses a variant xylanase polypeptide, or fragment thereof having xylanase activity, which comprises one or more amino acid modifications in BAND 1 and optionally/or BAND 2 of the *B. subtilis* amino acid sequence or their equivalent positions (bands) in other homologous xylanase polypeptides. Hence, the modification is in at least BAND 1; but could be in just BAND 2 alone.

The variant xylanase polypeptide may comprise other modifications in other amino acid residues, such as modification at any one of amino acid residues: 1, 2, 46, 47, 48, 49, 50, 51, 52, 53, 54, 95, 96, 97, 98, 99, 100, 101, 102, 103, 104, 105, 106, 107, 132, 133, 134, 135, 136, 137, 138, 139, 140, 141, 142, 143, 144, 145, 146, 147, 148, 149, 150, 151, 152, 153, 154, 155, 156, 157, 184, 185 of the *B. subtilis* amino acid sequence shown as SEQ I.D. No. 1 or their equivalent positions in other homologous xylanase polypeptides.

The variant xylanase polypeptide may comprise other modifications in other surface amino acid residues, such as modification at any one of the surface amino acid residues: 1, 2, 46, 47, 48, 49, 50, 52, 54, 95, 97, 99, 101, 102, 104, 133, 134, 135, 136, 137, 138, 139, 140, 141, 143, 145, 147, 148, 151, 154, 155, 156, 157, 185 of the *B. subtilis* amino acid sequence shown as SEQ I.D. No. 1 or their equivalent positions in other homologous xylanase polypeptides.

Preferably, the inhibitor is an inhibitor found naturally in plant tissues. Preferably the sensitivity of the variant xylanase enzyme to the inhibitor is reduced as compared to the parent xylanase enzyme.

The present invention also provides a nucleic acid molecule (a nucleotide sequence) encoding a polypeptide of the invention. Also provided is a vector comprising a nucleic acid of the invention, optionally operably linked to a regulatory sequence capable of directing expression of said nucleic acid in a suitable host cell. A host cell comprising a nucleic acid or a vector of the invention is also provided.

In another aspect the present invention provides a method of making a polypeptide of the invention comprising transforming a host cell with a nucleic acid encoding said polypeptide, culturing the transformed cell and expressing said polypeptide.

Our results show that these variant polypeptides have improved properties that make them suitable for a variety of applications, such as bakery, animal feed, starch production, flour separation (wetmilling) and, paper and pulp production.

Accordingly, the present invention also provides the use of a variant polypeptide of the invention in a method of modifying plant materials.

Also provided is the use of a variant polypeptide of the invention in baking. The invention further provides the use of a variant polypeptide of the invention in processing cereals, starch production and animal feed and the use of a variant polypeptide of the invention in processing wood, for example in enhancing the bleaching of wood pulp.

In a further aspect, the present invention provides a method of altering the sensitivity of a xylanase polypeptide to an inhibitor which method comprises modifying one or more amino acid residues of said enzyme selected from amino acid numbers 11, 12, 13, 15, 17, 29, 31, 32, 34, 113, 114, 119, 120, 121, 122, 123, 124 and 175 based on the amino acid numbering of *B. subtilis* xylanase shown as SEQ ID No. 1, or the equivalent residues in other homologous xylanase polypeptides. Preferably the sensitivity is reduced.

Importantly, our results also show for the first time that xylanase inhibitors play an important role in determining the functionality of xylanase enzymes in a complex system, such as a plant material. By the term "functionality", we mean the biochemical properties of the xylanase in a given system. These properties include substrate specificity, $K_m$ and $V_{max}$ kinetic parameters (where appropriate) and the nature of the reaction products obtained by the action of the xylanase in that system. Functionality may also consequently be described in terms of the effect on the physical and/or chemical properties of the plant materials on which the xylanase acts, for example the extent to which the viscosity of the material is altered.

In the same way that variant xylanases may be used in a variety of processing applications, xylanase inhibitors may be used in a variety of processing applications such as bakery, wood pulp processing and cereal processing.

BRIEF DESCRIPTION OF THE DRAWINGS

The following Detailed Description, given by way of example, and not intended to limit the invention to specific embodiments described, may be understood in conjunction with the accompanying Figures, in which:

FIG. 1 shows the 3-D structure of *B. subtilis* xylanase having the amino acid sequence shown as SEQ I.D. No.1; and, FIG. 2 shows amino acid sequence alignment data in respect of 51 Family 11 xylanases (SEQ ID NOs: 16 to 66, from top to bottom).

DETAILED DESCRIPTION OF THE INVENTION

Although in general any molecular techniques mentioned herein are well known in the art, reference may be made in particular to Sambrook et al., Molecular Cloning, A Laboratory Manual (1989) and Ausubel et al., Short Protocols in Molecular Biology (1999) 4th Ed, John Wiley & Sons, Inc.

A. Variant Xylanase Polypeptides

Xylanase enzymes have been reported from nearly 100 different organisms, including plants, fungi and bacteria. The xylanase enzymes are classified into several of the more than 40 families of glycosyl hydrolase enzymes. The glycosyl hydrolase enzymes, which include xylanases, mannanases, amylases, β-glucanases, cellulases, and other carbohydrases, are classified based on such properties as the sequence of amino acids, the three dimensional structure and the geometry of the catalytic site (Gilkes, et al., 1991, Microbiol. Reviews 55: 303-315).

Of particular interest for baking applications are the enzymes classified in Family 11. All of these are xylanases and are known as the "Family 11 xylanases". Some publications refer to these synonymously as the Family G xylanases, but the term "Family 11 xylanases" will be used herein to refer to both Family G and Family 11 xylanases.

Table A lists a number of known Family 11 xylanases. Most of them have a molecular mass of about 21,000 Da. Three of the Family 11 xylanases (*Clostridium stercorarium* XynA, *Streptomyces lividans* XynB, and *Thermomonospora fusca* XynA) have a higher molecular mass of 31,000 to 50,000 Da. However, these xylanases have a catalytic core sequence of about 21,000 Da similar to the other Family 11 xylanases. The amino acid sequences of the Family 11 xylanases (or, for the larger enzymes, the catalytic core) show a high degree of similarity, usually with more than 40% identical amino acids in a proper amino acid alignment. The Family 11 xylanases, which are of bacterial, yeast, or fungal origin, share the same general molecular structure.

Figure 2A:
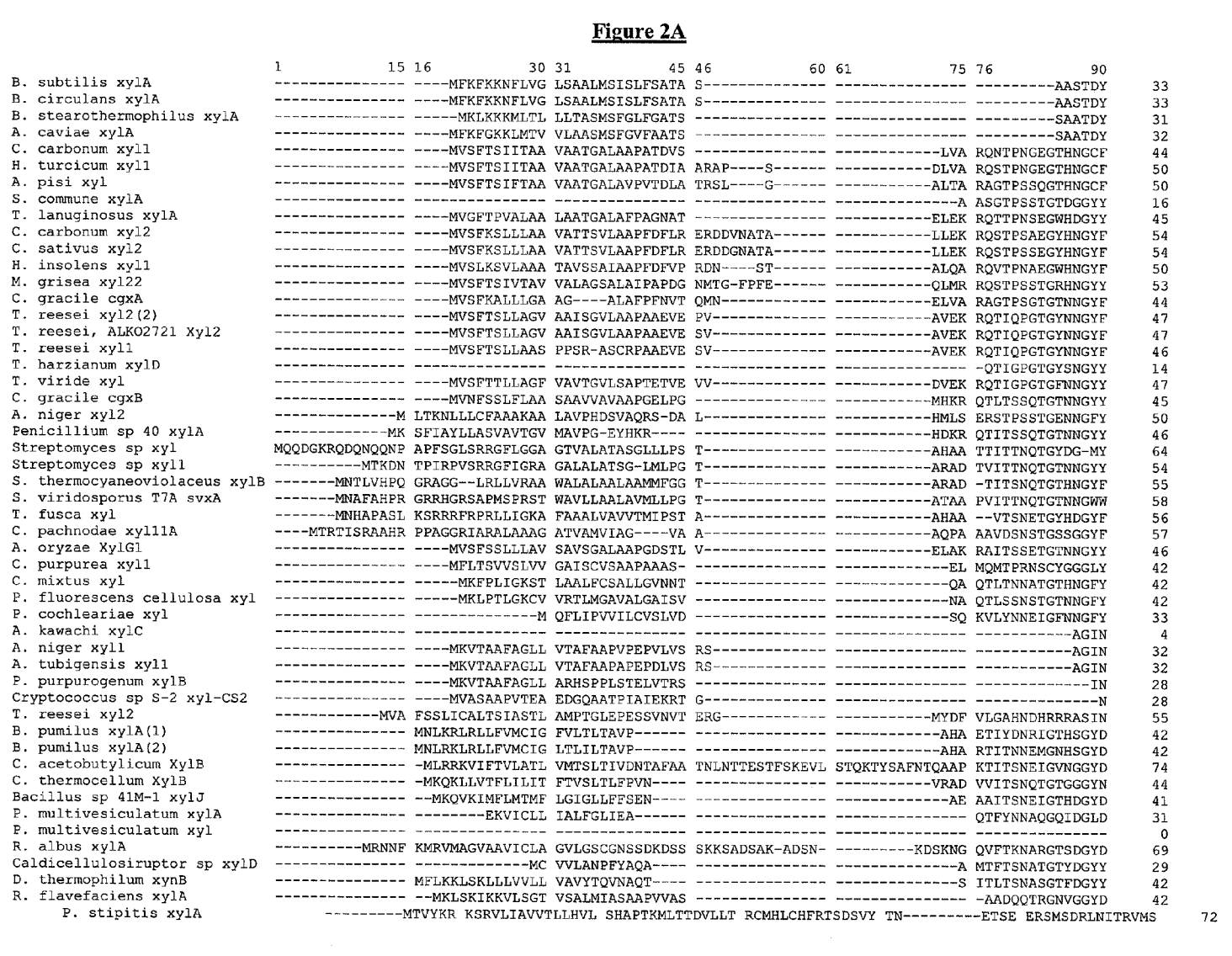

FIG. 2 shows amino acid sequence alignment data in respect of 51 Family 11 xylanases.

TABLE A

Family 11 xylanases

| | |
|---|---|
| *Aspergillus niger* Xyn A | *Aspergillus kawachii* Xyn C |
| *Aspergillus tubigensis* Xyn A | *Bacillus circulans* Xyn A |
| *Bacillus pumilus* Xyn A | *Bacillus subtilis* Xyn A |
| *Cellulomonas fimi* Xyn D | *Chainia* spp. Xyn |
| *Clostridium acetobutylicum* Xyn B | *Clostridium stercorarium* Xyn A |
| *Fibrobacter succinogenes* Xyn C | *Neocallimastix patriciarum* Xyn A |
| *Nocardiopsis dassonvillei* Xyn II | *Ruminococcus flavefaciens* Xyn A |
| *Schizophyllum commune* Xyn | *Streptomyces lividans* Xyn B |
| *Streptomyces lividans* Xyn C | *Streptomyces* sp. No. 36a Xyn |
| *Streptomyces thermoviolaceus* Xyn II | *Thermomonospora fusca* Xyn A |
| *Trichoderma harzianum* Xyn | *Trichoderma reesei* Xyn I |
| *Trichoderma reesei* Xyn II | *Trichoderma viride* Xyn |

Variant Xylanases of the Invention

A variant xylanase polypeptide of the invention is typically obtained by modifying a xylanase polypeptide by substituting, deleting or adding one or more amino acid residues within the amino acid sequence of the xylanase polypeptide. Preferably the modification comprises one or more amino acid substitutions. Modification of polypeptide sequences can be carried out using standard techniques such as site directed mutagenesis. The modification may also occur by chemical techniques—such as chemical modification of one or more amino acid residues.

The starting sequence may be a wild type sequence or a non-naturally occurring sequence, for example a derivative that has already been subjected to protein engineering. The xylanase sequence to be modified may be from any source, for example a bacterial, fungal or plant source. Preferably the xylanase sequence to be modified is that of a Family 11 xylanase, more preferably a Family 11 xylanase selected from *Trichoderma reesei* xylanase I, *Trichoderma reesei* xylanase II, *Trichoderma harzianum* xylanase, *Trichoderma viride* xylanase, *Bacillus circulans* xylanase A, *Bacillus subtilis* xylanase A, *Aspergillus niger* xylanase A, *Aspergillus kawachii* xylanase C, *Aspergillus tubigensis* xylanase A, *Streptomyces lividans* xylanase B, and *Streptomyces lividans* xylanase C.

In a particularly preferred embodiment, the xylanase sequence to be modified is the *B. subtilis* xylanase sequence shown as SEQ ID No. 1 or a homologue thereof. Preferably said homologue has at least 40, 50, 60 or 80% homology over at least 50 or 100 amino acid residues as determined using the GCG Wisconsin Bestfit package (University of Wisconsin, U.S.A.; Devereux et al., 1984, Nucleic Acids Research 12:387).

Specific modifications that are preferred according to the present invention include one or more amino acid substitutions at positions 11, 12, 13, 15, 17, 29, 31, 32, 34, 113, 114, 119, 120, 121, 122, 123, 124 and 175 based on the amino acid numbering of *B. subtilis* xylanase shown as SEQ ID No. 1, or the equivalent residues in other homologous xylanase polypeptides.

Particularly preferred substitutions include one or more of D11ΠY, D11ΠN, D11ΠF, D11ΠK, D11ΠS, D11ΠW, G12ΠF, G13ΠF, I15ΠK, N17ΠK, N17ΠY, N17ΠD, N29ΠK, N29ΠY, N29ΠD, S31ΠK, S31ΠY, S31ΠD, N32ΠK, G34ΠD, G34ΠF, G34ΠT, Y113ΠA, Y113ΠD, Y113ΠK, N114ΠA, N114ΠD, N114ΠF, N114ΠK, D119ΠK, D119ΠY, D119ΠN, G120ΠK, G120ΠD, G120ΠF, G120ΠY, G120ΠN, D121ΠN, D121ΠK, D121ΠF, D121ΠA, R122ΠD, R122ΠF, R122ΠA, T123ΠK, T123ΠY, T123ΠD, T124ΠK, T124ΠY, T124ΠD, Q175ΠE, Q175ΠS and Q175ΠL (with reference to the amino acid sequence of *B. subtilis* xylanase) or their equivalents in other homologous xylanase polypeptides. Further references to specific residues of the *B. subtilis* xylanase shown as SEQ ID No. 1 will also include their equivalents in other homologous xylanase polypeptides.

A combination of mutations may be carried out, for example mutations at two or more of the above-mentioned residues. Examples of such combinations are presented in the Examples section herein.

In a further embodiment, the variant polypeptides of the invention may be purified and isolated naturally occurring mutant xylanases. Alternatively, mutant xylanases may be generated by subjecting organisms to mutagens and then screening for individuals comprising mutations in their xylanase genes. Naturally occurring mutants and mutants generated by random mutagenesis may be identified/screened using a variety of techniques such as PCR screening using suitable nucleic acid primers to amplify regions of xylanase genes and sequencing the resulting fragments.

Thus variant polypeptides of the invention include naturally occurring mutant xylanases (purified and isolated from the organisms in which they occur or obtained recombinantly), mutant xylanases obtained by random mutagenesis and mutant xylanases obtained by site-directed mutagenesis.

Variant polypeptides of the invention may also be subjected to further modifications that do not necessarily affect sensitivity to inhibitors, including any substitution of, variation of, modification of, replacement of, deletion of or addition of one (or more) amino acids from or to the sequence providing the resultant amino acid sequence retains xylanase activity, preferably having at least substantially the same xylanase activity as the unmodified sequence.

Conservative substitutions may be made, for example according to the Table below. Amino acids in the same block in the second column and preferably in the same line in the third column may be substituted for each other:

| | | |
|---|---|---|
| ALIPHATIC | Non-polar | G, A, P |
| | | I, L, V |
| | Polar - uncharged | C, S, T, M |
| | | N, Q |
| | Polar - charged | D, E |
| | | K, R |
| AROMATIC | | H, F, W, Y |

Polypeptides of the invention also include fragments of the full length sequences mentioned above having xylanase activity.

Polypeptides of the invention may further comprise heterologous amino acid sequences, typically at the N-terminus or C-terminus, preferably the N-terminus. Heterologous sequence may include sequences that affect intra or extracellular protein targeting (such as leader sequences).

Polypeptides of the invention are typically made by recombinant means, for example as described below. However they may also be made by synthetic means using techniques well known to skilled persons such as solid phase synthesis. Polypeptides of the invention may also be produced as fusion proteins, for example to aid in extraction and purification. It may also be convenient to include a proteolytic cleavage site between the fusion protein partner and the protein sequence of interest to allow removal of fusion protein sequences, such as a thrombin cleavage site. Preferably the fusion protein will not hinder the function of the protein sequence of interest.

The use of appropriate host cells is expected to provide for such post-translational modifications as may be needed to confer optimal biological activity on recombinant expression products of the invention.

Polypeptides of the invention may be in a substantially isolated form. It will be understood that the protein may be mixed with carriers or diluents which will not interfere with the intended purpose of the protein and still be regarded as substantially isolated. A polypeptide of the invention may also be in a substantially purified form, in which case it will generally comprise the protein in a preparation in which more than 90%, e.g. 95%, 98% or 99% of the protein in the preparation is a polypeptide of the invention.

Variant polypeptides of the invention have altered sensitivity to xylanase inhibitors compared to the parent xylanase sequence—which may be a corresponding wild type xylanase. Preferably, variant polypeptides have reduced sensitivity to xylanase inhibitors. The term "altered sensitivity to xylanase inhibitors" means that extent to which the endo-β-1,4-xylanase activity of a variant polypeptide of the invention is inhibited by the xylanase inhibitor is different to that of the parent xylanase enzyme—which may be the corresponding wild type xylanase. Preferably the extent to which the variant polypeptide is inhibited by the inhibitor is less than that of the parent xylanase enzyme—which may be the wild type protein. This may, for example, be due to a change in the three-dimensional structure of the variant polypeptide such that the inhibitor no longer binds with the same affinity as it does to the parent xylanase enzyme—which may be the wild type enzyme.

The sensitivity of the variant polypeptides of the invention to xylanase inhibitors can be assayed using, for example, the assay described in example 4 and below. A suitable inhibitor for use in the assay is the inhibitor purified from wheat flour in example 1. Other inhibitors are described below.

Xylanase Assay (Endo-β-1,4-Xylanase Activity)

Xylanase samples are diluted in citric acid (0.1 M)—di-sodium-hydrogen phosphate (0.2 M) buffer, pH 5.0, to obtain approx. OD=0.7 in the final assay. Three dilutions of the sample and an internal standard with a defined activity are thermostated for 5 minutes at 40° C. At time=5 minutes, 1 Xylazyme tab (crosslinked, dyed xylan substrate) is added to the enzyme solution. At time=15 minutes (or in some cases longer, depending on the xylanase activity present in the sample) the reaction is terminated, by adding 10 ml of 2% TRIS. The reaction mixture is centrifuged and the OD of the supernatant is measured at 590 nm. Taking into account the dilutions and the amount of xylanase, the activity (TXU, Total-Xylanase-Units) of the sample can be calculated relative to the standard.

Xylanase Inhibitors

As used herein, the term "xylanase inhibitor" refers to a compound, typically a protein, whose role is to control the depolymerisation of complex carbohydrates, such as arabinoxylan, found in plant cell walls. These xylanase inhibitors are capable of reducing the activity of naturally occurring xylanase enzymes as well as those of fungal or bacterial origin. Although the presence of xylanase inhibitors have been reported in cereal seeds (see for example McLauchlan et al 1999a; Rouau and Suget 1998) their impact on the efficacy of xylanase enzymes has not been extensively examined.

McLauchlan et al (1999a) disclose the isolation and characterisation of a protein from wheat that binds to and inhibits two family-11 xylanases. Likewise, WO 98/49278 demonstrates the effect of a wheat flour extract on the activity of a group of microbial xylanases all of which are classified as family 11 xylanases. Debyser et al. (1999) also disclose that endoxylanases from *Aspergillus niger* and *Bacillus subtilis*, which are both members of the family 11 xylanases were inhibited by a wheat xylanase inhibitor called TAXI. McLauchlan et al (1999b) teach that extracts from commercial flours such as wheat, barley, rye and maize are capable of inhibiting both family 10 and 11 xylanases.

The xylanase inhibitor may be any suitable xylanase inhibitor. By way of example, the xylanase inhibitor may be the inhibitor described in WO-A-98/49278 and/or the xylanase inhibitor described by Rouau, X. and Surget, A. (1998), McLauchlan, R., et al. (1999) and/or the xylanase inhibitor described in UK patent application number 9828599.2 (filed Dec. 23, 1998), UK patent application number 9907805.7 (filed Apr. 6, 1999) and UK patent application number 9908645.6 (filed Apr. 15, 1999).

Xylanase Inhibitor Assay

100 μl of an candidate inhibitor fraction, 250 μl xylanase solution (containing 12 TXU microbial xylanase/ml) and 650 μl buffer (0.1 M citric acid-0.2M di-sodium hydrogen phosphate buffer, pH 5.0) are mixed. The mixture is thermostated for 5 minutes at 40.0° C. At time=5 minutes one Xylazyme tab is added. At time=15 minutes the reaction is terminated by adding 10 ml 2% TRIS. The reaction mixture is centrifuged (3500 g, 10 minutes, room temperature) and the supernatant is measured at 590 nm. The inhibition is calculated as residual activity compared to the blank. The blank is prepared the same way, except that the 100 μl inhibitor is substituted with 100 μl buffer (0.1 M citric acid—0.2 M di-sodium hydrogen phosphate buffer, pH 5.0).

Specific Xylanase Inhibitor

As indicated, a xylanase inhibitor that may be used in accordance with the present invention is the xylanase inhibitor described in UK patent application number 9828599.2 (filed Dec. 23, 1998), UK patent application number 9907805.7 (filed Apr. 6, 1999) and UK patent application number 9908645.6 (filed Apr. 15, 1999).

This endogenous endo-β-1,4-xylanase inhibitor is obtainable from wheat flour. The inhibitor is a di-peptide, having a MW of about 40 kDa (as measured by SDS-PAGE or mass spectrometry) and a pI of about 8 to about 9.5.

Sequence analysis to date has revealed the that the inhibitor has at least one or more of the sequences presented as SEQ ID No. 2, SEQ ID No. 3, SEQ ID No 4, SEQ ID No. 5, SEQ ID No. 6, SEQ ID No. 7 and/or SEQ ID No. 8.

These inhibitors described in the prior art may also be used in assays to determine the sensitivity of a variant polypeptide of the invention to xylanase inhibitors. They may also be used as described below to modulate the functionality of a xylanase.

Polynucleotides

Polynucleotides of the invention comprise nucleic acid sequences encoding the variant polypeptide sequences of the invention. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Polynucleotides of the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Nucleotide Vectors and Host Cells

Polynucleotides of the invention can be incorporated into a recombinant replicable vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells include bacteria such as *E. coli*, yeast and fungi.

Preferably, a polynucleotide of the invention in a vector is operably linked to a regulatory sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences. The term "regulatory sequences" includes promoters and enhancers and other expression regulation signals.

Enhanced expression of the polynucleotide encoding the polypeptide of the invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the invention.

Aside from the promoter native to the gene encoding the polypeptide of the invention, other promoters may be used to direct expression of the polypeptide of the invention. The promoter may be selected for its efficiency in directing the expression of the polypeptide of the invention in the desired expression host.

In another embodiment, a constitutive promoter may be selected to direct the expression of the desired polypeptide of the invention. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

Often, it is desirable for the polypeptide of the invention to be secreted from the expression host into the culture medium from where the polypeptide of the invention may be more easily recovered. According to the present invention, the polypeptide of the invention's native secretion leader sequence may be used to effect the secretion of the expressed polypeptide of the invention. However, an increase in the expression of the polypeptide of the invention sometimes results in the production of the protein in levels beyond that which the expression host is capable of processing and secreting, creating a bottleneck such that the protein product accumulates within the cell. Accordingly, the present invention also provides heterologous leader sequences to provide for the most efficient secretion of the polypeptide of the invention from the chosen expression host.

According to the present invention, the secretion leader may be selected on the basis of the desired expression host. A heterologous secretion leader may be chosen which is homologous to the other regulatory regions of the expression construct. For example, the leader of the highly secreted amyloglucosidase (AG) protein may be used in combination with the amyloglucosidase (AG) promoter itself, as well as in combination with other promoters. Hybrid signal sequences may also be used with the context of the present invention.

Examples of preferred heterologous secretion leader sequences are those originating from the fungal amyloglucosidase (AG) gene (glaA—both 18 and 24 amino acid versions e.g. from *Aspergillus*), the α-factor gene (yeasts e.g. *Saccharomyces* and *Kluyveromyces*) or the α-amylase gene (*Bacillus*).

Such vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides. Suitable host cells include, for example, fungal cells, such as *Aspergillus* and yeast cells, such as yeast cells of the genus *Kluyveromyces* or *Saccharomyces*. Other suitable host cells are discussed below.

The vectors may be for example, plasmid, virus or phage vectors provided with an origin of replication, optionally a promoter for the expression of the said polynucleotide and optionally a regulator of the promoter. The vectors may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in fungi), the ampicillin resistance gene (*E. coli*), the neomycin resistance gene (*Bacillus*) and the *E. coli* uidA gene, coding for β-glucuronidase (GUS). Vectors may be used in vitro, for example for the production of RNA or used to transfect or transform a host cell.

A further embodiment of the invention provides host cells transformed or transfected with a polynucleotide of the invention. Preferably said polynucleotide is carried in a vector for the replication and expression of said polynucleotides. The cells will be chosen to be compatible with the said vector and may for example be prokaryotic (for example bacterial), fungal, yeast or plant cells.

Bacteria from the genus *Bacillus* are very suitable as heterologous hosts because of their capability to secrete proteins into the culture medium. Other bacteria suitable as hosts are those from the genera *Streptomyces* and *Pseudomonas*.

Depending on the nature of the polynucleotide encoding the polypeptide of the invention, and/or the desirability for further processing of the expressed protein, eukaryotic hosts such as yeasts or fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a fungal host organism should be selected.

A heterologous host may also be chosen wherein the polypeptide of the invention is produced in a form which is substantially free from other xylanases. This may be achieved by choosing a host which does not normally produce such enzymes.

Examples of preferred expression hosts within the scope of the present invention are fungi such as *Aspergillus* species and *Trichoderma* species; bacteria such as *Bacillus* species, *Streptomyces* species and *Pseudomonas* species; and yeasts such as *Kluyveromyces* species and *Saccharomyces* species.

Particularly preferred expression hosts may be selected from *Aspergillus niger, Aspergillus niger* var. *tubigenis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

According to the present invention, the production of the polypeptide of the invention can be effected by the culturing of microbial expression hosts, which have been transformed with one or more polynucleotides of the present invention, in a conventional nutrient fermentation medium.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, an inducer may be added.

The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating microorganisms.

After fermentation, the cells can be removed from the fermentation broth by means of centrifugation or filtration. After removal of the cells, the variant polypeptide of the invention may then be recovered and, if desired, purified and isolated by conventional means.

Organisms

The term "organism" in relation to the present invention includes any organism that could comprise the nucleotide sequence coding for the variant xylanase protein according to the present invention and/or products obtained therefrom, wherein a transcriptional regulatory sequence can allow expression of the nucleotide sequence according to the present invention when present in the organism. Suitable organisms may include a prokaryote, fungus, yeast or a plant. For the xylanase aspect of the present invention, a preferable organism may be a bacterium, preferably of the genus *Bacillus*, more preferably *Bacillus subtilis*.

The term "transgenic organism" in relation to the present invention includes any organism that comprises the nucleotide sequence coding for the protein according to the present invention and/or products obtained therefrom, wherein the transcriptional regulatory sequence can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the desired compound which would be easily retrievable from, the cell or organism.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Short Protocols in Molecular Biology (1999), $4^{th}$ Ed., John Wiley & Sons, Inc.

If a prokaryotic host is used then the nucleotide sequence may need to be suitably modified before transformation—such as by removal of introns.

As mentioned above, a preferred host organism is of the genus *Bacillus*, such as *Bacillus subtilis*.

In another embodiment the transgenic organism can be a yeast. In this regard, yeasts have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae.*

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material.

A transgenic plant of the invention may be produced from any plant such as the seed-bearing plants (angiosperms), and conifers. Angiosperms include dicotyledons and monocotyledons. Examples of dicotyledonous plants include tobacco, (*Nicotiana plumbaginifolia* and *Nicotiana tabacum*), arabidopsis (*Arabidopsis thaliana*), *Brassica napus, Brassica nigra, Datura innoxia, Vicia narbonensis, Vicia faba*, pea (*Pisum sativum*), cauliflower, carnation and lentil (*Lens culinaris*). Examples of monocotyledonous plants include cereals such as wheat, barley, oats and maize.

Techniques for producing transgenic plants are well known in the art. Typically, either whole plants, cells or protoplasts may be transformed with a suitable nucleic acid construct encoding a zinc finger molecule or target DNA (see above for examples of nucleic acid constructs). There are many methods for introducing transforming DNA constructs into cells, but not all are suitable for delivering DNA to plant cells. Suitable methods include *Agrobacterium* infection (see, among others, Turpen et al., 1993, J. Virol. Methods, 42: 227-239) or direct delivery of DNA such as, for example, by PEG-mediated transformation, by electroporation or by acceleration of DNA coated particles. Acceleration methods are generally preferred and include, for example, microprojectile bombardment. A typical protocol for producing transgenic plants (in particular monocotyledons), taken from U.S. Pat. No. 5,874,265, is described below.

An example of a method for delivering transforming DNA segments to plant cells is microprojectile bombardment. In this method, non-biological particles may be coated with nucleic acids and delivered into cells by a propelling force. Exemplary particles include those comprised of tungsten, gold, platinum, and the like.

A particular advantage of microprojectile bombardment, in addition to it being an effective means of reproducibly stably transforming both dicotyledons and monocotyledons, is that neither the isolation of protoplasts nor the susceptibility to *Agrobacterium* infection is required. An illustrative embodiment of a method for delivering DNA into plant cells by acceleration is a Biolistics Particle Delivery System, which can be used to propel particles coated with DNA through a screen, such as a stainless steel or Nytex screen, onto a filter surface covered with plant cells cultured in suspension. The screen disperses the tungsten-DNA particles so that they are not delivered to the recipient cells in large aggregates. It is believed that without a screen intervening between the projectile apparatus and the cells to be bombarded, the projectiles aggregate and may be too large for attaining a high frequency of transformation. This may be due to damage inflicted on the recipient cells by projectiles that are too large.

For the bombardment, cells in suspension are preferably concentrated on filters. Filters containing the cells to be bombarded are positioned at an appropriate distance below the macroprojectile stopping plate. If desired, one or more screens are also positioned between the gun and the cells to be bombarded. Through the use of techniques set forth herein one may obtain up to 1000 or more clusters of cells transiently expressing a marker gene ("foci") on the bombarded filter. The number of cells in a focus which express the exogenous gene product 48 hours post-bombardment often range from 1 to 10 and average 2 to 3.

After effecting delivery of exogenous DNA to recipient cells by any of the methods discussed above, a preferred step is to identify the transformed cells for further culturing and plant regeneration. This step may include assaying cultures directly for a screenable trait or by exposing the bombarded cultures to a selective agent or agents.

An example of a screenable marker trait is the red pigment produced under the control of the R-locus in maize. This pigment may be detected by culturing cells on a solid support containing nutrient media capable of supporting growth at this stage, incubating the cells at, e.g., 18° C. and greater than 180 µE m$^{-2}$ s$^{-1}$, and selecting cells from colonies (visible aggregates of cells) that are pigmented. These cells may be cultured further, either in suspension or on solid media.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos selective system, bombarded cells on filters are resuspended in nonselective liquid medium, cultured (e.g. for one to two weeks) and transferred to filters overlaying solid medium containing from 1-3 mg/l bialaphos. While ranges of 1-3 mg/l will typically be preferred, it is proposed that ranges of 0.1-50 mg/l will find utility in the practice of the invention. The type of filter for use in bombardment is not believed to be particularly crucial, and can comprise any solid, porous, inert support.

Cells that survive the exposure to the selective agent may be cultured in media that supports regeneration of plants. Tissue is maintained on a basic media with hormones for about 2-4 weeks, then transferred to media with no hormones. After 2-4 weeks, shoot development will signal the time to transfer to another media.

Regeneration typically requires a progression of media whose composition has been modified to provide the appropriate nutrients and hormonal signals during sequential developmental stages from the transformed callus to the more mature plant. Developing plantlets are transferred to soil, and hardened, e.g., in an environmentally controlled chamber at about 85% relative humidity, 600 ppm $CO_2$, and 250 µE $m^{-2}$ $s^{-1}$ of light. Plants are preferably matured either in a growth chamber or greenhouse. Regeneration will typically take about 3-12 weeks. During regeneration, cells are grown on solid media in tissue culture vessels. An illustrative embodiment of such a vessel is a petri dish. Regenerating plants are preferably grown at about 19° C. to 28° C. After the regenerating plants have reached the stage of shoot and root development, they may be transferred to a greenhouse for further growth and testing.

Genomic DNA may be isolated from callus cell lines and plants to determine the presence of the exogenous gene through the use of techniques well known to those skilled in the art such as PCR and/or Southern blotting.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27).

Thus, in one aspect, the present invention relates to a vector system which carries a construct encoding a variant xylanase polypeptide according to the present invention and which is capable of introducing the construct into the genome of a plant.

The vector system may comprise one vector, but it can comprise at least two vectors. In the case of two vectors, the vector system is normally referred to as a binary vector system. Binary vector systems are described in further detail in Gynheung An et al. (1980), Binary Vectors, *Plant Molecular Biology Manual A*3, 1-19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* (An et al. (1986), *Plant Physiol.* 81, 301-305 and Butcher D. N. et al. (1980), *Tissue Culture Methods for Plant Pathologists*, eds.: D. S. Ingrams and J. P. Helgeson, 203-208).

Several different Ti and Ri plasmids have been constructed which are suitable for the construction of the plant or plant cell constructs described above.

B. Uses

In a general sense, a variant xylanase of the invention may be used to alter, for example reduce, the viscosity derived from the presence of hemicellulose or arabinoxylan in a solution or system comprising plant cell wall material. Typically said plant cell wall materials will comprise one or more xylanase inhibitors.

Specifically, a variant xylanase of the invention may be used in processing plant materials for use as foodstuffs, such as animal feed, in starch production, in baking and in the processing of wood pulp to make paper.

Preparation of Foodstuffs

A variant xylanase of the invention may be used to process plant materials such as cereals that are used in foodstuffs including animal feed. As used herein, the term "cereal" means any kind of grain used for food and/or any grass producing this grain such as but not limited to any one of wheat, milled wheat, barley, maize, sorghum, rye, oats, triticale and rice or combinations thereof. In one preferred embodiment, the cereal is a wheat cereal.

The xylan in the food and/or feed supplement is modified by contacting the xylan with the variant xylanase of the present invention.

As used herein, the term "contacting" includes but is not limited to spraying, coating, impregnating or layering the food and/or feed supplement with the variant xylanase enzyme of the present invention.

In one embodiment, the food and/or feed supplement of the present invention may be prepared by mixing the variant xylanase enzyme directly with a food and/or feed supplement. By way of example, the variant xylanase enzyme may be contacted (for example, by spraying) onto a cereal-based food and/or feed supplement such as milled wheat, maize or soya flour.

It is also possible to incorporating the variant xylanase enzyme it into a second (and different) food and/or feed or drinking water which is then added to the food and/or feed supplement of the present invention. Accordingly, it is not essential that the variant xylanase enzyme provided by the present invention is incorporated into the cereal-based food and/or feed supplement itself, although such incorporation forms a particularly preferred aspect of the present invention.

In one embodiment of the present invention, the food and/or feed supplement may be combined with other food and/or feed components to produce a cereal-based food and/or feed. Such other food and/or feed components may include one or more other (preferably thermostable) enzyme supplements, vitamin food and/or feed supplements, mineral food and/or feed supplements and amino acid food and/or feed supplements. The resulting (combined) food and/or feed supplement comprising possibly several different types of compounds can then be mixed in an appropriate amount with the other food and/or feed components such as cereal and protein supplements to form a human food and/or an animal feed.

In one preferred embodiment, the food and/or feed supplement of the present invention can be prepared by mixing different enzymes having the appropriate activities to produce an enzyme mix. By way of example, a cereal-based food and/or feed supplement formed from e.g. milled wheat or maize may be contacted (e.g. by spraying) either simultaneously or sequentially with the xylanase enzyme and other enzymes having appropriate activities. These enzymes may include but are not limited to any one or more of an amylase, a glucoamylase, a mannanase, an a galactosidase, a phytase, a lipase, a glucanase, an-arabinofuranosidase, a pectinase, a protease, a glucose oxidase, a hexose oxidase and a xylanase. Enzymes having the desired activities may for instance be mixed with the xylanase of the present invention either before contacting these enzymes with a cereal-based food and/or feed supplement or alternatively such enzymes may be contacted simultaneously or sequentially on such a cereal based supplement. The food and/or feed supplement is then in turn mixed with a cereal-based food and/or feed to prepare the final food and/or feed. It is also possible to formulate the food and/or feed supplement as a solution of the individual enzyme activities and then mix this solution with a food and/or feed material prior to processing the food and/or feed supplement into pellets or as a mash.

Bakery Products

The present invention provides the use of a variant xylanase polypeptide of the invention in a process for preparing a foodstuff. Typical bakery (baked) products in accordance with the present invention include bread—such as loaves, rolls, buns, pizza bases etc.—pretzels, tortillas, cakes, cookies, biscuits, crackers etc. The preparation of foodstuffs such as bakery products is well know in the art. Dough production, for example, is described in example 2. The use of variant xylanases of the invention to alter the viscosity of a flour slurry in described in the example 5.

Starch Production

A variant xylanase of the invention may also be used in starch production from plant materials derived from cereals and tubers, such as potatoes.

Processing of Wood Pulp

A variant xylanase of the invention may also be used in processing wood pulp, for example in the preparation of paper.

As discussed above, we have shown that a major determinant of xylanase functionality is the presence of endogenous inhibitors in plant material. Consequently, although one method for altering xylanase functionality is to modify a xylanase to change its sensitivity to endogenous inhibitors, another method would be to vary the amount and/or type of inhibitor present in the plant material. Thus, the present invention also provides the use of a xylanase inhibitor to alter the functionality of a xylanase and consequently the use of a xylanase inhibitor in the methods of processing plant materials described above.

The present invention will now be further described with reference to the following examples which are intended to be illustrative only and non-limiting.

EXAMPLES

Example 1

Purification and Characterisation of Wheat Endogenous Xylanase Inhibitor 2 kg wheat flour (Danish reform, batch 99056) was extracted with water, using a flour:water ratio of 1:2, during 10 minutes of stirring. The soluble endogenous xylanase inhibitor was separated from the flour-water slurry by centrifugation. The extraction and centrifugation was performed at 4° C. The inhibitor was purified from the water extract by the following chromatographic techniques and concentration techniques: HPLC-SEC, HPLC-CIEC, rotary evaporation, HPLC-HIC, HPLC-SEC and rotary evaporation. The xylanase inhibitor could be monitored and quantified during purification, using the following quantification method.

Inhibitor Quantification Method

1 XIU (Xylanase Inhibitor Unit) is defined as the amount of inhibitor that decreases 1 TXU to 0.5 TXU under the conditions described below.

The xylanase used in this assay is *Bacillus subtilis* wild type xylanase.

250 µl xylanase solution containing 12 TXU/ml, approx. 100 µl xylanase inhibitor solution and citric acid (0.1 M)-disodium-hydrogen phosphate (0.2 M) buffer, pH 5, to react a reaction volume of 1000 µl is pre-incubated for 5 minutes at 40° C. At t=5 minutes, 1 Xylazyme (Megazyme, Ireland) tablet is added to the reaction mixture. At t=15 minutes the reaction is terminated, by addition of 10 ml 2% TRIS/NaOH, pH 12. The solution is filtered and the absorbency of the supernatant is measured at 590 nm. By choosing several different concentrations of inhibitor in the above assay, it is possible to create a plot of OD versus inhibitor concentration. Using the slope (a) and intercept (b) from this plot and the concentration of the xylanase it is possible to calculate the amount of XIU in a given inhibitor solution (equation 1).

$$\text{amount of XIU in solution} = ((b/2)/-a)/\text{TXU} \quad \text{Equation 1}$$

From the endogenous xylanase inhibitor purification, the following inhibitor yield was recovered (table 1).

TABLE 1

Wheat endogenous xylanase inhibitor recovery after purification.

| Sample | Amount | XIU | XIU, total | Recovery, % |
|---|---|---|---|---|
| Flour | 2000 g | 590/g | 1.180.000 | 100 |
| Purified inhibitor | 90 ml | 4658/ml | 419.220 | 35.5 |

The inhibitor sample was pure and free from wheat endogenous xylanolytic activities.

Example 2

Fractionation and Reconstruction of Wheat Flour Free of Xylanase Inhibitor and Xylanases Functionality in This Flour as a Function of Added Xylanase Inhibitor Flour Fractionation and Reconstitution The flour used was: Danish Reform flour, batch No 99056. The fractionation, inhibitor inactivation and reconstitution were as follows:

A simple dough was made by mixing 1600 gram flour, with optimal water addition, according to a baker's absorption at 500 BU and mixing time according to Farinograph results. This resulted in 2512 gram dough. The gluten was manually washed out from the dough, using a water dough ratio of approx. 5:1. The water used was pre-chilled to 4° C. to prevent further enzyme activity in the dough. The resulting washwater contained the soluble proteins (including the xylanase inhibitor), lipids, non-starch polysaccharides and starch. The starch and other non-soluble components were separated from the wash-water by centrifugation (5000 g, 10 minutes, 10° C.). To inactivate the endogenous xylanase inhibitor in the wash-water, the supernatant from the centrifugation was boiled for three minutes using a heat-evaporator.

All three fractions (gluten, starch and solubles) were frozen in flasks and placed in a freeze dryer. After drying, the fractions were weighed, grounded using a mortar and pestle, coffee mill and sieved through a 250 µm sieve. All fractions were weighed again and flour was reconstituted, based on the ratios obtained after fractionation.

Enzymes

The xylanases listed in table 2 have been used in the study. The xylanases are purified, meaning no other xylonolytic activity is present in the sample.

TABLE 2

Xylanases used in the study and activity, TXU.

| ID | Origin | TXU |
|---|---|---|
| B. sub | B. subtilis. | 5100 |
| A. nig | A. niger | 8800 |

Xylanase Assay (Endo-$\beta$-1,4-Xylanase Activity)

Xylanase samples are diluted in citric acid (0.1 M)-disodium-hydrogen phosphate (0.2 M) buffer, pH 5.0, to obtain approx. OD=0.7 in the final assay. Three dilutions of the sample and an internal standard with a defined activity are thermostated for 5 minutes at 40° C. At time=5 minutes, 1 Xylazyme tab (crosslinked, dyed xylan substrate) is added to the enzyme solution. At time=15 minutes (or in some cases longer, depending on the xylanase activity present in the sample) the reaction is terminated, by adding 10 ml of 2% TRIS. The reaction mixture is centrifuged and the OD of the supernatant is measured at 590 μm. Taking into account the dilutions and the amount of xylanase, the activity (TXU, Total-Xylanase-Units) of the sample can be calculated relative to the standard.

Baking Trials

Baking trials were done with (1.44×initial inhibitor level in Danish Reform flour, batch No 99056) and without addition of purified endogenous xylanase inhibitor to the reconstituted flour, respectively. The baking trials were done using the xylanases listed in table 2 and the compositions listed in table 3.

TABLE 3

Composition of dough made within the baking trials.

| Dough No | ID | TXU | Inh. add, XIU/50 g |
|---|---|---|---|
| 1 | Control | 0 | 0 |
| 2 | B. sub | 7500 | 0 |
| 3 | A. nig | 7500 | 0 |
| 4 | B. sub | 7500 | 850 |
| 5 | A. nig | 7500 | 850 |
| 6 | Control | 0 | 850 |

Dough Analysis

The dough were analysed with respect to:

Stickiness

Dough stickiness was measured on a TX-XT2 system (Stable Micro Systems) using a SMS Dough Stickiness Cell according to the method described by Chen And Hoseney (Lebensmittel Wiss u.-Technol., 28, 467-473. 1995).

Viscosity Analysis of Dough Liquid

The viscosity of extracted dough liquid was measured using a Brookfield viscosimeter after extraction.

Pentosan Analysis of Dough Liquid

Solubilised pentosan was measured in the dough liquid using the method of Rouau and Surget (Carbohydrate polymers, 24, 123-132, 1994).

RESULTS

Flour Fractionation and Reconstitution

The fractionation and reconstitution of the dough resulted in 168.15 grams of freeze dried gluten, 111.13 grams of freeze dried soluble fraction and 1143.56 grams of freeze dried starch.

Inhibitor Quantification in Flour

Using the inhibitor quantification method, the inhibitor level in the 99056 flour and the reconstituted flour could be detected. The results from these analyses are listed in table 4.

TABLE 4

Results from inhibitor quantification in native flour (99056) and reconstituted flour.

| Flour | Inhibitor concentration, XIU/g flour |
|---|---|
| 99056 | 590 |
| Reconstituted flour | 42 |

Comparing the inhibitor level in the two portions of flour a 93% (100−(42XIU/590XIU)×100%)) decrease of inhibitor level in the reconstituted flour is shown.

Baking Trials

The results from the baking trial are listed in tables 5 and 6.

TABLE 5

Data from baking trials with reconstituted flour, xylanase and +/−xylanase inhibitor addition. Std. dev., % represents the standard deviation over two days of baking.

| ID | TXU | Inh., XIU/50 g | Avg. spec. vol, ml/gram | Std. dev., % |
|---|---|---|---|---|
| Control | 0 | 42 | 3.04 | 4.06 |
| B. sub | 7500 | 42 | 3.23 | 12.51 |
| A. nig. | 7500 | 42 | 3.44 | 5.24 |
| B. sub | 7500 | 850 | 3.22 | 4.26 |
| A. nig. | 7500 | 850 | 3.38 | 0.70 |
| Control | 0 | 850 | 2.94 | 0.05 |

The standard deviation shown in table 5 reflects the dough handling properties of the tested dough. The dough made without the endogenous xylanase inhibitor (42 XIU), were very difficult to handle. The standard deviation for these doughs are in the area of 3 to 12.5%. Compared to the dough with the inhibitor added, this is quite high. If these standard deviations are compared with the actual changes in the bread volume, it can be seen that the figures are approximately the same value. This means that we can not conclude anything about the absence of the inhibitor's influence on the bread volume. If we look at the dough made with addition of the endogenous xylanase inhibitor (850 XIU) in table 5, we can see that we were able to produce bread from the reconstituted flour in a reproducible way over a two day period. The standard deviation was within the area of 0.05 to 4.2%, which is acceptable. From table 6 it can be seen, that the xylanases all increased the volume of the baked bread.

TABLE 6

Volume increase in bread baked from reconstituted flour as a function of xylanase and xylanase inhibitor addition.

| ID | TXU | Inh., XIU/50 g | Avg. spec. vol, ml/gram | Volume increase as function of xylanase, % |
|---|---|---|---|---|
| Control | 0 | 42 | 3.04 | 0.0 |
| B. sub | 7500 | 42 | 3.23 | 6.2 |
| A. nig. | 7500 | 42 | 3.44 | 13.3 |
| B. sub | 7500 | 850 | 3.22 | 9.7 |
| A. nig. | 7500 | 850 | 3.38 | 15.0 |
| Control | 0 | 850 | 2.94 | 0.0 |

What can be deduced from table 5 and table 6, is that the absence of the xylanase inhibitor in the flour made the handling of the dough very difficult. Therefore, what may seem as a positive response in volume by addition of inhibitor in table 6, probably can be explained by the high standard deviation in the dough lacking the inhibitor, due to difficult handling properties. Furthermore, it can be concluded that all the xylanases tested increased the bread volume significantly compared to the blank control.

Stickiness

The same dough, that was used for the baking trials, was used for stickiness measurements. The results are listed in table 7.

TABLE 7

Data representing stickiness as a function of time, xylanase and xylanase inhibitor addition to reconstituted flour.

| ID | TXU | Inh., XIU/50 g | Avg. stickiness after 10 min, g × s | Avg. stickiness after 60 min, g × s |
|---|---|---|---|---|
| Control | 0 | 42 | 4.71 | 4.79 |
| B. sub. | 7500 | 42 | 12.20 | 13.39 |
| A. nig. | 7500 | 42 | 9.22 | 12.58 |
| B. sub. | 7500 | 850 | 2.51 | 3.66 |
| A. nig. | 7500 | 850 | 5.24 | 6.45 |
| Control | 0 | 850 | 4.10 | 4.15 |

The results in table 7 clearly indicate the influence of the inhibitor that was observed in the experiment. The dough with a low level of xylanase inhibitor in combination with xylanase, was very difficult to handle and mould. However, when the inhibitor was added, the dough became dry and very easy to handle. As can be seen from table 7, addition of the 990202 xylanase in combination with the inhibitor decreased the stickiness. The dough became drier.

Table 7 also shows that there is only a small effect of time on the stickiness. It seems that the xylanases act very rapidly. Within the first 10 minutes most of the arabinoxylan is modified when the first xylanase (B. sub) is added. The second xylanase tested (A. nig), seems to act less rapidly. A function of time can easily be observed using this xylanase. This is also the xylanase that shows the least effect as a function of inhibitor level when analysed on stickiness.

Dough Viscosity

The dough viscosity and the pentosan analysis results were obtained from the same extraction of dough prepared from reconstituted flour added xylanase and xylanase inhibitor. This dough was analysed after two proofing times, 30 and 120 minutes.

The results of the viscosity analysis are presented in table 8.

TABLE 8

Data representing dough liquid viscosity as a function of time, xylanase and xylanase inhibitor addition to reconstituted flour.

| ID | TXU | Inh., XIU/50 g | Avg. dough viscosity, cP, 30 min proofing | Avg. dough viscosity, cP, 120 min proofing |
|---|---|---|---|---|
| Control | 0 | 42 | 5.21 | 5.56 |
| B. sub. | 7500 | 42 | 5.07 | 4.55 |
| A. nig. | 7500 | 42 | 5.78 | 4.14 |
| B. sub. | 7500 | 850 | 9.03 | 11.09 |
| A. nig. | 7500 | 850 | 8.44 | 8.55 |
| Control | 0 | 850 | 5.96 | 6.95 |

As can be seen from table 8 the inhibitor has a significant effect on the functionality of the xylanases. Without addition of the inhibitor, the arabinoxylan is being de-polymerised to Low Molecular Weight (LMW) arabinoxylan with a low viscosity. Addition of inhibitor prevents this very extensive depolymerisation of the arabinoxylan.

Pentosan Analysis of Dough Liquid

The results from the pentosan (arabinoxylan) analysis of the dough liquid are presented in table 9.

TABLE 9

Data representing pentosan solubilisation as a function of time, xylanase and xylanase inhibitor addition to reconstituted flour.

| ID | TXU | Inh., XIU/50 g | Avg. Pentosan, %, 30 min proofing | Avg. Pentosan, %, 120 min proofing |
|---|---|---|---|---|
| Control | 0 | 42 | 0.387 | 0.458 |
| B. sub. | 7500 | 42 | 0.766 | 0.819 |
| A. nig. | 7500 | 42 | 0.719 | 0.798 |
| B. sub. | 7500 | 850 | 0.410 | 0.544 |
| A. nig. | 7500 | 850 | 0.560 | 0.673 |
| Control | 0 | 850 | 0.400 | 0.528 |

As can be seen from the results in table 9, the addition of endogenous xylanase inhibitor decreased the solubilisation of the arabinoxylan. When evaluated after 30 minutes proofing time, the amount of arabinoxylan solubilised in absence of the inhibitor is almost twice the amount as in presence of the inhibitor. Calculated on the basis of the relating control samples, the solubilisation is much higher in absence of the inhibitor, as illustrated in the following example:

$(0.766-0.387)/(0.410-0.400)=37.9$ times higher solubilisation

The above example was calculated on basis of solubilisation of arabinoxylan using the Bacillus xylanase, 30 minutes proofing and +/− inhibitor.

Example 3

Site-Directed Mutagenesis on Xylanases

Specific mutants of Bacillus subtilis xylanase may be obtained by site directed mutagenesis of the wild type enzyme, by the use of any of a number of commercially available mutagenesis kits. An example of how to obtain the D11F mutant using the Quick Exchange kit, available from Stratagene Cloning Systems, 11011 North Torrey Pines Road, La Jolla, Calif. 92037, USA is given below:

The DNA sequence encoding Bacillus subtilis xylanase A has been published by Paice et al., 1986.

The sequence of the coding region is as follows, with the sequence encoding the mature part of the protein shown in capitals: (SEQ ID NO: 10)

```
catatgtttaagtttaaaaagaatttcttagttggattatcggcagcttt aatgagtattagcttgttttcggcaaccgcctctgcaGCTAGCACAGACT

ACTGGCAAAATTGGACTGATGGGGGCGGTATAGTAAACGCTGTCAATGGG

TCTGGCGGGAATTACAGTGTTAATTGGTCTAATACCGGAAATTTTGTTGT

TGGTAAAGGTTGGACTACAGGTTCGCCATTTAGGACGATAAACTATAATG

CCGGAGTTTGGGCGCCGAATGGCAATGGATATTTAACTTTATATGGTTGG

ACGAGATCACCTCTCATAGAATATTATGTAGTGGATTCATGGGGTACTTA

TAGACCTACTGGAACGTATAAAGGTACTGTAAAAAGTGATGGGGGTACAT

ATGACATATATACAACTACACGTTATAACGCACCTTCCATTGATGGCGAT
```

-continued

CGCACTACTTTTACGCAGTACTGGAGTGTTCGCCAGTCGAAGAGACCAAC

CGGAAGCAACGCTACAATCACTTTCAGCAATCATGTGAACGCATGGAAGA

GCCATGGAATGAATCTGGGCAGTAATTGGGCTTACCAAGTCATGGCGACA

GAAGGATATCAAAGTAGTGGAAGTTCTAACGTAACAGTGTGGTAA

The part of the gene encoding the mature part of the wild type enzyme may be expressed intracellularly in *E. coli* by methods well known to people skilled in the art of molecular biology. For example:

1. Generating a copy of the capitalised part of the above described gene by use of the Polymerase Chain Reaction (PCR) with an added Nde1 restriction enzyme site (CATATG) before the GCTAGCACA and an added HindIII restriction site (AAGCTT) after the GTGTGGTAA.
2. Inserting the resultant modified copy of the gene by use of the above mentioned enzymes into the expression vector pET24a(+), which can be obtained from Novagen, Inc. 601 Science Drive, Madison, Wis. 53711, USA.
3. Transforming into a suitable *E. coli* strain and expression by fermentation as described by the vendor of pET24a(+).

Our D11F mutant enzyme may be obtained by using the "Quick Exchange" mutagenesis kit according to the manufacturer, and using the above described *Bacillus subtilis* wild type xylanase-pET24a(+) construct and the following PCR mutagenesis primers:

```
Sense primer: (SEQ ID NO: 12)
CTACTGGCAAAATTGGACTTTTGGAGGAGGTATAGTAAACGCTG

Antisense primer: (SEQ ID NO: 13)
CAGCGTTTACTATACCTCCTCCAAAAGTCCAATTTTGCCAGTAG
```

The mutant enzyme is expressed and purified using the same protocols as for the wild type enzyme.

Example 4

Inhibition Studies of Xylanase Mutants

Xylanase mutants expressed in *E. coli* (see Example 3) were fermented and purified (meaning no other xylanolytic activity was present in the purified preparation) using a desalting step and a cation exchange chromatography step.

These pure xylanase mutant preparations were diluted to 12 TXU/ml using 0.1 M citric acid-0.2 M di-sodium-hydrogen phosphate, pH 5.0 and used in the following assay.

A stable inhibitor preparation was made according to the protocol described in Example 1. This stable inhibitor preparation is used as stock for all xylanase-xylanase inhibitor studies. Using the inhibitor quantification method described in example 1, the inhibitor preparation was analysed to contain 126 XIU/ml.

Assay

To 250 µl diluted xylanase mutant preparations, are added 0, 10, 25, 50 or 100 µl inhibitor preparation, respectively. To these inhibitor-xylanase mixtures were added 0.1 M citric acid-0.2 M di-sodium-hydrogen phosphate, pH 5.0 making the end-volume 1000 µl. These reaction mixtures were pre-incubated for 5 minutes at 40° C. Hereafter 1 xylazyme tablet (Megazyme, Ireland) were added to all inhibitor-xylanase mixtures. After 10 minutes of incubation at 40° C., the reactions were terminated, by adding 10 ml 2% Tris/NaOH, pH 12.0. The mixtures were centrifuged and the liberated blue colour from the substrate was measured at 590 nm.

The results are presented in table 10.

TABLE 10

Relative inhibition of xylanase mutants and parent xylanase (here wildtype enzyme) as a function of xylanase inhibitor.

| Mutant ID | 0 | 1.26 | 3.15 | 6.3 | 12.6 |
|---|---|---|---|---|---|
| | | | Relative inhibition, % | | |
| Wildtype | 100 | 77 | 48 | 29 | 23 |
| D11Y | 100 | 120 | 114 | 126 | 124 |
| D11N | 100 | 93 | 72 | 53 | 32 |
| D11F | 100 | 114 | 119 | 116 | 115 |
| D11K | 100 | 109 | 112 | 113 | 116 |
| D11S | 100 | 98 | 81 | 60 | 38 |
| D11W | 100 | 101 | 88 | 70 | 50 |
| G34D | 100 | 94 | 83 | 70 | 53 |
| G34F | 100 | 76 | 53 | 34 | 29 |
| G34T | 100 | 99 | 99 | 93 | 86 |
| Y113A | 100 | 96 | 80 | 62 | 43 |
| Y113D | 100 | 96 | 81 | 63 | 45 |
| Y113K | 100 | 103 | 85 | 63 | 47 |
| N114A | 100 | 80 | 49 | 28 | 22 |
| N114D | 100 | 84 | 57 | 39 | 29 |
| N114F | 100 | 84 | 54 | 39 | 34 |
| N114K | 100 | 87 | 56 | 33 | 24 |
| D121N | 100 | 80 | 36 | 16 | 14 |
| D121K | 100 | 104 | 95 | 85 | 75 |
| D121F | 100 | 101 | 89 | 72 | 60 |
| D121A | 100 | 81 | 50 | 27 | 21 |
| R122D | 100 | 85 | 59 | 41 | 28 |
| R122F | 100 | 93 | 74 | 58 | 58 |
| R122A | 100 | 78 | 46 | 33 | 26 |
| Q175E | 100 | 87 | 59 | 40 | 31 |
| Q175S | 100 | 88 | 59 | 30 | 19 |
| Q175L | 100 | 78 | 42 | 25 | 23 |
| G12F | 100 | 110 | 106 | 100 | 92 |
| G13F | 100 | 104 | 95 | 87 | 84 |
| I15K | 100 | 84 | 47 | 28 | 23 |
| N32K | 100 | 82 | 42 | 19 | 14 |
| G120K | 100 | 85 | 52 | 29 | 22 |
| G120D | 100 | 84 | 47 | 24 | 18 |
| G120F | 100 | 71 | 35 | 18 | 15 |
| G120Y | 100 | 81 | 40 | 18 | 16 |
| G120N | 100 | 84 | 49 | 29 | 23 |
| D119K | 100 | 94 | 67 | 40 | 26 |
| D119Y | 100 | 87 | 50 | 28 | 22 |
| D119N | 100 | 91 | 74 | 44 | 22 |
| T123K | 100 | 80 | 46 | 30 | 25 |
| T123Y | 100 | 80 | 47 | 28 | 27 |
| T123D | 100 | 83 | 36 | 20 | 17 |
| T124K | 100 | 110 | 92 | 73 | 57 |
| T124Y | 100 | 101 | 76 | 49 | 33 |
| T124D | 100 | 87 | 52 | 32 | 25 |
| N17K | 100 | 88 | 48 | 31 | 26 |
| N17Y | 100 | 79 | 42 | 23 | 19 |
| N17D | 100 | 90 | 81 | 50 | 22 |
| N29K | 100 | 83 | 50 | 30 | 23 |
| N29Y | 100 | 85 | 49 | 30 | 24 |
| N29D | 100 | 74 | 44 | 26 | 20 |
| S31K | 100 | 77 | 42 | 23 | 23 |
| S31Y | 100 | 83 | 50 | 27 | 22 |
| S31D | 100 | 79 | 52 | 30 | 24 |
| D11F/R122D | 100 | 109 | 111 | 110 | 109 |
| D11F/G34D | 100 | 104 | 106 | 103 | 104 |

From the results in table 10, it can be seen the xylanase mutants D11Y, D11F, D11K, D11F/R122D and D11F/G34D are uninhibited by the wheat endogenous xylanase inhibitor. These xylanase mutants would be expected to act more aggressively/specifically on the soluble arabinoxylan, compared to the other xylanase mutants or other xylanases. They would therefore be superior in applications where a decrease in viscosity (as a function of HMW arabinoxylan) is wanted.

Example 5

Functionality Studies of Xylanase Mutants

Xylanase mutants expressed in *E. coli* (see Example 3) were fermented and purified (meaning no other xylanolytic activity were present in the purified preparation).

These pure xylanase mutant preparations were diluted to 400 TXU/ml using water and used in the following assay.

Assay 200 ml 30% (w/w) flour slurry was made using water (thermostated to 25° C.), by stirring for 5 minutes. 60.0 ml of this flour slurry is poured into a Ford-cup, and the time for drainage of 50.0 ml is measured. This measurement is the blank measurement. The 60.0 ml flour slurry is poured back and 1000 µl diluted xylanase mutant preparation is added to the flour slurry under stirring. After 2, 5, 10 and 20 minutes, 60.0 ml is poured into the Ford-cup, and the drainage time for 50.0 ml is recorded. Each measurement were done in triplicate.

The results are presented in table 11.

TABLE 11

Relative viscosity of flour slurry as a function of xylanase mutant and parent xylanase (here wild type xylanase)

| Mutant ID | Incubation time, minutes | | | | |
|---|---|---|---|---|---|
| | 0 | 2 | 5 | 10 | 20 |
| | | Relative viscosity change, % | | | |
| Wildtype | 100 | 112 | 120 | 131 | 141 |
| D11Y | 100 | 97 | 93 | 83 | 75 |
| D11N | 100 | 112 | 125 | 130 | 136 |
| D11F | 100 | 93 | 87 | 78 | 69 |
| D11K | 100 | 105 | 95 | 88 | 78 |
| D11S | 100 | 102 | 110 | 113 | 117 |
| D11W | 100 | 106 | 115 | 121 | 122 |
| G34D | 100 | 110 | 120 | 128 | 124 |
| G34F | 100 | 111 | 126 | 128 | 146 |
| G34T | 100 | 100 | 108 | 111 | 106 |
| Y113A | 100 | 118 | 129 | 130 | 124 |
| Y113D | 100 | 116 | 127 | 124 | 114 |
| Y113K | 100 | 118 | 123 | 121 | 115 |
| N114A | 100 | 117 | 128 | 127 | 131 |
| N114D | 100 | 125 | 144 | 162 | 170 |
| N114F | 100 | 113 | 119 | 131 | 150 |
| N114K | 100 | 119 | 129 | 141 | 147 |
| D121N | 100 | 104 | 103 | 106 | 104 |
| D121K | 100 | 122 | 132 | 141 | 162 |
| D121F | 100 | 107 | 117 | 128 | 147 |
| D121A | 100 | 101 | 102 | 103 | 107 |
| R122D | 100 | 120 | 119 | 124 | 115 |
| R122F | 100 | 127 | 144 | 150 | 160 |
| R122A | 100 | 123 | 138 | 144 | 153 |
| Q175E | 100 | 116 | 134 | 142 | 149 |
| Q175S | 100 | 110 | 113 | 121 | 129 |
| Q175L | 100 | 111 | 111 | 119 | 126 |
| G12F | 100 | 127 | 132 | 122 | 101 |
| G13F | 100 | 106 | 119 | 124 | 113 |
| I15K | 100 | 109 | 108 | 113 | 118 |
| N32K | 100 | 97 | 98 | 101 | 101 |
| G120K | 100 | 103 | 111 | 115 | 121 |
| G120D | 100 | 112 | 122 | 120 | 126 |
| G120F | 100 | 103 | 111 | 117 | 130 |
| G120Y | 100 | 106 | 106 | 108 | 126 |
| G120N | 100 | 119 | 123 | 130 | 141 |
| D119K | 100 | 118 | 119 | 127 | 125 |
| D119Y | 100 | 102 | 102 | 111 | 110 |
| D119N | 100 | 126 | 137 | 145 | 146 |
| T123K | 100 | 106 | 109 | 121 | 120 |
| T123Y | 100 | 101 | 106 | 108 | 116 |
| T123D | 100 | 113 | 123 | 125 | 126 |
| T124K | 100 | 117 | 131 | 128 | 127 |
| T124Y | 100 | 112 | 123 | 132 | 135 |
| T124D | 100 | 103 | 110 | 111 | 118 |
| N17K | 100 | 114 | 119 | 119 | 132 |
| N17Y | 100 | 102 | 102 | 108 | 108 |
| N17D | 100 | 120 | 131 | 135 | 143 |
| N29K | 100 | 98 | 100 | 100 | 104 |
| N29Y | 100 | 115 | 117 | 132 | 143 |
| N29D | 100 | 104 | 104 | 113 | 111 |
| S31K | 100 | 119 | 115 | 124 | 134 |
| S31Y | 100 | 110 | 118 | 122 | 137 |
| S31D | 100 | 99 | 103 | 109 | 110 |
| D11F/R122D | 100 | 91 | 89 | 82 | 77 |
| D11F/G34D | 100 | 96 | 93 | 84 | 80 |

Example 6

Site-Directed Mutation in the Active Site of *Bacillus subtilis* Xylanase A, Does Not Influence the Xylanase:Xylanase Inhibitor Interaction A residue in the active site of the *Bacillus subtilis* wildtype xylanase A enzyme was altered by a site-directed mutation (see ex. 3) In the mutated residue (Y166F) a potential hydrogen bond is lost. The mutant xylanase, was expressed in *E. coli*, fermented and purified. Hereafter, the mutant was investigated for its interaction with the xylanase inhibitor (see example 4).

As can be seen below (table 12), the exchange of an amino acid in the active site, did surprisingly not have any effect on interactions with the xylanase inhibitor as compared to the *Bacillus subtilis* wildtype xylanase enzyme.

TABLE 12

Relative inhibition of *Bacillus subtilis* wildtype xylanase and the xylanase mutant Y166F.

| Xylanase ID | XIU/ml | | | | |
|---|---|---|---|---|---|
| | 0 | 1.26 | 3.15 | 6.3 | 12.6 |
| | | | Relative inhibition, % | | |
| Wildtype | 100 | 75 | 40 | 24 | 20 |
| Y166F | 100 | 74 | 39 | 22 | 20 |

Hence, in summary the experiment described above shows a site-directed mutation in the active site of the *Bacillus subtilis* xylanase A, which mutation does not influence the xylanase's interactions with the xylanase inhibitor.

Example 7

Site-Directed Mutation in Family 11 Xylanases Other than the *Bacillus subtilis* Xylanase A, Influencing the Xylanase-Xylanase Inhibitor Interactions D19 residue of the *Thermomyces lanuginosus* xylanase A enzyme was mutated to F19 by site-directed mutagenesis. D19 corresponds to D11 residue in the *Bacillus subtilis* xylanase (SEQ ID NO. 1). *Thermomyces lanuginosus* xylanase A gene is described as SEQ ID NO. 9.

The primers for PCR construction of the D19F mutant may be the following:

```
Sense primer: (SEQ ID NO: 14)
GGTTATTACTATTCCTGGTGGAGTTTTGGAGGAGCGCAGGCCACG

Antisense primer: (SEQ ID NO: 15)
CGTGGCCTGCGCTCCTCCAAAACTCCACCAGGAATAGTAATAACC
```

The obtained mutant xylanase (D19F), was expressed in *E. coil*, fermented and purified. Hereafter, the mutant and the *Thermomyces lanuginosus* wildtype xylanase A was investigated for to its interaction with the xylanase inhibitor (see example 4). As can be seen from the results in table 13, the D19F mutant of the *Thermomyces lanuginosus* xylanase A is significantly less inhibited by the xylanase inhibitor as compared to the *Thermomyces lanuginosus* wildtype xylanase A.

TABLE 13

Relative inhibition of *Thermomyces lanoginosus* wildtype xylanase A (TLX) and the *Thermomyces lanoginosus* mutant xylanase, D19F (D19F).

| Xylanase ID | 0 | 1.26 | XIU/ml 3.15 | 6.3 | 12.6 |
|---|---|---|---|---|---|
| | | | Relative inhibition, % | | |
| TLX | 100 | 45 | 24 | 17 | 14 |
| D19F | 100 | 73 | 38 | 24 | 20 |

Hence, in summary the experiment described above shows a site-directed mutation in the *Thermomyces lanuginosus* xylanase A. The results show that a mutation introducing a substitution of an amino acid on the surface of the xylanase molecule (analogue to the D11F in *B. subtilis*) changes the xylanase:xylanase inhibitor interactions. Thus, our invention (i.e. that surface residues control the level of inhibition of xylanase) holds true for xylanases that are homologous to the *B. subtilis* xylanase.

SUMMARY

In summary, the present invention provides a means for altering the sensitivity of a xylanase enzyme to a xylanase inhibitor.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

Courtin, C., Roelants, A. and Delcour, J. (1999). Fractionation-reconstitution experiments provide insight into the role of endoxylanases in bread-making. Journal of Agricultural and Food Chemistry. 47. 1870-1877.

D'Appolonia, B. L. and MacArthur, L. A. (1976). Comparison of bran and endosperm pentosans in immature and mature wheat. Cereal Chem. 53. 711-718.

Debyser, W. and Delcour, J. A. (1998). Inhibitors of cellolytic, xylanolytic and β-glucanolytic enzymes. WO 98/49278.

Hazlewood, G. P. and Gelbert, H. J. (1993). Recombinant xylanases. PCT application. WO 93/25693.

Ingelbrecht, J. A., Verwimp, T. and Delcour, J. A. (1999). Endoxylanases in durum wheat semolina processing: solubilisation of arabinoxylans, action of endogenous inhibitors and effects on rheological properties. J. Agri. Food Chem.

Jacobsen, T. S., Heldt-Hansen, H. P., Kofod, L. V., Bagger, C. and Müllertz, A. (1995). Processing plant material with xylanase. PCT application. WO 95/23514.

Kormelink, F. J. M. (1992). Characterisation and mode of action of xylanases and some accessory enzymes. Ph.D. Thesis, Agricultural University Wageningen, Holland (175 pp., English and Dutch summaries).

McLauchlan, R., Garcia-Conesa, M. T., Williamson, G., Roza, M., Ravestein, P. and MacGregor, A. W. (1999a). A novel class of protein from wheat which inhibits xylanases. Biochem. J. 338. 441-446.

McLauchlan, R, Flatman, R et al (1999) Poster Presentation from meeting at University of Newcastle (1999) April 11$^{th}$-April 17$^{th}$. Xylanase inhibitors, a novel class of proteins from cereals.

Montgomery, R. and Smith, F. (1955). The Carbohydrates of the Gramineae. VIII. The constitution of a water soluble hemicellulose of the endosperm of wheat (*Triticum vulgare*). J. Am. Chem. Soc. 77. 3325-3328.

Paice, M. G., Bourbonnais, R., Desrochers, M., Jurasek, L. and Yaguchi, M. (1986): A Xylanase Gene from *Bacillus subtilis*: Nucleotide Sequence and Comparison with *B. pumilus* Gene. *Arch. Microbiol.* 144, 201-206.)

Rouau, X. (1993). Investigations into the effects of an enzyme preparation fro baking on wheat flour dough pentosans. J. Cereal Science. 18. 145-157.

Rouau, X., El-Hayek, M-L. and Moreau, D. (1994). Effect of an enzyme preparation containing pentosanases on the bread-making quality of flour in relation to changes in pentosan properties. J. Cereal Science. 19. 259-272.

Slade, L., Levine, H., Craig, S., Arciszewski, H. and Saunders, S. (1993). Enzyme treated low moisture content comestible products. U.S. Pat. No. 5,200,215 by Nabisco.

Soerensen, J. F. and Sibbesen, O. (1999). Bacterial xylanase. UK A 9828599.2.

The invention claimed is:

1. A method of altering the sensitivity of a family 11 parent xylanase polypeptide to an inhibitor, which method comprises modifying one or more amino acid residues of said polypeptide at any one of position 11, 12, 13, 15, 17, 29, 31, 32, 34, 113, 114, 119, 120, 121, 122, 123, 124 or 175 of the *B. subtilis* amino acid sequence shown as SEQ. ID. No. 1, or at equivalent position(s) in other homologous xylanases having at least 80% homology to SEQ ID NO: 1 as determined by using the GCG Wisconsin Bestfit package, and measuring the sensitivity of said xylanase to a xylanase inhibitor, wherein said xylanase inhibitor is a natural inhibitor found specifically in wheat extract;

such that the polypeptide has altered sensitivity to said xylanase inhibitor as compared with the parent xylanase enzyme.

2. A method according to claim 1, wherein said xylanase has at least one of said amino acids modifications at position 11, 12 or 13 of the *B. subtilis* amino acid sequence shown as SEQ. ID. No. 1 or at equivalent position(s) in other homologous xylanases.

3. A method of altering the sensitivity of a family 11 parent xylanase polypeptide to an inhibitor, which method comprises modifying two or more amino acid residues of said polypeptide at two or more of positions 11, 12, 13, 15, 17, 29, 31, 32, 34, 113, 114, 119, 120, 121, 122, 123, 124 and 175 of the *B. subtilis* amino acid sequence shown as SEQ. ID. No. 1, or at equivalent position(s) in other homologous xylanases having at least 80% homology to SEQ ID NO: 1 as determined by using the GCG Wisconsin Bestfit package, wherein one of said amino acid modifications is at position 11; and optionally, measuring the sensitivity of said xylanase to a xylanase inhibitor, wherein said xylanase inhibitor is a natural inhibitor found specifically in wheat extract;

such that the polypeptide has altered sensitivity to said xylanase inhibitor as compared with the parent xylanase enzyme.

4. A method according to claim 1, wherein said amino acid modification is carried out by site-directed mutagenesis.

5. A method according to claim 3, wherein said amino acid modification is carried out by site-directed mutagenesis.

6. A method of altering the sensitivity of a family 11 parent xylanase polypeptide to an inhibitor, which method comprises modifying two or more amino acid residues of said polypeptide at two or more of positions 11, 12, 13, 15, 17, 29, 31, 32, 34, 113, 114, 119, 120, 121, 122, 123, 124 and 175 of the *B. subtilis* amino acid sequence shown as SEQ. ID. No. 1, or at equivalent position(s) in other homologous xylanases having at least 80% homology to SEQ ID NO: 1 as determined by using the GCG Wisconsin Bestfit package, and wherein said amino acid modifications are carried out by site-directed mutagenesis; and optionally, measuring the sensitivity of said xylanase to a xylanase inhibitor, wherein said xylanase inhibitor is a natural inhibitor found specifically in wheat extract;

such that the polypeptide has altered sensitivity to said xylanase inhibitor as compared with the parent xylanase enzyme.

7. The method according to claim 6 wherein one of said amino acid modifications is at position 11, 12 or 13.

8. A method according to claim 1, wherein one of said amino acids modifications is any of: D11Y, D11N, D11F, D11K, D11S, D11W, G12F, G13F, I15K, N17K, N17Y, N17D, N29K, N29Y, N29D, S31K, S31Y, S31D, N32K, G34D, G34F, G34T, Y113A, Y113D, Y113K, N114A, N114D, N114F, N114K, D119K, D119Y, D119N, G120K, G120D, G120F, G120Y, G120N, D121N, D121K, D121F, D121A, R122D, R122F, R122A, T123K, T123Y, T123D, T124K, T124Y, T124D, Q175L, Q175S and Q175L.

9. A method according to claim 3, wherein one of said amino acids modifications is any of: D11Y, D11N, D11F, D11K, D11S, D11W, G12F, G13F, I15K, N17K, N17Y, N17D, N29K, N29Y, N29D, S31K, S31Y, S31D, N32K, G34D, G34F, G34T, Y113A, Y113D, Y113K, N114A, N114D, N114F, N114K, D119K, D119Y, D119N, G120K, G120D, G120F, G120Y, G120N, D121N, D121K, D121F, D121A, R122D, R122F, R122A, T123K, T123Y, T123D, T124K, T124Y, T124D, Q175L, Q175S and Q175L.

10. A method according to claim 6, wherein one of said amino acids modifications is any of: D11Y, D11N, D11F, D11K, D11S, D11W, G12F, G13F, I15K, N17K, N17Y, N17D, N29K, N29Y, N29D, S31K, S31Y, S31D, N32K, G34D, G34F, G34T, Y113A, Y113D, Y113K, N114A, N114D, N114F, N114K, D119K, D119Y, D119N, G120K, G120D, G120F, G120Y, G120N, D121N, D121K, D121F, D121A, R122D, R122F, R122A, T123K, T123Y, T123D, T124K, T124Y, T124D, Q175L, Q175S and Q175L.

11. A method according to claim 1, wherein one of said amino acids modifications is any of: D11Y, D11N, D11F, D11K, D11S or D11W.

12. A method according to claim 3, wherein one of said amino acids modifications is any of: D11Y, D11N, D11F, D11K, D11S or D11W.

13. A method according to claim 6, wherein one of said amino acids modifications is any of: D11Y, D11N, D11F, D11K, D11S or D11W.

14. A method according to claim 1, wherein one of said amino acids modifications is D11F.

15. A method according to claim 3, wherein one of said amino acids modifications is D11F.

16. A method according to claim 6, wherein one of said amino acids modifications is D11F.

17. A method according to claim 1, wherein two of said amino acid modifications are D11F and R122D.

18. A method according to claim 3, wherein two of said amino acid modifications are D11F and R122D.

19. A method according to claim 6, wherein two of said amino acid modifications are D11F and R122D.

20. A method according to claim 1, wherein said sensitivity to an inhibitor is reduced.

21. A method according to claim 3, wherein said sensitivity to an inhibitor is reduced.

22. A method according to claim 6, wherein said sensitivity to an inhibitor is reduced.

* * * * *

UNITED STATES PATENT AND TRADEMARK OFFICE
CERTIFICATE OF CORRECTION

PATENT NO. : 7,527,957 B2  Page 1 of 1
APPLICATION NO. : 11/170653
DATED : May 5, 2009
INVENTOR(S) : Sibbesen et al.

It is certified that error appears in the above-identified patent and that said Letters Patent is hereby corrected as shown below:

Column 106, line 13, in claim 8, replace "Q175L, Q175S and Q175L" with -- Q175E, Q175S and Q175L --.

Column 106, line 22, in claim 9, replace "Q175L, Q175S and Q175L" with -- Q175E, Q175S and Q175L --.

Column 106, line 31, in claim 10, replace "Q175L, Q175S and Q175L" with -- Q175E, Q175S and Q175L --.

Signed and Sealed this

Twenty-third Day of June, 2009

JOHN DOLL
*Acting Director of the United States Patent and Trademark Office*

SEQUENCE LISTING

```
<160> NUMBER OF SEQ ID NOS: 66

<210> SEQ ID NO 1
<211> LENGTH: 185
<212> TYPE: PRT
<213> ORGANISM: Bacillus subtilis
```

-continued

```
<400> SEQUENCE: 1

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 2
<211> LENGTH: 35
<212> TYPE: PRT
<213> ORGANISM: wheat

<400> SEQUENCE: 2

Gly Ala Pro Val Ala Arg Ala Val Glu Ala Val Ala Pro Phe Gly Val
1               5                   10                  15

Cys Tyr Asp Thr Lys Thr Leu Gly Asn Asn Leu Gly Gly Tyr Ala Val
            20                  25                  30

Pro Asn Val
        35

<210> SEQ ID NO 3
<211> LENGTH: 17
<212> TYPE: PRT
<213> ORGANISM: Wheat

<400> SEQUENCE: 3

Lys Arg Leu Gly Phe Ser Arg Leu Pro His Phe Thr Gly Cys Gly Gly
1               5                   10                  15

Leu

<210> SEQ ID NO 4
<211> LENGTH: 21
<212> TYPE: PRT
<213> ORGANISM: Wheat

<400> SEQUENCE: 4

Leu Pro Val Pro Ala Pro Val Thr Lys Asp Pro Ala Thr Ser Leu Tyr
1               5                   10                  15
```

Thr Ile Pro Phe His
         20

<210> SEQ ID NO 5
<211> LENGTH: 31
<212> TYPE: PRT
<213> ORGANISM: Wheat

<400> SEQUENCE: 5

Leu Leu Ala Ser Leu Pro Arg Gly Ser Thr Gly Val Ala Gly Leu Ala
1               5                   10                  15

Asn Ser Gly Leu Ala Leu Pro Ala Gln Val Ala Ser Ala Gln Lys
            20                  25                  30

<210> SEQ ID NO 6
<211> LENGTH: 24
<212> TYPE: PRT
<213> ORGANISM: Wheat

<400> SEQUENCE: 6

Gly Gly Ser Pro Ala His Tyr Ile Ser Ala Arg Phe Ile Glu Val Gly
1               5                   10                  15

Asp Thr Arg Val Pro Ser Val Glu
            20

<210> SEQ ID NO 7
<211> LENGTH: 13
<212> TYPE: PRT
<213> ORGANISM: Wheat

<400> SEQUENCE: 7

Val Asn Val Gly Val Leu Ala Ala Cys Ala Pro Ser Lys
1               5                   10

<210> SEQ ID NO 8
<211> LENGTH: 41
<212> TYPE: PRT
<213> ORGANISM: Wheat

<400> SEQUENCE: 8

Val Ala Asn Arg Phe Leu Leu Cys Leu Pro Thr Gly Gly Pro Gly Val
1               5                   10                  15

Ala Ile Phe Gly Gly Gly Pro Val Pro Trp Pro Gln Phe Thr Gln Ser
            20                  25                  30

Met Pro Tyr Thr Leu Val Val Val Lys
        35                  40

<210> SEQ ID NO 9
<211> LENGTH: 588
<212> TYPE: DNA
<213> ORGANISM: Thermomyces lanuginosus

<400> SEQUENCE: 9
atgcagacaa cccccaactc ggagggctgg cacgatggtt attactattc ctggtggagt      60
gacggtggag cgcaggccac gtacaccaac ctggaaggcg gcacctacga gatcagctgg     120
ggagatggcg gtaacctcgt cggtggaaag ggctggaacc ccggcctgaa cgcaagagcc     180
atccactttg agggtgttta ccagccaaac ggcaacagct accttgcggt ctacggttgg     240
acccgcaacc cgctggtcga gtattacatc gtcgagaact ttggcaccta tgatccttcc     300
tccggtgcta ccgatctagg aactgtcgag tgcgacggta gcatctatcg actcggcaag     360

```
accactcgcg tcaacgcacc tagcatcgac ggcacccaaa ccttcgacca atactggtcg    420
gtccgccagg acaagcgcac cagcggtacc gtccagacgg gctgccactt cgacgcctgg    480
gctcgcgctg gtttgaatgt caacggtgac cactactacc agatcgttgc aacggagggc    540
tacttcagca gcggctatgc tcgcatcacc gttgctgacg tgggctaa                 588

<210> SEQ ID NO 10
<211> LENGTH: 645
<212> TYPE: DNA
<213> ORGANISM: Bacillus subtilis

<400> SEQUENCE: 10
catatgttta agtttaaaaa gaatttctta gttggattat cggcagcttt aatgagtatt     60
agcttgtttt cggcaaccgc ctctgcagct agcacagact actggcaaaa ttggactgat    120
gggggcggta tagtaaacgc tgtcaatggg tctggcggga attacagtgt taattggtct    180
aataccggaa attttgttgt tggtaaaggt tggactacag gttcgccatt taggacgata    240
aactataatg ccggagtttg ggcgccgaat ggcaatggat atttaacttt atatggttgg    300
acgagatcac ctctcataga atattatgta gtggattcat ggggtactta tagacctact    360
ggaacgtata aaggtactgt aaaaagtgat ggggtacat atgacatata tacaactaca    420
cgttataacg caccttccat tgatggcgat cgcactactt ttacgcagta ctggagtgtt    480
cgccagtcga agagaccaac cggaagcaac gctacaatca ctttcagcaa tcatgtgaac    540
gcatggaaga gccatggaat gaatctgggc agtaattggg cttaccaagt catggcgaca    600
gaaggatatc aaagtagtgg aagttctaac gtaacagtgt ggtaa                   645

<210> SEQ ID NO 11
<211> LENGTH: 657
<212> TYPE: DNA
<213> ORGANISM: Unknown
<220> FEATURE:
<223> OTHER INFORMATION: B. subtilis xylanase sequence with added
      restriction site

<400> SEQUENCE: 11
catatgttta agtttaaaaa gaatttctta gttggattat cggcagcttt aatgagtatt     60
agcttgtttt cggcaaccgc ctctgcacat atggctagca cagactactg gcaaaattgg    120
actgatgggg gcggtatagt aaacgctgtc aatgggtctg gcgggaatta cagtgttaat    180
tggtctaata ccggaaattt tgttgttggt aaaggttgga ctacaggttc gccatttagg    240
acgataaact ataatgccgg agtttgggcg ccgaatggca atggatattt aactttatat    300
ggttggacga gatcacctct catagaatat tatgtagtgg attcatgggg tacttataga    360
cctactggaa cgtataaagg tactgtaaaa agtgatgggg tacatatga catatataca    420 actacacgtt ataacgcacc ttccattgat ggcgatcgca ctactttac gcagtactgg    480 agtgttcgcc agtcgaagag accaaccgga agcaacgcta caatcacttt cagcaatcat    540
gtgaacgcat ggaagagcca tggaatgaat ctgggcagta attgggctta ccaagtcatg    600
gcgacagaag gatatcaaag tagtggaagt tctaacgtaa cagtgtggta aaagctt      657

<210> SEQ ID NO 12
<211> LENGTH: 44
<212> TYPE: DNA
<213> ORGANISM: Unknown
<220> FEATURE:
<223> OTHER INFORMATION: sense primer
```

```
<400> SEQUENCE: 12
ctactggcaa aattggactt ttggaggagg tatagtaaac gctg                44

<210> SEQ ID NO 13
<211> LENGTH: 44
<212> TYPE: DNA
<213> ORGANISM: Unknown
<220> FEATURE:
<223> OTHER INFORMATION: Antisense primer

<400> SEQUENCE: 13
cagcgtttac tatacctcct ccaaaagtcc aattttgcca gtag                44

<210> SEQ ID NO 14
<211> LENGTH: 45
<212> TYPE: DNA
<213> ORGANISM: Unknown
<220> FEATURE:
<223> OTHER INFORMATION: Sense primer

<400> SEQUENCE: 14
ggttattact attcctggtg gagttttgga ggagcgcagg ccacg               45

<210> SEQ ID NO 15
<211> LENGTH: 45
<212> TYPE: DNA
<213> ORGANISM: Unknown
<220> FEATURE:
<223> OTHER INFORMATION: Antisense primer

<400> SEQUENCE: 15
cgtggcctgc gctcctccaa aactccacca ggaatagtaa taacc              45

<210> SEQ ID NO 16
<211> LENGTH: 213
<212> TYPE: PRT
<213> ORGANISM: Bacillus subtilis

<400> SEQUENCE: 16
```

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Thr Asp
            20                  25                  30

Tyr Trp Gln Asn Trp Thr Asp Gly Gly Gly Ile Val Asn Ala Val Asn
        35                  40                  45

Gly Ser Gly Gly Asn Tyr Ser Val Asn Trp Ser Asn Thr Gly Asn Phe
    50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
    130                 135                 140

Ser Ile Asp Gly Asp Arg Thr Thr Phe Thr Gln Tyr Trp Ser Val Arg
145                 150                 155                 160

```
Gln Ser Lys Arg Pro Thr Gly Ser Asn Ala Thr Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Met Ala Thr Glu Gly Tyr Gln Ser Ser Gly Ser Ser
        195                 200                 205

Asn Val Thr Val Trp
    210

<210> SEQ ID NO 17
<211> LENGTH: 213
<212> TYPE: PRT
<213> ORGANISM: Bacillus circulans

<400> SEQUENCE: 17

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ser Thr Asp
            20                  25                  30

Tyr Trp Gln Asn Trp Thr Asp Gly Gly Gly Ile Val Asn Ala Val Asn
            35                  40                  45

Gly Ser Gly Gly Asn Tyr Ser Val Asn Trp Ser Asn Thr Gly Asn Phe
50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
            115                 120                 125

Asp Gly Gly Thr Tyr Asp Ile Tyr Thr Thr Thr Arg Tyr Asn Ala Pro
130                 135                 140

Ser Ile Asp Gly Asp Arg Thr Thr Phe Thr Gln Tyr Trp Ser Val Arg
145                 150                 155                 160

Gln Ser Lys Arg Pro Thr Gly Ser Asn Ala Thr Ile Thr Phe Thr Asn
                165                 170                 175

His Val Asn Ala Trp Lys Ser His Gly Met Asn Leu Gly Ser Asn Trp
            180                 185                 190

Ala Tyr Gln Val Met Ala Thr Glu Gly Tyr Gln Ser Ser Gly Ser Ser
        195                 200                 205

Asn Val Thr Val Trp
    210

<210> SEQ ID NO 18
<211> LENGTH: 211
<212> TYPE: PRT
<213> ORGANISM: Bacillus stearothermophilus

<400> SEQUENCE: 18

Met Lys Leu Lys Lys Lys Met Leu Thr Leu Leu Thr Ala Ser Met
1               5                   10                  15

Ser Phe Gly Leu Phe Gly Ala Thr Ser Ser Ala Ala Thr Asp Tyr Trp
            20                  25                  30

Gln Tyr Trp Thr Asp Gly Gly Gly Met Val Asn Ala Val Asn Gly Pro
            35                  40                  45
```

```
Gly Gly Asn Tyr Ser Val Thr Trp Gln Asn Thr Gly Asn Phe Val Val
 50                  55                  60

Gly Lys Gly Trp Thr Val Gly Ser Pro Asn Arg Val Ile Asn Tyr Asn
 65                  70                  75                  80

Ala Gly Ile Trp Glu Pro Ser Gly Asn Gly Tyr Leu Thr Leu Tyr Gly
                 85                  90                  95

Trp Thr Arg Asn Ala Leu Ile Glu Tyr Tyr Val Val Asp Ser Trp Gly
                100                 105                 110

Thr Tyr Arg Ala Thr Gly Asn Tyr Glu Ser Gly Thr Val Asn Ser Asp
            115                 120                 125

Gly Gly Thr Tyr Asp Ile Tyr Thr Thr Met Arg Tyr Asn Ala Pro Ser
130                 135                 140

Ile Asp Gly Thr Gln Thr Phe Gln Gln Phe Trp Ser Val Arg Gln Ser
145                 150                 155                 160

Lys Arg Pro Thr Gly Ser Asn Val Ser Ile Thr Phe Ser Asn His Val
                165                 170                 175

Asn Ala Trp Arg Ser Lys Gly Met Asn Leu Gly Ser Ser Trp Ala Tyr
                180                 185                 190

Gln Val Leu Ala Thr Glu Gly Tyr Gln Ser Ser Gly Arg Ser Asn Val
            195                 200                 205

Thr Val Trp
210

<210> SEQ ID NO 19
<211> LENGTH: 211
<212> TYPE: PRT
<213> ORGANISM: A. caviae

<400> SEQUENCE: 19

Met Phe Lys Phe Gly Lys Lys Leu Met Thr Val Val Leu Ala Ala Ser
 1               5                  10                  15

Met Ser Phe Gly Val Phe Ala Ala Thr Ser Ser Ala Ala Thr Asp Tyr
                 20                  25                  30

Trp Gln Asn Trp Thr Asp Gly Gly Gly Thr Val Asn Ala Val Asn Gly
             35                  40                  45

Ser Gly Gly Asn Tyr Ser Val Ser Trp Gln Asn Thr Gly Asn Phe Val
 50                  55                  60

Val Gly Lys Gly Trp Thr Tyr Gly Thr Pro Asn Arg Val Val Asn Tyr
 65                  70                  75                  80

Asn Ala Gly Val Phe Ala Pro Ser Gly Asn Gly Tyr Leu Thr Phe Tyr
                 85                  90                  95

Gly Trp Thr Arg Asn Ala Leu Ile Glu Tyr Tyr Val Val Asp Ser Trp
                100                 105                 110

Gly Thr Tyr Arg Pro Thr Gly Thr Tyr Lys Gly Thr Val Asn Ser Asp
            115                 120                 125

Gly Gly Thr Tyr Asp Ile Tyr Thr Thr Met Arg Tyr Asn Ala Pro Ser
130                 135                 140

Ile Asp Gly Thr Gln Thr Phe Pro Gln Tyr Trp Ser Val Arg Gln Ser
145                 150                 155                 160

Lys Arg Pro Thr Gly Val Asn Ser Thr Ile Thr Phe Ser Asn His Val
                165                 170                 175

Asn Ala Trp Pro Ser Lys Gly Met Tyr Leu Gly Asn Ser Trp Ser Tyr
                180                 185                 190

Gln Val Met Ala Thr Glu Gly Tyr Gln Ser Ser Gly Asn Ala Asn Val
            195                 200                 205
```

Thr Val Trp
    210

<210> SEQ ID NO 20
<211> LENGTH: 221
<212> TYPE: PRT
<213> ORGANISM: C. carbonum

<400> SEQUENCE: 20

Met Val Ser Phe Thr Ser Ile Ile Thr Ala Ala Val Ala Ala Thr Gly
1               5                   10                  15

Ala Leu Ala Ala Pro Ala Thr Asp Val Ser Leu Val Ala Arg Gln Asn
            20                  25                  30

Thr Pro Asn Gly Glu Gly Thr His Asn Gly Cys Phe Trp Ser Trp Trp
        35                  40                  45

Ser Asp Gly Gly Ala Arg Ala Thr Tyr Thr Asn Gly Ala Gly Gly Ser
    50                  55                  60

Tyr Ser Val Ser Trp Gly Ser Gly Gly Asn Leu Val Gly Gly Lys Gly
65                  70                  75                  80

Trp Asn Pro Gly Thr Ala Arg Thr Ile Thr Tyr Ser Gly Thr Tyr Asn
                85                  90                  95

Tyr Asn Gly Asn Ser Tyr Leu Ala Val Tyr Gly Trp Thr Arg Asn Pro
            100                 105                 110

Leu Val Glu Tyr Tyr Val Val Glu Asn Phe Gly Thr Tyr Asp Pro Ser
        115                 120                 125

Ser Gln Ser Gln Asn Lys Gly Thr Val Thr Ser Asp Gly Ser Ser Tyr
    130                 135                 140

Lys Ile Ala Gln Ser Thr Arg Thr Asn Gln Pro Ser Ile Asp Gly Thr
145                 150                 155                 160

Arg Thr Phe Gln Gln Tyr Trp Ser Val Arg Gln Asn Lys Arg Ser Ser
                165                 170                 175

Gly Ser Val Asn Met Lys Thr His Phe Asp Ala Trp Ala Ser Lys Gly
            180                 185                 190

Met Asn Leu Gly Gln His Tyr Tyr Gln Ile Val Ala Thr Glu Gly Tyr
        195                 200                 205

Phe Ser Thr Gly Asn Ala Gln Ile Thr Val Asn Cys Pro
    210                 215                 220

<210> SEQ ID NO 21
<211> LENGTH: 227
<212> TYPE: PRT
<213> ORGANISM: H. turcicum

<400> SEQUENCE: 21

Met Val Ser Phe Thr Ser Ile Ile Thr Ala Ala Val Ala Ala Thr Gly
1               5                   10                  15

Ala Leu Ala Ala Pro Ala Thr Asp Ile Ala Ala Arg Ala Pro Ser Asp
            20                  25                  30

Leu Val Ala Arg Gln Ser Thr Pro Asn Gly Glu Gly Thr His Asn Gly
        35                  40                  45

Cys Phe Tyr Ser Trp Trp Ser Asp Gly Gly Ala Arg Ala Thr Tyr Thr
    50                  55                  60

Asn Gly Ala Gly Gly Ser Tyr Ser Val Ser Trp Gly Thr Gly Gly Asn
65                  70                  75                  80

Leu Val Gly Gly Lys Gly Trp Asn Pro Gly Thr Ala Arg Thr Ile Thr
                85                  90                  95

```
Tyr Ser Gly Gln Tyr Asn Pro Asn Gly Asn Ser Tyr Leu Ala Ile Tyr
                100                 105                 110

Gly Trp Thr Arg Asn Pro Leu Val Glu Tyr Tyr Val Glu Asn Phe
        115                 120                 125

Gly Thr Tyr Asp Pro Ser Ser Gln Ala Gln Asn Lys Gly Thr Val Thr
        130                 135                 140

Ser Asp Gly Ser Ser Tyr Lys Ile Ala Gln Ser Thr Arg Thr Asn Gln
145                 150                 155                 160

Pro Ser Ile Asp Gly Thr Arg Thr Phe Gln Gln Tyr Trp Ser Val Arg
                165                 170                 175

Gln Asn Lys Arg Ser Ser Gly Ser Val Asn Met Lys Thr His Phe Asp
                180                 185                 190

Ala Trp Ala Ser Lys Gly Met Asn Leu Gly Ser His Tyr Tyr Gln Ile
                195                 200                 205

Val Ala Thr Glu Gly Tyr Phe Ser Ser Gly Ser Ala Ser Ile Thr Val
                210                 215                 220

Asn Cys Pro
225

<210> SEQ ID NO 22
<211> LENGTH: 227
<212> TYPE: PRT
<213> ORGANISM: A. pisi

<400> SEQUENCE: 22

Met Val Ser Phe Thr Ser Ile Phe Thr Ala Ala Val Ala Ala Thr Gly
1               5                   10                  15

Ala Leu Ala Val Pro Val Thr Asp Leu Ala Thr Arg Ser Leu Gly Ala
                20                  25                  30

Leu Thr Ala Arg Ala Gly Thr Pro Ser Ser Gln Gly Thr His Asn Gly
            35                  40                  45

Cys Phe Tyr Ser Trp Trp Thr Asp Gly Gly Ala Gln Ala Thr Tyr Thr
        50                  55                  60

Asn Gly Ala Gly Gly Ser Tyr Ser Val Asn Trp Lys Thr Gly Gly Asn
65                  70                  75                  80

Leu Val Gly Gly Lys Gly Trp Asn Pro Gly Ala Ala Arg Thr Ile Thr
                85                  90                  95

Tyr Ser Gly Thr Tyr Ser Pro Ser Gly Asn Ser Tyr Leu Ala Val Tyr
                100                 105                 110

Gly Trp Thr Arg Asn Pro Leu Ile Glu Tyr Tyr Val Glu Asn Phe
        115                 120                 125

Gly Thr Tyr Asp Pro Ser Ser Gln Ala Thr Val Lys Gly Ser Val Thr
        130                 135                 140

Ala Asp Gly Ser Ser Tyr Lys Ile Ala Gln Thr Gln Arg Thr Asn Gln
145                 150                 155                 160

Pro Ser Ile Asp Gly Thr Gln Thr Phe Gln Gln Tyr Trp Ser Val Arg
                165                 170                 175

Gln Asn Lys Arg Ser Ser Gly Ser Val Asn Met Lys Thr His Phe Asp
                180                 185                 190

Ala Trp Ala Ala Lys Gly Met Lys Leu Gly Thr His Asn Tyr Gln Ile
                195                 200                 205

Val Ala Thr Glu Gly Tyr Phe Ser Ser Gly Ser Ala Gln Ile Thr Val
                210                 215                 220

Asn Cys Ala
```

-continued

225

<210> SEQ ID NO 23
<211> LENGTH: 201
<212> TYPE: PRT
<213> ORGANISM: S. commune

<400> SEQUENCE: 23

Ala Ala Ser Gly Thr Pro Ser Ser Thr Gly Thr Asp Gly Gly Tyr Tyr
1               5                   10                  15

Tyr Ser Trp Trp Thr Asp Gly Ala Gly Asp Ala Thr Tyr Gln Asn Asn
            20                  25                  30

Gly Gly Gly Ser Tyr Thr Leu Thr Trp Ser Gly Asn Asn Gly Asn Leu
        35                  40                  45

Val Gly Gly Lys Gly Trp Asn Pro Gly Ala Ala Ser Arg Ser Ile Ser
50                  55                  60

Tyr Ser Gly Thr Tyr Gln Pro Asn Gly Asn Ser Tyr Leu Ser Val Tyr
65                  70                  75                  80

Gly Trp Thr Arg Ser Ser Leu Ile Glu Tyr Tyr Ile Val Glu Ser Tyr
                85                  90                  95

Gly Ser Tyr Asp Pro Ser Ser Ala Ala Ser His Lys Gly Ser Val Thr
            100                 105                 110

Cys Asn Gly Ala Thr Tyr Asp Ile Leu Ser Thr Trp Arg Tyr Asn Ala
        115                 120                 125

Pro Ser Ile Asp Gly Thr Gln Thr Phe Glu Gln Phe Trp Ser Val Arg
130                 135                 140

Asn Pro Lys Lys Ala Pro Gly Gly Ser Ile Ser Gly Thr Val Asp Val
145                 150                 155                 160

Gln Cys His Phe Asp Ala Trp Lys Gly Leu Gly Met Asn Leu Gly Ser
                165                 170                 175

Glu His Asn Tyr Gln Ile Val Ala Thr Glu Gly Tyr Gln Ser Ser Gly
            180                 185                 190

Thr Ala Thr Ile Thr Val Thr Ala Ser
        195                 200

<210> SEQ ID NO 24
<211> LENGTH: 225
<212> TYPE: PRT
<213> ORGANISM: T. lanuginosus

<400> SEQUENCE: 24

Met Val Gly Phe Thr Pro Val Ala Leu Ala Ala Leu Ala Ala Thr Gly
1               5                   10                  15

Ala Leu Ala Phe Pro Ala Gly Asn Ala Thr Glu Leu Glu Lys Arg Gln
            20                  25                  30

Thr Thr Pro Asn Ser Glu Gly Trp His Asp Gly Tyr Tyr Tyr Ser Trp
        35                  40                  45

Trp Ser Asp Gly Gly Ala Gln Ala Thr Tyr Thr Asn Leu Glu Gly Gly
    50                  55                  60

Thr Tyr Glu Ile Ser Trp Gly Asp Gly Asn Leu Val Gly Gly Lys
65                  70                  75                  80

Gly Trp Asn Pro Gly Leu Asn Ala Arg Ala Ile His Phe Glu Gly Val
                85                  90                  95

Tyr Gln Pro Asn Gly Asn Ser Tyr Leu Ala Val Tyr Gly Trp Thr Arg
            100                 105                 110

Asn Pro Leu Val Glu Tyr Tyr Ile Val Glu Asn Phe Gly Thr Tyr Asp

-continued

```
            115                 120                 125
Pro Ser Ser Gly Ala Thr Asp Leu Gly Thr Val Glu Cys Asp Gly Ser
        130                 135                 140

Ile Tyr Arg Leu Gly Lys Thr Thr Arg Val Asn Ala Pro Ser Ile Asp
145                 150                 155                 160

Gly Thr Gln Thr Phe Asp Gln Tyr Trp Ser Val Arg Gln Asp Lys Arg
                165                 170                 175

Thr Ser Gly Thr Val Gln Thr Gly Cys His Phe Asp Ala Trp Ala Arg
            180                 185                 190

Ala Gly Leu Asn Val Asn Gly Asp His Tyr Tyr Gln Ile Val Ala Thr
        195                 200                 205

Glu Gly Tyr Phe Ser Ser Gly Tyr Ala Arg Ile Thr Val Ala Asp Val
    210                 215                 220

Gly
225
```

<210> SEQ ID NO 25
<211> LENGTH: 231
<212> TYPE: PRT
<213> ORGANISM: C. carbonum

<400> SEQUENCE: 25

```
Met Val Ser Phe Lys Ser Leu Leu Ala Ala Val Ala Thr Thr Ser
1               5                   10                  15

Val Leu Ala Ala Pro Phe Asp Phe Leu Arg Glu Arg Asp Asp Val Asn
            20                  25                  30

Ala Thr Ala Leu Leu Glu Lys Arg Gln Ser Thr Pro Ser Ala Glu Gly
        35                  40                  45

Tyr His Asn Gly Tyr Phe Tyr Ser Trp Trp Thr Asp Gly Gly Gly Ser
    50                  55                  60

Ala Gln Tyr Thr Met Gly Glu Gly Ser Arg Tyr Ser Val Thr Trp Arg
65                  70                  75                  80

Asn Thr Gly Asn Phe Val Gly Gly Lys Gly Trp Asn Pro Gly Ser Gly
                85                  90                  95

Arg Val Ile Asn Tyr Gly Gly Ala Phe Asn Pro Gln Gly Asn Gly Tyr
            100                 105                 110

Leu Ala Val Tyr Gly Trp Thr Arg Asn Pro Leu Val Glu Tyr Tyr Val
        115                 120                 125

Ile Glu Ser Tyr Gly Thr Tyr Asn Pro Ser Ser Gly Ala Gln Ile Lys
    130                 135                 140

Gly Ser Phe Gln Thr Asp Gly Gly Thr Tyr Asn Val Ala Val Ser Thr
145                 150                 155                 160

Arg Tyr Asn Gln Pro Ser Ile Asp Gly Thr Arg Thr Phe Gln Gln Tyr
                165                 170                 175

Trp Ser Val Arg Thr Gln Lys Arg Val Gly Gly Ser Val Asn Met Gln
            180                 185                 190

Asn His Phe Asn Ala Trp Ser Arg Tyr Gly Leu Asn Leu Gly Gln His
        195                 200                 205

Tyr Tyr Gln Ile Val Ala Thr Glu Gly Tyr Gln Ser Ser Gly Ser Ser
    210                 215                 220

Asp Ile Tyr Val Gln Thr Gln
225                 230
```

<210> SEQ ID NO 26
<211> LENGTH: 231

```
<212> TYPE: PRT
<213> ORGANISM: C. sativus

<400> SEQUENCE: 26

Met Val Ser Phe Lys Ser Leu Leu Ala Ala Val Ala Thr Thr Ser
1               5                   10                  15

Val Leu Ala Ala Pro Phe Asp Phe Leu Arg Glu Arg Asp Asp Gly Asn
                20                  25                  30

Ala Thr Ala Leu Leu Glu Lys Arg Gln Ser Thr Pro Ser Ser Glu Gly
            35                  40                  45

Tyr His Asn Gly Tyr Phe Tyr Ser Trp Trp Thr Asp Gly Gly Gly Ser
    50                  55                  60

Ala Gln Tyr Thr Met Gly Glu Gly Ser Arg Tyr Ser Val Thr Trp Arg
65                  70                  75                  80

Asn Thr Gly Asn Phe Val Gly Gly Lys Gly Trp Asn Pro Gly Thr Gly
                85                  90                  95

Arg Val Ile Asn Tyr Gly Gly Ala Phe Asn Pro Gln Gly Asn Gly Tyr
                100                 105                 110

Leu Ala Val Tyr Gly Trp Thr Arg Asn Pro Leu Val Glu Tyr Tyr Val
                115                 120                 125

Ile Glu Ser Tyr Gly Thr Tyr Asn Pro Ser Ser Gly Ala Gln Val Lys
                130                 135                 140

Gly Ser Phe Gln Thr Asp Gly Gly Thr Tyr Asn Val Ala Val Ser Thr
145                 150                 155                 160

Arg Tyr Asn Gln Pro Ser Ile Asp Gly Thr Arg Thr Phe Gln Gln Tyr
                165                 170                 175

Trp Ser Val Arg Gln Gln Lys Arg Val Gly Gly Ser Val Asn Met Gln
                180                 185                 190

Asn His Phe Asn Ala Trp Ser Arg Tyr Gly Leu Asn Leu Gly Gln His
                195                 200                 205

Tyr Tyr Gln Ile Val Ala Thr Glu Gly Tyr Gln Ser Ser Gly Ser Ser
                210                 215                 220

Asp Ile Tyr Val Gln Thr Gln
225                 230

<210> SEQ ID NO 27
<211> LENGTH: 227
<212> TYPE: PRT
<213> ORGANISM: H. insolens

<400> SEQUENCE: 27

Met Val Ser Leu Lys Ser Val Leu Ala Ala Thr Ala Val Ser Ser
1               5                   10                  15

Ala Ile Ala Ala Pro Phe Asp Phe Val Pro Arg Asp Asn Ser Thr Ala
                20                  25                  30

Leu Gln Ala Arg Gln Val Thr Pro Asn Ala Glu Gly Trp His Asn Gly
            35                  40                  45

Tyr Phe Tyr Ser Trp Trp Ser Asp Gly Gly Gly Gln Val Gln Tyr Thr
    50                  55                  60

Asn Leu Glu Gly Ser Arg Tyr Gln Val Arg Trp Arg Asn Thr Gly Asn
65                  70                  75                  80

Phe Val Gly Gly Lys Gly Trp Asn Pro Gly Thr Gly Arg Thr Ile Asn
                85                  90                  95

Tyr Gly Gly Tyr Phe Asn Pro Gln Gly Asn Gly Tyr Leu Ala Val Tyr
                100                 105                 110
```

```
Gly Trp Thr Arg Asn Pro Leu Val Glu Tyr Tyr Val Ile Glu Ser Tyr
            115                 120                 125

Gly Thr Tyr Asn Pro Gly Ser Gln Ala Gln Tyr Lys Gly Thr Phe Tyr
        130                 135                 140

Thr Asp Gly Asp Gln Tyr Asp Ile Phe Val Ser Thr Arg Tyr Asn Gln
145                 150                 155                 160

Pro Ser Ile Asp Gly Thr Arg Thr Phe Gln Gln Tyr Trp Ser Ile Arg
                165                 170                 175

Lys Asn Lys Arg Val Gly Gly Ser Val Asn Met Gln Asn His Phe Asn
            180                 185                 190

Ala Trp Gln Gln His Gly Met Pro Leu Gly Gln His Tyr Tyr Gln Val
        195                 200                 205

Val Ala Thr Glu Gly Tyr Gln Ser Ser Gly Glu Ser Asp Ile Tyr Val
210                 215                 220

Gln Thr His
225

<210> SEQ ID NO 28
<211> LENGTH: 233
<212> TYPE: PRT
<213> ORGANISM: M. grisea

<400> SEQUENCE: 28

Met Val Ser Phe Thr Ser Ile Val Thr Ala Val Val Ala Leu Ala Gly
1               5                   10                  15

Ser Ala Leu Ala Ile Pro Ala Pro Asp Gly Asn Met Thr Gly Phe Pro
            20                  25                  30

Phe Glu Gln Leu Met Arg Arg Gln Ser Thr Pro Ser Ser Thr Gly Arg
        35                  40                  45

His Asn Gly Tyr Tyr Tyr Ser Trp Trp Thr Asp Gly Ala Ser Pro Val
    50                  55                  60

Gln Tyr Gln Asn Gly Asn Gly Ser Tyr Ser Val Gln Trp Gln Ser
65                  70                  75                  80

Gly Gly Asn Phe Val Gly Gly Lys Gly Trp Met Pro Gly Gly Ser Lys
                85                  90                  95

Ser Ile Thr Tyr Ser Gly Thr Phe Asn Pro Val Asn Asn Gly Asn Ala
            100                 105                 110

Tyr Leu Cys Ile Tyr Gly Trp Thr Gln Asn Pro Leu Val Glu Tyr Tyr
        115                 120                 125

Ile Leu Glu Asn Tyr Gly Glu Tyr Asn Pro Gly Asn Ser Ala Gln Ser
    130                 135                 140

Arg Gly Thr Leu Gln Ala Ala Gly Gly Thr Tyr Thr Leu His Glu Ser
145                 150                 155                 160

Thr Arg Val Asn Gln Pro Ser Ile Glu Gly Thr Arg Thr Phe Gln Gln
                165                 170                 175

Tyr Trp Ala Ile Arg Gln Gln Lys Arg Asn Ser Gly Thr Val Asn Thr
            180                 185                 190

Gly Glu Phe Phe Gln Ala Trp Glu Arg Ala Gly Met Arg Met Gly Asn
        195                 200                 205

His Asn Tyr Met Ile Val Ala Thr Glu Gly Tyr Arg Ser Ala Gly Asn
    210                 215                 220

Ser Asn Ile Asn Val Gln Thr Pro Ala
225                 230

<210> SEQ ID NO 29
```

<211> LENGTH: 219
<212> TYPE: PRT
<213> ORGANISM: C. gracile

<400> SEQUENCE: 29

```
Met Val Ser Phe Lys Ala Leu Leu Gly Ala Ala Gly Ala Leu Ala
1               5                   10                  15

Phe Pro Phe Asn Val Thr Gln Met Asn Glu Leu Val Ala Arg Ala Gly
                20                  25                  30

Thr Pro Ser Gly Thr Gly Thr Asn Asn Gly Tyr Phe Tyr Ser Phe Trp
            35                  40                  45

Thr Asp Gly Gly Gly Thr Val Asn Tyr Gln Asn Gly Ala Gly Gly Ser
        50                  55                  60

Tyr Ser Val Gln Trp Gln Asn Cys Gly Asn Phe Val Gly Gly Lys Gly
65                  70                  75                  80

Trp Asn Pro Gly Ala Ala Arg Thr Ile Asn Phe Ser Gly Thr Phe Ser
                85                  90                  95

Pro Gln Gly Asn Gly Tyr Leu Ala Ile Tyr Gly Trp Thr Gln Asn Pro
            100                 105                 110

Leu Val Glu Tyr Tyr Ile Val Glu Ser Phe Gly Thr Tyr Asp Pro Ser
        115                 120                 125

Ser Gln Ala Ser Lys Phe Gly Thr Ile Gln Gln Asp Gly Ser Thr Tyr
    130                 135                 140

Thr Ile Ala Lys Thr Thr Arg Val Asn Gln Pro Ser Ile Glu Gly Thr
145                 150                 155                 160

Ser Thr Phe Asp Gln Phe Trp Ser Val Arg Gln Asn His Arg Ser Ser
                165                 170                 175

Gly Ser Val Asn Val Ala Ala His Phe Asn Ala Trp Ala Gln Ala Gly
            180                 185                 190

Leu Lys Leu Gly Ser His Asn Tyr Gln Ile Val Ala Thr Glu Gly Tyr
        195                 200                 205

Gln Ser Ser Gly Ser Ser Ser Ile Thr Val Ser
    210                 215
```

<210> SEQ ID NO 30
<211> LENGTH: 223
<212> TYPE: PRT
<213> ORGANISM: T. reesei

<400> SEQUENCE: 30

```
Met Val Ser Phe Thr Ser Leu Leu Ala Gly Val Ala Ala Ile Ser Gly
1               5                   10                  15

Val Leu Ala Ala Pro Ala Ala Glu Val Glu Pro Val Ala Val Glu Lys
                20                  25                  30

Arg Gln Thr Ile Gln Pro Gly Thr Gly Tyr Asn Asn Gly Tyr Phe His
            35                  40                  45

Ser Tyr Trp Asn Asp Gly His Gly Gly Val Thr Tyr Thr Asn Gly Pro
        50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110

Ser Arg Asn Pro Leu Ile Glu Tyr Tyr Ile Val Gly Asn Phe Gly Thr
        115                 120                 125
```

```
Tyr Asn Pro Ser Thr Gly Ala Thr Lys Leu Gly Glu Val Thr Ser Asp
        130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
    210                 215                 220
```

<210> SEQ ID NO 31
<211> LENGTH: 223
<212> TYPE: PRT
<213> ORGANISM: T. reesei

<400> SEQUENCE: 31

```
Met Val Ser Phe Thr Ser Leu Leu Ala Gly Val Ala Ala Ile Ser Gly
1               5                   10                  15

Val Leu Ala Ala Pro Ala Ala Glu Val Glu Ser Val Ala Val Glu Lys
            20                  25                  30

Arg Gln Thr Ile Gln Pro Gly Thr Gly Tyr Asn Asn Gly Tyr Phe Tyr
        35                  40                  45

Ser Tyr Trp Asn Asp Gly His Gly Gly Val Thr Tyr Thr Asn Gly Pro
    50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110

Ser Arg Asn Pro Leu Ile Glu Tyr Tyr Ile Val Glu Asn Phe Gly Thr
        115                 120                 125

Tyr Asn Pro Ser Thr Gly Ala Thr Lys Leu Gly Glu Val Thr Ser Asp
    130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
    210                 215                 220
```

<210> SEQ ID NO 32
<211> LENGTH: 222
<212> TYPE: PRT
<213> ORGANISM: T. reesei

<400> SEQUENCE: 32

```
Met Val Ser Phe Thr Ser Leu Leu Ala Ala Ser Pro Pro Ser Arg Ala
1               5                   10                  15
```

```
Ser Cys Arg Pro Ala Ala Glu Val Glu Ser Val Ala Val Glu Lys Arg
             20                  25                  30

Gln Thr Ile Gln Pro Gly Thr Gly Tyr Asn Asn Gly Tyr Phe Tyr Ser
             35                  40                  45

Tyr Trp Asn Asp Gly His Gly Gly Val Thr Tyr Thr Asn Gly Pro Gly
 50                  55                  60

Gly Gln Phe Ser Val Asn Trp Ser Asn Ser Gly Asn Phe Val Gly Gly
 65                  70                  75                  80

Lys Gly Trp Gln Pro Gly Thr Lys Asn Lys Val Ile Asn Phe Ser Gly
             85                  90                  95

Ser Tyr Asn Pro Asn Gly Asn Ser Tyr Leu Ser Val Tyr Gly Trp Ser
            100                 105                 110

Arg Asn Pro Leu Ile Glu Tyr Tyr Ile Val Glu Asn Phe Gly Thr Tyr
            115                 120                 125

Asn Pro Ser Thr Gly Ala Thr Lys Leu Gly Glu Val Thr Ser Asp Gly
        130                 135                 140

Ser Val Tyr Asp Ile Tyr Arg Thr Gln Arg Val Asn Gln Pro Ser Ile
145                 150                 155                 160

Ile Gly Thr Ala Thr Phe Tyr Gln Tyr Trp Ser Val Arg Arg Asn His
                165                 170                 175

Arg Ser Ser Gly Ser Val Asn Thr Ala Asn His Phe Asn Ala Trp Ala
            180                 185                 190

Gln Gln Gly Leu Thr Leu Gly Thr Met Asp Tyr Gln Ile Val Ala Val
            195                 200                 205

Glu Gly Tyr Phe Ser Ser Gly Ser Ala Ser Ile Thr Val Ser
        210                 215                 220

<210> SEQ ID NO 33
<211> LENGTH: 190
<212> TYPE: PRT
<213> ORGANISM: T. harzianum

<400> SEQUENCE: 33

Gln Thr Ile Gly Pro Gly Thr Gly Tyr Ser Asn Gly Tyr Tyr Tyr Ser
 1               5                  10                  15

Tyr Trp Asn Asp Gly His Ala Gly Val Thr Tyr Thr Asn Gly Gly Gly
             20                  25                  30

Gly Ser Phe Thr Val Asn Trp Ser Asn Ser Gly Asn Phe Val Ala Gly
             35                  40                  45

Lys Gly Trp Gln Pro Gly Thr Lys Asn Lys Val Ile Asn Phe Ser Gly
         50                  55                  60

Ser Tyr Asn Pro Asn Gly Asn Ser Tyr Leu Ser Ile Tyr Gly Trp Ser
 65                  70                  75                  80

Arg Asn Pro Leu Ile Glu Tyr Tyr Ile Val Glu Asn Phe Gly Thr Tyr
             85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
```

```
                    165                 170                 175

Glu Gly Tyr Phe Ser Ser Gly Ser Ala Ser Ile Thr Val Ser
            180                 185                 190

<210> SEQ ID NO 34
<211> LENGTH: 223
<212> TYPE: PRT
<213> ORGANISM: T. viride

<400> SEQUENCE: 34

Met Val Ser Phe Thr Thr Leu Leu Ala Gly Phe Val Ala Val Thr Gly
1               5                   10                  15

Val Leu Ser Ala Pro Thr Glu Thr Val Glu Val Val Asp Val Glu Lys
            20                  25                  30

Arg Gln Thr Ile Gly Pro Gly Thr Gly Phe Asn Asn Gly Tyr Tyr Tyr
        35                  40                  45

Ser Tyr Trp Asn Asp Gly His Ser Gly Val Thr Tyr Thr Asn Gly Ala
    50                  55                  60

Gly Gly Ser Phe Ser Val Asn Trp Ala Asn Ser Gly Asn Phe Val Gly
65                  70                  75                  80

Gly Lys Gly Trp Asn Pro Gly Ser Ser Arg Val Ile Asn Phe Ser
                85                  90                  95

Gly Ser Tyr Asn Pro Asn Gly Asn Ser Tyr Leu Ser Val Tyr Gly Trp
            100                 105                 110

Ser Lys Asn Pro Leu Ile Glu Tyr Tyr Ile Val Glu Asn Phe Gly Thr
        115                 120                 125

Tyr Asn Pro Ser Thr Gly Thr Thr Lys Leu Gly Glu Val Thr Ser Asp
    130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Ala Pro Ala Ala Arg Ser Arg Leu Arg Thr Thr Ser Asn Ala Trp
            180                 185                 190

Arg Asn Leu Gly Leu Thr Leu Gly Thr Leu Asp Tyr Gln Ile Ile Ala
        195                 200                 205

Val Glu Gly Tyr Phe Ser Ser Gly Asn Ala Asn Ile Asn Val Ser
    210                 215                 220

<210> SEQ ID NO 35
<211> LENGTH: 241
<212> TYPE: PRT
<213> ORGANISM: C. gracile

<400> SEQUENCE: 35

Met Val Asn Phe Ser Ser Leu Phe Leu Ala Ala Ser Ala Ala Val Val
1               5                   10                  15

Ala Val Ala Ala Pro Gly Glu Leu Pro Gly Met His Lys Arg Gln Thr
            20                  25                  30

Leu Thr Ser Ser Gln Thr Gly Thr Asn Asn Gly Tyr Tyr Tyr Ser Phe
        35                  40                  45

Trp Thr Asp Gly Gln Gly Asn Val Gln Tyr Thr Asn Glu Ala Gly Gly
    50                  55                  60

Gln Tyr Ser Val Thr Trp Ser Asn Gly Asn Trp Val Gly Gly Lys
65                  70                  75                  80

Gly Trp Asn Pro Gly Ser Ala Arg Thr Ile Asn Tyr Thr Ala Asn Tyr
```

-continued

```
                    85                  90                  95
Asn Pro Asn Gly Asn Ser Tyr Leu Ala Val Tyr Gly Trp Thr Arg Asn
            100                 105                 110
Pro Leu Ile Glu Tyr Tyr Val Glu Asn Phe Gly Thr Tyr Asn Pro
        115                 120                 125
Ser Thr Gly Ala Thr Arg Leu Gly Ser Val Thr Asp Gly Ser Cys
    130                 135                 140
Tyr Asp Ile Tyr Arg Thr Gln Arg Val Asn Gln Pro Ser Ile Glu Gly
145                 150                 155                 160
Thr Ser Thr Phe Tyr Gln Phe Trp Ser Val Arg Gln Asn Lys Arg Ser
                165                 170                 175
Gly Gly Ser Val Asn Met Ala Ala His Phe Asn Ala Trp Ala Ala Ala
            180                 185                 190
Gly Leu Gln Leu Gly Thr His Asp Tyr Gln Ile Val Ala Thr Glu Gly
        195                 200                 205
Tyr Tyr Ser Ser Gly Ser Ala Thr Val Asn Val Gly Ala Ser Ser Asp
    210                 215                 220
Gly Ser Thr Gly Gly Ser Thr Gly Gly Ser Thr Asn Val Ser
225                 230                 235                 240
Phe
```

<210> SEQ ID NO 36
<211> LENGTH: 225
<212> TYPE: PRT
<213> ORGANISM: A. niger

<400> SEQUENCE: 36

```
Met Leu Thr Lys Asn Leu Leu Cys Phe Ala Ala Lys Ala Ala
1               5                   10                  15
Leu Ala Val Pro His Asp Ser Val Ala Gln Arg Ser Asp Ala Leu His
            20                  25                  30
Met Leu Ser Glu Arg Ser Thr Pro Ser Ser Thr Gly Glu Asn Asn Gly
        35                  40                  45
Phe Tyr Tyr Ser Phe Trp Thr Asp Gly Gly Asp Val Thr Tyr Thr
    50                  55                  60
Asn Gly Asp Ala Gly Ala Tyr Thr Val Glu Trp Ser Asn Val Gly Asn
65                  70                  75                  80
Phe Val Gly Gly Lys Gly Trp Asn Pro Gly Ser Ala Gln Asp Ile Thr
                85                  90                  95
Tyr Ser Gly Thr Phe Thr Pro Ser Gly Asn Gly Tyr Leu Ser Val Tyr
            100                 105                 110
Gly Trp Thr Thr Asp Pro Leu Ile Glu Tyr Tyr Ile Val Glu Ser Tyr
        115                 120                 125
Gly Asp Tyr Asn Pro Gly Ser Gly Thr Tyr Lys Gly Thr Val Thr
    130                 135                 140
Ser Asp Gly Ser Val Tyr Asp Ile Tyr Thr Ala Thr Arg Thr Asn Ala
145                 150                 155                 160
Ala Ser Ile Gln Gly Thr Ala Thr Phe Thr Gln Tyr Trp Ser Val Arg
                165                 170                 175
Gln Asn Lys Arg Val Gly Gly Thr Val Thr Ser Asn His Phe Asn
            180                 185                 190
Ala Trp Ala Lys Leu Gly Met Asn Leu Gly Thr His Asn Tyr Gln Ile
        195                 200                 205
Val Ala Thr Glu Gly Tyr Gln Ser Ser Gly Ser Ser Ser Ile Thr Val
```

Gln
225

<210> SEQ ID NO 37
<211> LENGTH: 221
<212> TYPE: PRT
<213> ORGANISM: Penicillium sp 40

<400> SEQUENCE: 37

Met Lys Ser Phe Ile Ala Tyr Leu Leu Ala Ser Val Ala Val Thr Gly
1               5                   10                  15

Val Met Ala Val Pro Gly Glu Tyr His Lys Arg His Asp Lys Arg Gln
            20                  25                  30

Thr Ile Thr Ser Ser Gln Thr Gly Thr Asn Asn Gly Tyr Tyr Tyr Ser
        35                  40                  45

Phe Trp Thr Asn Gly Gly Gly Thr Val Gln Tyr Thr Asn Gly Ala Ala
    50                  55                  60

Gly Glu Tyr Ser Val Thr Trp Glu Asn Cys Gly Asp Phe Thr Ser Gly
65                  70                  75                  80

Lys Gly Trp Ser Thr Gly Ser Ala Arg Asp Ile Thr Phe Glu Gly Thr
                85                  90                  95

Phe Asn Pro Ser Gly Asn Ala Tyr Leu Ala Val Tyr Gly Trp Thr Thr
            100                 105                 110

Ser Pro Leu Val Glu Tyr Tyr Ile Leu Glu Asp Tyr Gly Asp Tyr Asn
        115                 120                 125

Pro Gly Asn Ser Met Thr Tyr Lys Gly Thr Val Thr Ser Asp Gly Ser
    130                 135                 140

Val Tyr Asp Ile Tyr Glu His Gln Gln Val Asn Gln Pro Ser Ile Ser
145                 150                 155                 160

Gly Thr Ala Thr Phe Asn Gln Tyr Trp Ser Ile Arg Gln Asn Thr Arg
                165                 170                 175

Ser Ser Gly Thr Val Thr Thr Ala Asn His Phe Asn Ala Trp Ala Lys
            180                 185                 190

Leu Gly Met Asn Leu Gly Ser Phe Asn Tyr Gln Ile Val Ser Thr Glu
        195                 200                 205

Gly Tyr Glu Ser Ser Gly Ser Ser Thr Ile Thr Val Ser
    210                 215                 220

<210> SEQ ID NO 38
<211> LENGTH: 240
<212> TYPE: PRT
<213> ORGANISM: Streptomyces sp

<400> SEQUENCE: 38

Met Gln Gln Asp Gly Lys Arg Gln Asp Gln Asn Gln Asn Pro Ala
1               5                   10                  15

Pro Phe Ser Gly Leu Ser Arg Arg Gly Phe Leu Gly Ala Gly Thr
            20                  25                  30

Val Ala Leu Ala Thr Ala Ser Gly Leu Leu Leu Pro Ser Thr Ala His
            35                  40                  45

Ala Ala Thr Thr Ile Thr Thr Asn Gln Thr Gly Tyr Asp Gly Met Tyr
        50                  55                  60

Tyr Ser Phe Trp Thr Asp Gly Gly Ser Val Ser Met Thr Leu Asn
65                  70                  75                  80

Gly Gly Gly Ser Tyr Ser Thr Gln Trp Thr Asn Cys Gly Asn Phe Val

```
                    85                  90                  95
Ala Gly Lys Gly Trp Gly Asn Gly Gly Arg Arg Thr Val Arg Tyr Ser
            100                 105                 110

Gly Tyr Phe Asn Pro Ser Gly Asn Gly Tyr Gly Cys Leu Tyr Gly Trp
        115                 120                 125

Thr Ser Asn Pro Leu Val Glu Tyr Tyr Ile Val Asp Asn Trp Gly Ser
    130                 135                 140

Tyr Arg Pro Thr Gly Glu Tyr Arg Gly Thr Val Tyr Ser Asp Gly Gly
145                 150                 155                 160

Thr Tyr Asp Ile Tyr Lys Thr Thr Arg Tyr Asn Ala Pro Ser Val Glu
                165                 170                 175

Gly Thr Arg Thr Phe Asp Gln Tyr Trp Ser Val Arg Gln Ser Lys Val
            180                 185                 190

Ile Gly Ser Gly Thr Ile Thr Thr Gly Asn His Phe Asp Ala Trp Ala
        195                 200                 205

Arg Ala Gly Met Asn Leu Gly Gln Phe Gln Tyr Tyr Met Ile Met Ala
    210                 215                 220

Thr Glu Gly Tyr Gln Ser Ser Gly Ser Ser Asn Ile Thr Val Ser Gly
225                 230                 235                 240

<210> SEQ ID NO 39
<211> LENGTH: 228
<212> TYPE: PRT
<213> ORGANISM: Streptomyces sp

<400> SEQUENCE: 39

Met Thr Lys Asp Asn Thr Pro Ile Arg Pro Val Ser Arg Arg Gly Phe
1               5                   10                  15

Ile Gly Arg Ala Gly Ala Leu Ala Leu Ala Thr Ser Gly Leu Met Leu
            20                  25                  30

Pro Gly Thr Ala Arg Ala Asp Thr Val Ile Thr Thr Asn Gln Thr Gly
        35                  40                  45

Thr Asn Asn Gly Tyr Tyr Tyr Ser Phe Trp Thr Asp Gly Gly Gly Ser
    50                  55                  60

Val Ser Met Asn Leu Ala Ser Gly Gly Ser Tyr Gly Thr Ser Trp Thr
65                  70                  75                  80

Asn Cys Gly Asn Phe Val Ala Gly Lys Gly Trp Ala Asn Gly Ala Arg
                85                  90                  95

Arg Thr Val Asn Tyr Ser Gly Ser Phe Asn Pro Ser Gly Asn Ala Tyr
            100                 105                 110

Leu Thr Leu Tyr Gly Trp Thr Ala Asn Pro Leu Val Glu Tyr Tyr Ile
        115                 120                 125

Val Asp Asn Trp Gly Thr Tyr Arg Pro Thr Gly Thr Tyr Lys Gly Thr
    130                 135                 140

Val Thr Ser Asp Gly Gly Thr Tyr Asp Val Tyr Gln Thr Thr Arg Val
145                 150                 155                 160

Asn Ala Pro Ser Val Glu Gly Thr Lys Thr Phe Asn Gln Tyr Trp Ser
                165                 170                 175

Val Arg Gln Ser Lys Arg Thr Gly Gly Ser Ile Thr Ala Gly Asn His
            180                 185                 190

Phe Asp Ala Trp Ala Arg Tyr Gly Met Pro Leu Gly Ser Phe Asn Tyr
        195                 200                 205

Tyr Met Ile Met Ala Thr Glu Gly Tyr Gln Ser Ser Gly Ser Ser Ser
    210                 215                 220
```

```
Ile Ser Val Ser
225
```

<210> SEQ ID NO 40
<211> LENGTH: 239
<212> TYPE: PRT
<213> ORGANISM: S. thermocyaneoviolaceus

<400> SEQUENCE: 40

```
Met Asn Thr Leu Val His Pro Gln Gly Arg Ala Gly Gly Leu Arg Leu
1               5                   10                  15

Leu Val Arg Ala Ala Trp Ala Leu Ala Leu Ala Ala Leu Ala Ala Met
            20                  25                  30

Met Phe Gly Gly Thr Ala Arg Ala Asp Thr Ile Thr Ser Asn Gln Thr
        35                  40                  45

Gly Thr His Asn Gly Tyr Phe Tyr Ser Phe Trp Thr Asp Ala Pro Gly
    50                  55                  60

Thr Val Thr Met Asn Thr Gly Ala Gly Gly Asn Tyr Ser Thr Gln Trp
65                  70                  75                  80

Ser Asn Thr Gly Asn Phe Val Ala Gly Lys Gly Trp Ala Thr Gly Gly
                85                  90                  95

Arg Arg Thr Val Thr Tyr Ser Gly Thr Phe Asn Pro Ser Gly Asn Ala
            100                 105                 110

Tyr Leu Ala Leu Tyr Gly Trp Ser Gln Asn Pro Leu Val Glu Tyr Tyr
        115                 120                 125

Ile Val Asp Asn Trp Gly Thr Tyr Arg Pro Thr Gly Thr Tyr Lys Gly
    130                 135                 140

Thr Val Tyr Ser Asp Gly Gly Thr Tyr Asp Ile Tyr Met Thr Thr Arg
145                 150                 155                 160

Tyr Asn Ala Pro Ser Ile Glu Gly Thr Lys Thr Phe Asn Gln Tyr Trp
                165                 170                 175

Ser Val Arg Gln Asn Lys Arg Thr Gly Gly Thr Ile Thr Thr Gly Asn
            180                 185                 190

His Phe Asp Ala Trp Ala Ala His Gly Met Pro Leu Gly Thr Phe Asn
        195                 200                 205

Tyr Met Ile Leu Ala Thr Glu Gly Tyr Gln Ser Ser Gly Ser Ser Asn
    210                 215                 220

Ile Thr Val Gly Asp Ser Gly Gly Asp Asn Gly Gly Gly Gly
225                 230                 235
```

<210> SEQ ID NO 41
<211> LENGTH: 242
<212> TYPE: PRT
<213> ORGANISM: S. viridosporus

<400> SEQUENCE: 41

```
Met Asn Ala Phe Ala His Pro Arg Gly Arg His Gly Arg Ser Ala
1               5                   10                  15

Pro Met Ser Pro Arg Ser Thr Trp Ala Val Leu Leu Ala Ala Leu Ala
            20                  25                  30

Val Met Leu Leu Pro Gly Thr Ala Thr Ala Ala Pro Val Ile Thr Thr
        35                  40                  45

Asn Gln Thr Gly Thr Asn Asn Gly Trp Trp Tyr Ser Phe Trp Thr Asp
    50                  55                  60

Ala Gln Gly Thr Val Ser Met Asp Leu Gly Ser Gly Gly Thr Tyr Ser
65                  70                  75                  80
```

```
Thr Gln Trp Arg Asn Thr Gly Asn Phe Val Ala Gly Lys Gly Trp Ser
                85                  90                  95

Thr Gly Gly Arg Lys Thr Val Asn Tyr Ser Gly Thr Phe Asn Pro Ser
            100                 105                 110

Gly Asn Ala Tyr Leu Thr Leu Tyr Gly Trp Thr Thr Gly Pro Leu Ile
        115                 120                 125

Glu Tyr Tyr Ile Val Asp Asn Trp Gly Thr Tyr Arg Pro Thr Gly Lys
    130                 135                 140

Tyr Lys Gly Thr Val Thr Ser Asp Gly Gly Thr Tyr Asp Ile Tyr Lys
145                 150                 155                 160

Thr Thr Arg Tyr Asn Ala Pro Ser Ile Glu Gly Thr Lys Thr Phe Asp
                165                 170                 175

Gln Tyr Trp Ser Val Arg Gln Ser Lys Arg Thr Gly Gly Thr Ile Thr
            180                 185                 190

Ser Gly Asn His Phe Asp Ala Trp Ala Arg Asn Gly Met Asn Leu Gly
        195                 200                 205

Asn His Asn Tyr Met Ile Met Ala Thr Glu Gly Tyr Gln Ser Ser Gly
    210                 215                 220

Ser Ser Thr Ile Thr Val Ser Glu Ser Gly Ser Gly Gly Gly Gly Gly
225                 230                 235                 240

Gly Gly

<210> SEQ ID NO 42
<211> LENGTH: 240
<212> TYPE: PRT
<213> ORGANISM: T. fusca

<400> SEQUENCE: 42

Met Asn His Ala Pro Ala Ser Leu Lys Ser Arg Arg Arg Phe Arg Pro
1               5                   10                  15

Arg Leu Leu Ile Gly Lys Ala Phe Ala Ala Leu Val Ala Val Val
            20                  25                  30

Thr Met Ile Pro Ser Thr Ala Ala His Ala Ala Val Thr Ser Asn Glu
        35                  40                  45

Thr Gly Tyr His Asp Gly Tyr Phe Tyr Ser Phe Trp Thr Asp Ala Pro
    50                  55                  60

Gly Thr Val Ser Met Glu Leu Gly Pro Gly Gly Asn Tyr Ser Thr Ser
65                  70                  75                  80

Trp Arg Asn Thr Gly Asn Phe Val Ala Gly Lys Gly Trp Ala Thr Gly
                85                  90                  95

Gly Arg Arg Thr Val Thr Tyr Ser Ala Ser Phe Asn Pro Ser Gly Asn
            100                 105                 110

Ala Tyr Leu Thr Leu Tyr Gly Trp Thr Arg Asn Pro Leu Val Glu Tyr
        115                 120                 125

Tyr Ile Val Glu Ser Trp Gly Thr Tyr Arg Pro Thr Gly Thr Tyr Met
    130                 135                 140

Gly Thr Val Thr Thr Asp Gly Gly Thr Tyr Asp Ile Tyr Lys Thr Thr
145                 150                 155                 160

Arg Tyr Asn Ala Pro Ser Ile Glu Gly Thr Arg Thr Phe Asp Gln Tyr
                165                 170                 175

Trp Ser Val Arg Gln Ser Lys Arg Thr Ser Gly Thr Ile Thr Ala Gly
            180                 185                 190

Asn His Phe Asp Ala Trp Ala Arg His Gly Met His Leu Gly Thr His
        195                 200                 205
```

```
Asp Tyr Met Ile Met Ala Thr Glu Gly Tyr Gln Ser Ser Gly Ser Ser
            210                 215                 220

Asn Val Thr Leu Gly Thr Ser Gly Gly Gly Asn Pro Gly Gly Gly Asn
225                 230                 235                 240

<210> SEQ ID NO 43
<211> LENGTH: 241
<212> TYPE: PRT
<213> ORGANISM: C. pachnodae

<400> SEQUENCE: 43

Met Thr Arg Thr Ile Ser Arg Ala Ala His Arg Pro Ala Gly Gly
1               5                   10                  15

Arg Ile Ala Arg Ala Leu Ala Ala Ala Gly Ala Thr Val Ala Met Val
                20                  25                  30

Ile Ala Gly Val Ala Ala Ala Gln Pro Ala Ala Ala Val Asp Ser Asn
                35                  40                  45

Ser Thr Gly Ser Ser Gly Gly Tyr Phe Tyr Ser Phe Trp Thr Asp Ala
        50                  55                  60

Pro Gly Thr Val Ser Met Asn Leu Gly Ser Gly Gly Asn Tyr Ser Thr
65                  70                  75                  80

Ser Trp Ser Asn Thr Gly Asn Phe Val Ala Gly Lys Gly Trp Ser Thr
                85                  90                  95

Gly Ser Ala Arg Thr Ile Ser Tyr Ser Gly Thr Phe Asn Pro Ser Gly
                100                 105                 110

Asn Ala Tyr Leu Ala Val Tyr Gly Trp Ser His Asp Pro Leu Val Glu
            115                 120                 125

Tyr Tyr Ile Val Asp Ser Trp Gly Thr Tyr Arg Pro Thr Gly Thr Phe
130                 135                 140

Met Gly Thr Val Asn Ser Asp Gly Gly Thr Tyr Asp Ile Tyr Lys Thr
145                 150                 155                 160

Thr Arg Thr Asn Ala Pro Ser Ile Glu Gly Thr Ala Thr Phe Thr Gln
                165                 170                 175

Tyr Trp Ser Val Arg Gln Ser Lys Arg Val Gly Gly Thr Ile Thr Thr
            180                 185                 190

Ala Asn His Phe Asn Ala Trp Ala Ser His Gly Met Asn Leu Gly Arg
        195                 200                 205

His Asp Tyr Gln Ile Leu Ala Thr Glu Gly Tyr Gln Ser Ser Gly Ser
    210                 215                 220

Ser Asn Ile Thr Ile Gly Ser Thr Ser Gly Gly Gly Ser Gly Gly
225                 230                 235                 240

Gly

<210> SEQ ID NO 44
<211> LENGTH: 221
<212> TYPE: PRT
<213> ORGANISM: A. oryzae

<400> SEQUENCE: 44

Met Val Ser Phe Ser Ser Leu Leu Leu Ala Val Ser Ala Val Ser Gly
1               5                   10                  15

Ala Leu Ala Ala Pro Gly Asp Ser Thr Leu Val Glu Leu Ala Lys Arg
                20                  25                  30

Ala Ile Thr Ser Ser Glu Thr Gly Thr Asn Asn Gly Tyr Tyr Tyr Ser
            35                  40                  45

Phe Trp Thr Asn Gly Gly Gly Asp Val Glu Tyr Thr Asn Gly Asn Gly
```

-continued

```
    50                  55                  60

Gly Gln Tyr Ser Val Lys Trp Thr Asn Cys Asp Asn Phe Val Ala Gly
65                  70                  75                  80

Lys Gly Trp Asn Pro Gly Ser Ala Lys Thr Val Thr Tyr Ser Gly Glu
                85                  90                  95

Trp Glu Ser Asn Ser Asn Ser Tyr Val Ser Leu Tyr Gly Trp Thr Gln
            100                 105                 110

Asn Pro Leu Val Glu Tyr Tyr Ile Val Asp Lys Tyr Gly Asp Tyr Asp
        115                 120                 125

Pro Ser Thr Gly Ala Thr Glu Leu Gly Thr Val Glu Ser Asp Gly Gly
    130                 135                 140

Thr Tyr Lys Ile Tyr Lys Thr Thr Arg Glu Asn Ala Pro Ser Ile Glu
145                 150                 155                 160

Gly Thr Ser Thr Phe Asn Gln Tyr Trp Ser Val Arg Gln Ser Gly Arg
                165                 170                 175

Val Gly Gly Thr Ile Thr Ala Gln Asn His Phe Asp Ala Trp Ala Asn
            180                 185                 190

Val Gly Leu Gln Leu Gly Thr His Asn Tyr Met Ile Leu Ala Thr Glu
        195                 200                 205

Gly Tyr Lys Ser Ser Gly Ser Ala Thr Ile Thr Val Glu
    210                 215                 220

<210> SEQ ID NO 45
<211> LENGTH: 216
<212> TYPE: PRT
<213> ORGANISM: C. purpurea

<400> SEQUENCE: 45

Met Phe Leu Thr Ser Val Val Ser Leu Val Val Gly Ala Ile Ser Cys
1               5                   10                  15

Val Ser Ala Ala Pro Ala Ala Ala Ser Glu Leu Met Gln Met Thr Pro
            20                  25                  30

Arg Asn Ser Cys Tyr Gly Gly Gly Leu Tyr Ser Ser Tyr Trp Ala Asp
        35                  40                  45

Tyr Gly Asn Thr Arg Tyr Ser Cys Gly Ala Gly Gly His Tyr Asp Leu
    50                  55                  60

Ser Trp Gly Asn Gly Gly Asn Val Val Ala Gly Arg Gly Trp Lys Pro
65                  70                  75                  80

Ala Ser Pro Arg Ala Val Thr Tyr Ser Gly Ser Trp Gln Cys Asn Gly
                85                  90                  95

Asn Cys Tyr Leu Ser Val Tyr Gly Trp Thr Ile Asn Pro Leu Val Glu
            100                 105                 110

Tyr Tyr Ile Val Glu Asn Tyr Gly Asn Tyr Asn Pro Ser Ala Gly Ala
        115                 120                 125

Gln Arg Arg Gly Gln Val Thr Ala Asp Gly Ser Ile Tyr Asp Ile Tyr
    130                 135                 140

Ile Ser Thr Gln His Asn Gln Pro Ser Ile Leu Gly Thr Asn Thr Phe
145                 150                 155                 160

His Gln Tyr Trp Ser Ile Arg Arg Asn Lys Arg Val Gly Gly Thr Val
                165                 170                 175

Ser Thr Gly Val His Phe Asn Ala Trp Arg Ser Leu Gly Met Pro Leu
            180                 185                 190

Gly Thr Tyr Asp Tyr Met Ile Val Ala Thr Glu Gly Phe Arg Ser Ser
        195                 200                 205
```

```
Gly Ser Ala Ser Ile Thr Val Ser
    210                 215

<210> SEQ ID NO 46
<211> LENGTH: 236
<212> TYPE: PRT
<213> ORGANISM: C. mixtus

<400> SEQUENCE: 46

Met Lys Phe Pro Leu Ile Gly Lys Ser Thr Leu Ala Ala Leu Phe Cys
1               5                   10                  15

Ser Ala Leu Leu Gly Val Asn Asn Thr Gln Ala Gln Thr Leu Thr Asn
            20                  25                  30

Asn Ala Thr Gly Thr His Asn Gly Phe Tyr Tyr Thr Phe Trp Lys Asp
        35                  40                  45

Ser Gly Asp Ala Ser Met Gly Leu Gln Ala Gly Gly Arg Tyr Thr Ser
    50                  55                  60

Gln Trp Ser Asn Gly Thr Asn Asn Trp Val Gly Lys Gly Trp Asn
65                  70                  75                  80

Pro Gly Gly Pro Lys Val Val Thr Tyr Ser Gly Ser Tyr Asn Val Asp
                85                  90                  95

Asn Ser Gln Asn Ser Tyr Leu Ala Leu Tyr Gly Trp Thr Arg Ser Pro
            100                 105                 110

Leu Ile Glu Tyr Tyr Val Ile Glu Ser Tyr Gly Ser Tyr Asn Pro Ala
        115                 120                 125

Ser Cys Ser Gly Gly Thr Asp Tyr Gly Ser Phe Gln Ser Asp Gly Ala
    130                 135                 140

Thr Tyr Asn Val Arg Arg Cys Gln Arg Val Gln Gln Pro Ser Ile Asp
145                 150                 155                 160

Gly Thr Gln Thr Phe Tyr Gln Tyr Phe Ser Val Arg Ser Pro Lys Lys
                165                 170                 175

Gly Phe Gly Gln Ile Ser Gly Thr Ile Thr Thr Ala Asn His Phe Asn
            180                 185                 190

Phe Trp Ala Ser Lys Gly Leu Asn Leu Gly Asn His Asp Tyr Met Val
        195                 200                 205

Leu Ala Thr Glu Gly Tyr Gln Ser Arg Gly Ser Ser Asp Ile Thr Val
    210                 215                 220

Ser Glu Gly Thr Gly Gly Thr Thr Ser Ser Ser Val
225                 230                 235

<210> SEQ ID NO 47
<211> LENGTH: 237
<212> TYPE: PRT
<213> ORGANISM: P. fluorescens cellulosa

<400> SEQUENCE: 47

Met Lys Leu Pro Thr Leu Gly Lys Cys Val Val Arg Thr Leu Met Gly
1               5                   10                  15

Ala Val Ala Leu Gly Ala Ile Ser Val Asn Ala Gln Thr Leu Ser Ser
            20                  25                  30

Asn Ser Thr Gly Thr Asn Asn Gly Phe Tyr Tyr Thr Phe Trp Lys Asp
        35                  40                  45

Ser Gly Asp Ala Ser Met Thr Leu Leu Ser Gly Gly Arg Tyr Gln Ser
    50                  55                  60

Ser Trp Gly Asn Ser Thr Asn Asn Trp Val Gly Gly Lys Gly Trp Asn
65                  70                  75                  80
```

```
Pro Gly Asn Asn Ser Arg Val Ile Ser Tyr Ser Gly Ser Tyr Gly Val
                85                  90                  95

Asp Ser Ser Gln Asn Ser Tyr Leu Ala Leu Tyr Gly Trp Thr Arg Ser
            100                 105                 110

Pro Leu Ile Glu Tyr Tyr Val Ile Glu Ser Tyr Gly Ser Tyr Asn Pro
        115                 120                 125

Ala Ser Cys Ser Gly Gly Thr Asp Tyr Gly Ser Phe Gln Ser Asp Gly
130                 135                 140

Ala Thr Tyr Asn Val Arg Arg Cys Gln Arg Val Asn Gln Pro Ser Ile
145                 150                 155                 160

Asp Gly Thr Gln Thr Phe Tyr Gln Tyr Phe Ser Val Arg Asn Pro Lys
                165                 170                 175

Lys Gly Phe Gly Asn Ile Ser Gly Thr Ile Thr Phe Ala Asn His Val
            180                 185                 190

Asn Phe Trp Ala Ser Lys Gly Leu Asn Leu Gly Asn His Asn Tyr Gln
        195                 200                 205

Val Leu Ala Thr Glu Gly Tyr Gln Ser Arg Gly Ser Ser Asp Ile Thr
210                 215                 220

Val Ser Glu Gly Thr Ser Gly Gly Thr Ser Ser Val
225                 230                 235

<210> SEQ ID NO 48
<211> LENGTH: 217
<212> TYPE: PRT
<213> ORGANISM: P. cochleariae

<400> SEQUENCE: 48

Met Gln Phe Leu Ile Pro Val Val Ile Leu Cys Val Ser Leu Val Asp
1               5                   10                  15

Ser Gln Lys Val Leu Tyr Asn Asn Glu Ile Gly Phe Asn Asn Gly Phe
            20                  25                  30

Tyr Tyr Ala Phe Trp Lys Asp Ser Gly Ser Ala Thr Phe Thr Leu Glu
        35                  40                  45

Ser Gly Gly Arg Tyr Ala Gly Asn Trp Thr Thr Ser Thr Asn Asn Trp
    50                  55                  60

Val Gly Gly Lys Gly Trp Asn Pro Gly Asn Ser Trp Arg Thr Val Asn
65                  70                  75                  80

Tyr Ser Gly Tyr Tyr Gly Ile Asn Glu Tyr Ala Asn Ser Tyr Leu Ser
                85                  90                  95

Leu Tyr Gly Trp Thr Thr Asn Pro Leu Ile Glu Tyr Tyr Val Val Glu
            100                 105                 110

Ser Tyr Gly Ser Tyr Ser Pro Leu Asn Cys Pro Gly Gly Thr Asp Glu
        115                 120                 125

Gly Ser Phe Thr Ser Gly Gly Ala Thr Tyr Gln Val Arg Lys Cys Arg
130                 135                 140

Arg Thr Asn Ala Pro Ser Ile Ile Gly Thr Gln Ser Phe Asp Gln Tyr
145                 150                 155                 160

Phe Ser Val Arg Thr Pro Lys Lys Gly Phe Gly Gln Val Ser Gly Ser
                165                 170                 175

Val Asn Phe Ala Asp His Val Gln Tyr Trp Ala Ser Lys Gly Leu Pro
            180                 185                 190

Leu Gly Thr His Ala His Gln Ile Phe Ala Thr Glu Gly Tyr Gln Ser
        195                 200                 205

Ser Gly Phe Ala Asp Ile Thr Val Ser
210                 215
```

<210> SEQ ID NO 49
<211> LENGTH: 182
<212> TYPE: PRT
<213> ORGANISM: A. kawachi

<400> SEQUENCE: 49

```
Ala Gly Ile Asn Tyr Val Gln Asn Tyr Asn Gly Asn Leu Gly Asp Phe
1               5                   10                  15

Thr Tyr Asp Glu Ser Ala Gly Thr Phe Ser Met Tyr Trp Glu Asp Gly
            20                  25                  30

Val Ser Ser Asp Phe Val Val Gly Leu Gly Trp Thr Thr Gly Ser Ser
        35                  40                  45

Asn Ala Ile Thr Tyr Ser Ala Glu Tyr Ser Ala Ser Gly Ser Ser Ser
    50                  55                  60

Tyr Leu Ala Val Tyr Gly Trp Val Asn Tyr Pro Gln Ala Glu Tyr Tyr
65                  70                  75                  80

Ile Val Glu Asp Tyr Gly Asp Tyr Asn Pro Cys Ser Ser Ala Thr Ser
                85                  90                  95

Leu Gly Thr Val Tyr Ser Asp Gly Ser Thr Tyr Gln Val Cys Thr Asp
            100                 105                 110

Thr Arg Thr Asn Glu Pro Ser Ile Thr Gly Thr Ser Thr Phe Thr Gln
        115                 120                 125

Tyr Phe Ser Val Arg Glu Ser Thr Arg Thr Ser Gly Thr Val Thr Val
    130                 135                 140

Ala Asn His Phe Asn Phe Trp Ala Gln His Gly Phe Gly Asn Ser Asp
145                 150                 155                 160

Phe Asn Tyr Gln Val Met Ala Val Glu Ala Trp Ser Gly Ala Gly Ser
                165                 170                 175

Ala Ser Val Thr Ile Ser
            180
```

<210> SEQ ID NO 50
<211> LENGTH: 211
<212> TYPE: PRT
<213> ORGANISM: A. niger

<400> SEQUENCE: 50

```
Met Lys Val Thr Ala Ala Phe Ala Gly Leu Leu Val Thr Ala Phe Ala
1               5                   10                  15

Ala Pro Val Pro Glu Pro Val Leu Val Ser Arg Ser Ala Gly Ile Asn
            20                  25                  30

Tyr Val Gln Asn Tyr Asn Gly Asn Leu Gly Asp Phe Thr Tyr Asp Glu
        35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Lys Ala Ile Thr
65                  70                  75                  80

Tyr Ser Ala Glu Tyr Ser Ala Ser Gly Ser Ser Tyr Leu Ala Val
                85                  90                  95

Tyr Gly Trp Val Asn Tyr Pro Gln Ala Glu Tyr Tyr Ile Val Glu Asp
            100                 105                 110

Tyr Gly Asp Tyr Asn Pro Cys Ser Ser Ala Thr Ser Leu Gly Thr Val
        115                 120                 125

Tyr Ser Asp Gly Ser Thr Tyr Gln Val Cys Thr Asp Thr Arg Thr Asn
    130                 135                 140
```

```
Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala Gln His Gly Phe Gly Asn Ser Asp Phe Asn Tyr Gln
            180                 185                 190

Val Met Ala Val Glu Ala Trp Ser Gly Ala Gly Ser Ala Ser Val Thr
        195                 200                 205

Ile Ser Ser
    210
```

<210> SEQ ID NO 51
<211> LENGTH: 210
<212> TYPE: PRT
<213> ORGANISM: A .tubigensis

<400> SEQUENCE: 51

```
Met Lys Val Thr Ala Ala Phe Ala Gly Leu Leu Val Thr Ala Phe Ala
1               5                   10                  15

Ala Pro Ala Pro Glu Pro Asp Leu Val Ser Arg Ser Ala Gly Ile Asn
            20                  25                  30

Tyr Val Gln Asn Tyr Asn Gly Asn Leu Gly Asp Phe Thr Tyr Asp Glu
        35                  40                  45

Ser Ala Gly Thr Phe Ser Met Tyr Trp Glu Asp Gly Val Ser Ser Asp
    50                  55                  60

Phe Val Val Gly Leu Gly Trp Thr Thr Gly Ser Ser Thr Ile Thr Tyr
65                  70                  75                  80

Ser Ala Glu Tyr Ser Ala Ser Gly Ser Ala Ser Tyr Leu Ala Val Tyr
                85                  90                  95

Gly Trp Val Asn Tyr Pro Gln Ala Glu Tyr Tyr Ile Val Glu Asp Tyr
            100                 105                 110

Gly Asp Tyr Asn Pro Cys Ser Ser Ala Thr Ser Leu Gly Thr Val Tyr
        115                 120                 125

Ser Asp Gly Ser Thr Tyr Gln Val Cys Thr Asp Thr Arg Thr Asn Glu
    130                 135                 140

Pro Ser Ile Thr Gly Thr Ser Thr Phe Thr Gln Tyr Phe Ser Val Arg
145                 150                 155                 160

Glu Ser Thr Arg Thr Ser Gly Thr Val Thr Val Ala Asn His Phe Asn
                165                 170                 175

Phe Trp Ala His His Gly Phe Gly Asn Ser Asp Phe Asn Tyr Gln Val
            180                 185                 190

Val Ala Val Glu Ala Trp Ser Gly Ala Gly Ser Ala Ser Val Thr Ile
        195                 200                 205

Ser Ser
    210
```

<210> SEQ ID NO 52
<211> LENGTH: 208
<212> TYPE: PRT
<213> ORGANISM: P. purpurogenum

<400> SEQUENCE: 52

```
Met Lys Val Thr Ala Ala Phe Ala Gly Leu Leu Ala Arg His Ser Pro
1               5                   10                  15

Pro Leu Ser Thr Glu Leu Val Thr Arg Ser Ile Asn Tyr Val Gln Asn
            20                  25                  30
```

```
Tyr Asn Gly Asn Leu Gly Ala Phe Ser Tyr Asn Glu Gly Ala Gly Thr
            35                  40                  45

Phe Ser Met Tyr Trp Gln Gln Gly Val Ser Asn Asp Phe Val Val Gly
    50                  55                  60

Leu Gly Arg Ser Thr Gly Ser Ser Asn Pro Ile Thr Tyr Ser Ala Ser
 65                  70                  75                  80

Tyr Ser Ala Ser Gly Gly Ser Tyr Leu Ala Val Tyr Gly Trp Val Asn
                85                  90                  95

Ser Pro Gln Ala Glu Tyr Tyr Val Val Glu Ala Tyr Gly Asn Tyr Asn
                100                 105                 110

Pro Cys Ser Ser Gly Ser Ala Thr Asn Leu Gly Thr Val Ser Ser Asp
            115                 120                 125

Gly Gly Thr Tyr Gln Val Cys Thr Asp Thr Arg Val Asn Gln Pro Ser
        130                 135                 140

Ile Thr Gly Thr Ser Thr Phe Thr Gln Phe Phe Ser Val Arg Gln Gly
145                 150                 155                 160

Ser Arg Thr Ser Gly Thr Val Thr Ile Ala Asn His Phe Asn Phe Trp
                165                 170                 175

Ala Asn Asp Gly Phe Gly Asn Ser Asn Phe Asn Tyr Gln Val Val Ala
            180                 185                 190

Val Glu Ala Trp Ser Gly Thr Gly Thr Ala Ser Val Thr Val Ser Ala
        195                 200                 205

<210> SEQ ID NO 53
<211> LENGTH: 233
<212> TYPE: PRT
<213> ORGANISM: P. purpurogenum

<400> SEQUENCE: 53

Met Lys Val Thr Ala Ala Phe Ala Gly Leu Leu Ala Arg His Ser Pro
1               5                   10                  15

Pro Leu Ser Thr Glu Leu Val Thr Arg Ser Ile Asn Tyr Val Gln Asn
            20                  25                  30

Tyr Asn Gly Asn Leu Gly Ala Phe Ser Tyr Asn Glu Gly Ala Gly Thr
            35                  40                  45

Phe Ser Met Tyr Trp Gln Gln Gly Val Ser Asn Asp Phe Val Val Gly
    50                  55                  60

Leu Gly Arg Ser Thr Gly Ser Ser Asn Pro Ile Thr Tyr Ser Ala Ser
 65                  70                  75                  80

Tyr Ser Ala Ser Gly Gly Ser Tyr Leu Ala Val Tyr Gly Trp Val Asn
                85                  90                  95

Ser Pro Gln Ala Glu Tyr Tyr Val Val Glu Ala Tyr Gly Asn Tyr Asn
                100                 105                 110

Pro Cys Ser Ser Gly Ser Ala Thr Asn Leu Gly Thr Val Ser Ser Asp
            115                 120                 125

Gly Gly Thr Tyr Gln Val Cys Thr Asp Thr Arg Val Asn Gln Pro Ser
        130                 135                 140

Ile Thr Gly Thr Ser Thr Phe Thr Gln Phe Phe Ser Val Arg Gln Gly
145                 150                 155                 160

Ser Arg Thr Ser Gly Thr Val Thr Ile Ala Asn His Phe Asn Phe Trp
                165                 170                 175

Ala Asn Asp Gly Phe Gly Asn Ser Asn Phe Asn Tyr Gln Val Val Ala
            180                 185                 190

Val Glu Ala Trp Ser Gly Thr Gly Thr Ala Ser Val Thr Val Ser Ala
```

```
                195                 200                 205
Asn Phe Asn Tyr Gln Val Leu Ala Val Glu Gly Phe Ser Gly Ser Gly
        210                 215                 220

Asn Ala Asn Met Lys Leu Ile Ser Gly
225                 230

<210> SEQ ID NO 54
<211> LENGTH: 229
<212> TYPE: PRT
<213> ORGANISM: T. reesei

<400> SEQUENCE: 54

Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
        35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser
                85                  90                  95

Ala Pro Ile Asn Phe Gly Gly Ser Phe Ser Val Asn Ser Gly Thr Gly
            100                 105                 110

Leu Leu Ser Val Tyr Gly Trp Ser Thr Asn Pro Leu Val Glu Tyr Tyr
        115                 120                 125

Ile Met Glu Asp Asn His Asn Tyr Pro Ala Gln Gly Thr Val Lys Gly
    130                 135                 140

Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
            180                 185                 190

His Phe Asn Ala Trp Ala Ser Leu Gly Leu His Leu Gly Gln Met Asn
        195                 200                 205

Tyr Gln Val Val Ala Val Glu Gly Trp Gly Gly Ser Gly Ser Ala Ser
    210                 215                 220

Gln Ser Val Ser Asn
225

<210> SEQ ID NO 55
<211> LENGTH: 227
<212> TYPE: PRT
<213> ORGANISM: B. pumilus

<400> SEQUENCE: 55

Met Asn Leu Lys Arg Leu Arg Leu Leu Phe Val Met Cys Ile Gly Phe
1               5                   10                  15

Val Leu Thr Leu Thr Ala Val Pro Ala His Ala Glu Thr Ile Tyr Asp
            20                  25                  30

Asn Arg Ile Gly Thr His Ser Gly Tyr Asp Phe Glu Leu Trp Lys Asp
        35                  40                  45

Tyr Gly Asn Thr Ser Met Thr Leu Asn Asn Gly Gly Ala Phe Ser Ala
```

```
                    50                  55                  60
Ser Trp Asn Asn Ile Gly Asn Ala Leu Phe Arg Lys Gly Lys Lys Phe
 65                  70                  75                  80

Asp Ser Thr Lys Thr His His Gln Leu Gly Asn Ile Ser Ile Asn Tyr
                 85                  90                  95

Asn Ala Ala Phe Asn Pro Gly Gly Asn Ser Tyr Leu Cys Val Tyr Gly
                100                 105                 110

Trp Thr Gln Ser Pro Leu Ala Glu Tyr Tyr Ile Val Glu Ser Trp Gly
                115                 120                 125

Thr Tyr Arg Pro Thr Gly Thr Tyr Lys Gly Ser Phe Tyr Ala Asp Gly
            130                 135                 140

Gly Thr Tyr Asp Ile Tyr Glu Thr Leu Arg Val Asn Gln Pro Ser Ile
145                 150                 155                 160

Ile Gly Asp Ala Thr Phe Lys Gln Tyr Trp Ser Val Arg Gln Thr Lys
                165                 170                 175

Arg Thr Ser Gly Thr Ala Ser Val Ser Glu His Phe Lys Lys Trp Glu
                180                 185                 190

Ser Leu Gly Met Pro Met Gly Lys Met Tyr Glu Thr Ala Leu Thr Val
            195                 200                 205

Glu Gly Tyr Arg Ser Asn Gly Ser Ala Asn Val Met Thr Asn Gln Leu
        210                 215                 220

Met Ile Arg
225

<210> SEQ ID NO 56
<211> LENGTH: 228
<212> TYPE: PRT
<213> ORGANISM: B. pumilus

<400> SEQUENCE: 56

Met Asn Leu Arg Lys Leu Arg Leu Leu Phe Val Met Cys Ile Gly Leu
 1               5                  10                  15

Thr Leu Ile Leu Thr Ala Val Pro Ala His Ala Arg Thr Ile Thr Asn
                 20                  25                  30

Asn Glu Met Gly Asn His Ser Gly Tyr Asp Tyr Glu Leu Trp Lys Asp
             35                  40                  45

Tyr Gly Asn Thr Ser Met Thr Leu Asn Asn Gly Gly Ala Phe Ser Ala
         50                  55                  60

Gly Trp Asn Asn Ile Gly Asn Ala Leu Phe Arg Lys Gly Lys Lys Phe
 65                  70                  75                  80

Asp Ser Thr Arg Thr His His Gln Leu Gly Asn Ile Ser Ile Asn Tyr
                 85                  90                  95

Asn Ala Ser Phe Asn Pro Gly Gly Asn Ser Tyr Leu Cys Val Tyr Gly
                100                 105                 110

Trp Thr Gln Ser Pro Leu Ala Glu Tyr Tyr Ile Val Asp Ser Trp Gly
                115                 120                 125

Thr Tyr Arg Pro Thr Gly Ala Tyr Lys Gly Ser Phe Tyr Ala Asp Gly
            130                 135                 140

Gly Thr Tyr Asp Ile Tyr Glu Thr Thr Arg Val Asn Gln Pro Ser Ile
145                 150                 155                 160

Ile Gly Ile Ala Thr Phe Lys Gln Tyr Trp Ser Val Arg Gln Thr Lys
                165                 170                 175

Arg Thr Ser Gly Thr Val Ser Val Ser Ala His Phe Arg Lys Trp Glu
                180                 185                 190
```

```
Ser Leu Gly Met Pro Met Gly Lys Met Tyr Glu Thr Ala Phe Thr Val
        195                 200                 205

Glu Gly Tyr Gln Ser Ser Gly Ser Ala Asn Val Met Thr Asn Gln Leu
    210                 215                 220

Phe Ile Gly Asn
225

<210> SEQ ID NO 57
<211> LENGTH: 261
<212> TYPE: PRT
<213> ORGANISM: C. acetobutylicum

<400> SEQUENCE: 57

Met Leu Arg Arg Lys Val Ile Phe Thr Val Leu Ala Thr Leu Val Met
1               5                   10                  15

Thr Ser Leu Thr Ile Val Asp Asn Thr Ala Phe Ala Ala Thr Asn Leu
            20                  25                  30

Asn Thr Thr Glu Ser Thr Phe Ser Lys Glu Val Leu Ser Thr Gln Lys
        35                  40                  45

Thr Tyr Ser Ala Phe Asn Thr Gln Ala Ala Pro Lys Thr Ile Thr Ser
    50                  55                  60

Asn Glu Ile Gly Val Asn Gly Gly Tyr Asp Tyr Glu Leu Trp Lys Asp
65                  70                  75                  80

Tyr Gly Asn Thr Ser Met Thr Leu Lys Asn Gly Gly Ala Phe Ser Cys
                85                  90                  95

Gln Trp Ser Asn Ile Gly Asn Ala Leu Phe Arg Lys Gly Lys Lys Phe
            100                 105                 110

Asn Asp Thr Gln Thr Tyr Lys Gln Leu Gly Asn Ile Ser Val Asn Tyr
        115                 120                 125

Asp Cys Asn Tyr Gln Pro Tyr Gly Asn Ser Tyr Leu Cys Val Tyr Gly
    130                 135                 140

Trp Thr Ser Ser Pro Leu Val Glu Tyr Tyr Ile Val Asp Ser Trp Gly
145                 150                 155                 160

Ser Trp Arg Pro Pro Gly Gly Thr Ser Lys Gly Thr Ile Thr Val Asp
                165                 170                 175

Gly Gly Ile Tyr Asp Ile Tyr Glu Thr Thr Arg Ile Asn Gln Pro Ser
            180                 185                 190

Ile Gln Gly Asn Thr Thr Phe Lys Gln Tyr Trp Ser Val Arg Arg Thr
        195                 200                 205

Lys Arg Thr Ser Gly Thr Ile Ser Val Ser Lys His Phe Ala Ala Trp
    210                 215                 220

Glu Ser Lys Gly Met Pro Leu Gly Lys Met His Glu Thr Ala Phe Asn
225                 230                 235                 240

Ile Glu Gly Tyr Gln Ser Ser Gly Lys Ala Asp Val Asn Ser Met Ser
                245                 250                 255

Ile Asn Ile Gly Lys
            260

<210> SEQ ID NO 58
<211> LENGTH: 234
<212> TYPE: PRT
<213> ORGANISM: C. thermocellum

<400> SEQUENCE: 58

Met Lys Gln Lys Leu Leu Val Thr Phe Leu Ile Leu Ile Thr Phe Thr
1               5                   10                  15
```

Val Ser Leu Thr Leu Phe Pro Val Asn Val Arg Ala Asp Val Ile
            20                  25                  30

Thr Ser Asn Gln Thr Gly Thr Gly Gly Tyr Asn Phe Glu Tyr Trp
        35                  40                  45

Lys Asp Thr Gly Asn Gly Thr Met Val Leu Lys Asp Gly Gly Ala Phe
50                  55                  60

Ser Cys Glu Trp Ser Asn Ile Asn Asn Ile Leu Phe Arg Lys Gly Phe
65                  70                  75                  80

Lys Tyr Asp Glu Thr Lys Thr His Asp Gln Leu Gly Tyr Ile Thr Val
                85                  90                  95

Thr Tyr Ser Cys Asn Tyr Gln Pro Asn Gly Asn Ser Tyr Leu Gly Val
            100                 105                 110

Tyr Gly Trp Thr Ser Asn Pro Leu Val Glu Tyr Ile Ile Glu Ser
        115                 120                 125

Trp Gly Thr Trp Arg Pro Pro Gly Ala Thr Pro Lys Gly Thr Ile Thr
130                 135                 140

Val Asp Gly Gly Thr Tyr Glu Ile Tyr Glu Thr Thr Arg Val Asn Gln
145                 150                 155                 160

Pro Ser Ile Lys Gly Thr Ala Thr Phe Gln Gln Tyr Trp Ser Val Arg
                165                 170                 175

Thr Ser Lys Arg Thr Ser Gly Thr Ile Ser Val Thr Glu His Phe Lys
            180                 185                 190

Ala Trp Glu Arg Leu Gly Met Lys Met Gly Lys Met Tyr Glu Val Ala
        195                 200                 205

Leu Val Val Glu Gly Tyr Gln Ser Ser Gly Lys Ala Asp Val Thr Ser
    210                 215                 220

Met Thr Ile Thr Val Gly Asn Ala Pro Ser
225                 230

<210> SEQ ID NO 59
<211> LENGTH: 230
<212> TYPE: PRT
<213> ORGANISM: Bacillus sp 41M-1

<400> SEQUENCE: 59

Met Lys Gln Val Lys Ile Met Phe Leu Met Thr Met Phe Leu Gly Ile
1               5                   10                  15

Gly Leu Leu Phe Phe Ser Glu Asn Ala Glu Ala Ile Thr Ser Asn
            20                  25                  30

Glu Ile Gly Thr His Asp Gly Tyr Asp Tyr Glu Phe Trp Lys Asp Ser
        35                  40                  45

Gly Gly Ser Gly Ser Met Thr Leu Asn Ser Gly Gly Thr Phe Ser Ala
    50                  55                  60

Gln Trp Ser Asn Val Asn Asn Ile Leu Phe Arg Lys Gly Lys Lys Phe
65                  70                  75                  80

Asp Glu Thr Gln Thr His Gln Gln Ile Gly Asn Met Ser Ile Asn Tyr
                85                  90                  95

Gly Ala Thr Tyr Asn Pro Asn Gly Asn Ser Tyr Leu Thr Val Tyr Gly
            100                 105                 110

Trp Thr Val Asp Pro Leu Val Glu Phe Tyr Ile Val Asp Ser Trp Gly
        115                 120                 125

Thr Trp Arg Pro Pro Gly Gly Thr Pro Lys Gly Thr Ile Asn Val Asp
130                 135                 140

Gly Gly Thr Tyr Gln Ile Tyr Glu Thr Thr Arg Tyr Asn Gln Pro Ser
145                 150                 155                 160

```
Ile Lys Gly Thr Ala Thr Phe Gln Gln Tyr Trp Ser Val Arg Thr Ser
                165                 170                 175

Lys Arg Thr Ser Gly Thr Ile Ser Val Ser Glu His Phe Arg Ala Trp
            180                 185                 190

Glu Ser Leu Gly Met Asn Met Gly Asn Met Tyr Glu Val Ala Leu Thr
        195                 200                 205

Val Glu Gly Tyr Gln Ser Ser Gly Ser Ala Asn Val Tyr Ser Asn Thr
    210                 215                 220

Leu Thr Ile Gly Gly Gln
225                 230

<210> SEQ ID NO 60
<211> LENGTH: 217
<212> TYPE: PRT
<213> ORGANISM: P. multivesiculatum

<400> SEQUENCE: 60

Glu Lys Val Ile Cys Leu Leu Ile Ala Leu Phe Gly Leu Ile Glu Ala
1               5                   10                  15

Gln Thr Phe Tyr Asn Asn Ala Gln Gly Gln Ile Asp Gly Leu Asp Tyr
            20                  25                  30

Glu Leu Trp Lys Asp Thr Gly Thr Thr Ser Met Thr Leu Leu Gly Gly
        35                  40                  45

Gly Lys Phe Ser Cys Ser Trp Ser Asn Ile Asn Asn Cys Leu Phe Arg
    50                  55                  60

Ile Gly Lys Lys Trp Asn Cys Gln Tyr Glu Trp Glu Leu Gly Thr
65                  70                  75                  80

Val Leu Val Asn Tyr Asp Val Asp Tyr Asn Pro Asn Gly Asn Ser Tyr
                85                  90                  95

Leu Cys Ile Tyr Gly Trp Thr Arg Asn Pro Leu Val Glu Tyr Tyr Ile
            100                 105                 110

Val Glu Ser Trp Gly Ser Trp Arg Pro Pro Gly Gly Ser Pro Met Asn
        115                 120                 125

Thr Met Tyr Val Asp Asp Gly Gln Tyr Asp Val Tyr Val Thr Asp Arg
    130                 135                 140

Ile Asn Gln Pro Ser Ile Asp Gly Asn Thr Asn Phe Lys Gln Tyr Trp
145                 150                 155                 160

Ser Val Arg Thr Gln Lys Lys Thr Arg Gly Thr Val His Val Asn His
                165                 170                 175

His Phe Tyr Asn Trp Gln Glu Met Gly Leu Lys Val Gly Lys Val Tyr
            180                 185                 190

Glu Ala Ser Leu Asn Ile Glu Gly Tyr Gln Ser Ala Gly Ser Ala Thr
        195                 200                 205

Val Asn Lys Asn Glu Val Val Gln Thr
    210                 215

<210> SEQ ID NO 61
<211> LENGTH: 175
<212> TYPE: PRT
<213> ORGANISM: P multivesiculatum

<400> SEQUENCE: 61

Met Thr Leu Leu Gly Gly Gly Lys Phe Ser Cys Asn Trp Ser Asn Ile
1               5                   10                  15

Gly Asn Ala Leu Phe Arg Ile Gly Lys Lys Trp Asp Cys Thr Lys Thr
            20                  25                  30
```

```
Trp Gln Gln Leu Gly Thr Ile Ser Val Ala Tyr Asn Val Asp Tyr Arg
            35                  40                  45

Pro Asn Gly Asn Ser Tyr Met Cys Val Tyr Gly Trp Thr Arg Ser Pro
        50                  55                  60

Leu Ile Glu Tyr Tyr Ile Val Asp Ser Trp Gly Ser Trp Arg Pro Pro
65                  70                  75                  80

Gly Ser Asn Ser Met Gly Thr Ile Asn Val Asp Gly Gly Thr Tyr Asp
                85                  90                  95

Ile Tyr Val Thr Asp Arg Ile Asn Gln Pro Ser Ile Asp Gly Thr Thr
            100                 105                 110

Thr Phe Lys Gln Phe Trp Ser Val Arg Thr Gln Lys Lys Thr Ser Gly
        115                 120                 125

Val Ile Ser Val Ser Lys His Phe Glu Ala Trp Thr Ser Lys Gly Leu
130                 135                 140

Asn Leu Gly Leu Met Tyr Glu Ala Ser Leu Thr Ile Glu Gly Tyr Gln
145                 150                 155                 160

Ser Ser Gly Ser Ala Thr Val Asn Gln Asn Asp Val Thr Gly Gly
                165                 170                 175

<210> SEQ ID NO 62
<211> LENGTH: 265
<212> TYPE: PRT
<213> ORGANISM: R. albus

<400> SEQUENCE: 62

Met Arg Asn Asn Phe Lys Met Arg Val Met Ala Gly Val Ala Ala Val
1               5                   10                  15

Ile Cys Leu Ala Gly Val Leu Gly Ser Cys Gly Asn Ser Ser Asp Lys
            20                  25                  30

Asp Ser Ser Ser Lys Lys Ser Ala Asp Ser Ala Lys Ala Asp Ser Asn
        35                  40                  45

Lys Asp Ser Lys Asn Gly Gln Val Phe Thr Lys Asn Ala Arg Gly Thr
    50                  55                  60

Ser Asp Gly Tyr Asp Tyr Glu Leu Trp Lys Asp Lys Gly Asp Thr Glu
65                  70                  75                  80

Met Thr Ile Asn Glu Gly Gly Thr Phe Ser Cys Lys Trp Ser Asn Ile
                85                  90                  95

Asn Asn Ala Leu Phe Arg Arg Gly Lys Lys Phe Asp Cys Thr Lys Thr
            100                 105                 110

Tyr Lys Glu Leu Gly Asn Ile Ser Val Lys Tyr Gly Val Asp Tyr Gln
        115                 120                 125

Pro Asp Gly Asn Ser Tyr Met Cys Val Tyr Gly Trp Thr Ile Asp Pro
    130                 135                 140

Leu Val Glu Phe Tyr Ile Val Glu Ser Trp Gly Ser Trp Arg Pro Pro
145                 150                 155                 160

Gly Ala Ala Glu Ser Leu Gly Thr Val Thr Val Asp Gly Gly Thr Tyr
                165                 170                 175

Asp Ile Tyr Lys Thr Thr Arg Tyr Glu Gln Pro Ser Ile Asp Gly Thr
            180                 185                 190

Lys Thr Phe Asp Gln Tyr Trp Ser Val Arg Gln Asp Lys Pro Thr Gly
        195                 200                 205

Asp Gly Thr Lys Ile Glu Gly Thr Ile Ser Ile Ser Lys His Phe Asp
    210                 215                 220

Ala Trp Glu Gln Val Gly Leu Thr Leu Gly Asn Met Tyr Glu Val Ala
```

```
                225                 230                 235                 240
Leu Asn Ile Glu Gly Tyr Gln Ser Asn Gly Gln Ala Thr Ile Tyr Glu
                    245                 250                 255

Asn Glu Leu Thr Val Asp Gly Asn Tyr
            260                 265
```

<210> SEQ ID NO 63
<211> LENGTH: 226
<212> TYPE: PRT
<213> ORGANISM: Caldicellulosiruptor sp

<400> SEQUENCE: 63

```
Met Cys Val Val Leu Ala Asn Pro Phe Tyr Ala Gln Ala Ala Met Thr
1               5                   10                  15

Phe Thr Ser Asn Ala Thr Gly Thr Tyr Asp Gly Tyr Tyr Tyr Glu Leu
                20                  25                  30

Trp Lys Asp Thr Gly Asn Thr Thr Met Thr Val Asp Thr Gly Gly Arg
            35                  40                  45

Phe Ser Cys Gln Trp Ser Asn Ile Asn Asn Ala Leu Phe Arg Thr Gly
        50                  55                  60

Lys Lys Phe Ser Thr Ala Trp Asn Gln Leu Gly Thr Val Lys Ile Thr
65                  70                  75                  80

Tyr Ser Ala Thr Tyr Asn Pro Asn Gly Asn Ser Tyr Leu Cys Ile Tyr
                85                  90                  95

Gly Trp Ser Arg Asn Pro Leu Val Glu Phe Tyr Ile Val Glu Ser Trp
            100                 105                 110

Gly Ser Trp Arg Pro Pro Gly Ala Thr Ser Leu Gly Thr Val Thr Ile
        115                 120                 125

Asp Gly Ala Thr Tyr Asp Ile Tyr Lys Thr Thr Arg Val Asn Gln Pro
    130                 135                 140

Ser Ile Glu Gly Thr Arg Thr Phe Asp Gln Tyr Trp Ser Val Arg Thr
145                 150                 155                 160

Ser Lys Arg Thr Ser Gly Thr Val Thr Val Thr Asp His Phe Lys Ala
                165                 170                 175

Trp Ala Ala Lys Gly Leu Asn Leu Gly Thr Ile Asp Gln Ile Thr Leu
            180                 185                 190

Cys Val Glu Gly Tyr Gln Ser Ser Gly Ser Ala Asn Ile Thr Gln Asn
        195                 200                 205

Thr Phe Thr Ile Gly Gly Ser Ser Gly Ser Ser Asn Gly Ser Asn
    210                 215                 220

Asn Gly
225
```

<210> SEQ ID NO 64
<211> LENGTH: 232
<212> TYPE: PRT
<213> ORGANISM: D. thermophilum

<400> SEQUENCE: 64

```
Met Phe Leu Lys Lys Leu Ser Lys Leu Leu Leu Val Val Leu Leu Val
1               5                   10                  15

Ala Val Tyr Thr Gln Val Asn Ala Gln Thr Ser Ile Thr Leu Thr Ser
                20                  25                  30

Asn Ala Ser Gly Thr Phe Asp Gly Tyr Tyr Tyr Glu Leu Trp Lys Asp
            35                  40                  45

Thr Gly Asn Thr Thr Met Thr Val Tyr Thr Gln Gly Arg Phe Ser Cys
```

```
              50                  55                  60
Gln Trp Ser Asn Ile Asn Asn Ala Leu Phe Arg Thr Gly Lys Lys Tyr
 65                  70                  75                  80

Asn Gln Asn Trp Gln Ser Leu Gly Thr Ile Arg Ile Thr Tyr Ser Ala
                 85                  90                  95

Thr Tyr Asn Pro Asn Gly Asn Ser Tyr Leu Cys Ile Tyr Gly Trp Ser
                100                 105                 110

Thr Asn Pro Leu Val Glu Phe Tyr Ile Val Glu Ser Gly Asn Trp
            115                 120                 125

Arg Pro Pro Gly Ala Thr Ser Leu Gly Gln Val Thr Ile Asp Gly Gly
130                 135                 140

Thr Tyr Asp Ile Tyr Arg Thr Thr Arg Val Asn Gln Pro Ser Ile Val
145                 150                 155                 160

Gly Thr Ala Thr Phe Asp Gln Tyr Trp Ser Val Arg Thr Ser Lys Arg
                165                 170                 175

Thr Ser Gly Thr Val Thr Val Thr Asp His Phe Arg Ala Trp Ala Asn
                180                 185                 190

Arg Gly Leu Asn Leu Gly Thr Ile Asp Gln Ile Thr Leu Cys Val Glu
                195                 200                 205

Gly Tyr Gln Ser Ser Gly Ser Ala Asn Ile Thr Gln Asn Thr Phe Ser
                210                 215                 220

Gln Gly Ser Ser Ser Gly Ser Ser
225                 230

<210> SEQ ID NO 65
<211> LENGTH: 255
<212> TYPE: PRT
<213> ORGANISM: R. flavefaciens

<400> SEQUENCE: 65

Met Lys Leu Ser Lys Ile Lys Lys Val Leu Ser Gly Thr Val Ser Ala
  1               5                  10                  15

Leu Met Ile Ala Ser Ala Ala Pro Val Val Ala Ser Ala Ala Asp Gln
                 20                  25                  30

Gln Thr Arg Gly Asn Val Gly Gly Tyr Asp Tyr Glu Met Trp Asn Gln
             35                  40                  45

Asn Gly Gln Gly Gln Ala Ser Met Asn Pro Gly Ala Gly Ser Phe Thr
         50                  55                  60

Cys Ser Trp Ser Asn Ile Glu Asn Phe Leu Ala Arg Met Gly Lys Asn
 65                  70                  75                  80

Tyr Asp Ser Gln Lys Lys Asn Tyr Lys Ala Phe Gly Asn Ile Val Leu
                 85                  90                  95

Thr Tyr Asp Val Glu Tyr Thr Pro Arg Gly Asn Ser Tyr Met Cys Val
                100                 105                 110

Tyr Gly Trp Thr Arg Asn Pro Leu Met Glu Tyr Tyr Ile Val Glu Gly
            115                 120                 125

Trp Gly Asp Trp Arg Pro Pro Gly Asn Asp Gly Glu Val Lys Gly Thr
130                 135                 140

Val Ser Ala Asn Gly Asn Thr Tyr Asp Ile Arg Lys Thr Met Arg Tyr
145                 150                 155                 160

Asn Gln Pro Ser Leu Asp Gly Thr Ala Thr Phe Pro Gln Tyr Trp Ser
            165                 170                 175

Val Arg Gln Thr Ser Gly Ser Ala Asn Asn Gln Thr Asn Tyr Met Lys
            180                 185                 190
```

-continued

Gly Thr Ile Asp Val Thr Lys His Phe Asp Ala Trp Ser Ala Ala Gly
            195                 200                 205

Leu Asp Met Ser Gly Thr Leu Tyr Glu Val Ser Leu Asn Ile Glu Gly
    210                 215                 220

Tyr Arg Ser Asn Gly Ser Ala Asn Val Lys Ser Val Ser Val Thr Gln
225                 230                 235                 240

Gly Gly Ser Ser Asp Asn Gly Gly Gln Gln Gln Asn Asn Asp Trp
                245                 250                 255

<210> SEQ ID NO 66
<211> LENGTH: 280
<212> TYPE: PRT
<213> ORGANISM: P. stipitis

<400> SEQUENCE: 66

Met Thr Val Tyr Lys Arg Lys Ser Arg Val Leu Ile Ala Val Val Thr
1               5                   10                  15

Leu Leu His Val Leu Ser His Ala Pro Thr Lys Met Leu Thr Thr Asp
            20                  25                  30

Val Leu Leu Thr Arg Cys Met His Leu Cys His Phe Arg Thr Ser Asp
        35                  40                  45

Ser Val Tyr Thr Asn Glu Thr Ser Glu Glu Arg Ser Met Ser Asp Arg
    50                  55                  60

Leu Asn Ile Thr Arg Val Met Ser Tyr Asp Arg Trp Thr Asp Leu Val
65                  70                  75                  80

Gly Glu Leu Glu Val Arg Glu Leu Lys His Val Met Ser His Arg Thr
                85                  90                  95

Tyr Ser Leu Cys Asp Leu Ser Cys Ser Thr Val Leu Asp Ser Asn Ser
            100                 105                 110

Met Phe Ser Leu Gly Lys Gly Trp Gln Ala Ile Ser Ser Arg Gln Gly
        115                 120                 125

Val Gly Ala Thr Val Tyr Gly Trp Thr Arg Ser Pro Leu Leu Ile Glu
    130                 135                 140

Tyr Tyr Val Val Asp Ser Trp Gly Ser Tyr His Pro Ser Asn Thr Ile
145                 150                 155                 160

Thr Gly Thr Phe Val Thr Val Lys Cys Asp Gly Gly Thr Tyr Asp Ile
                165                 170                 175

Tyr Thr Ala Val Arg Val Asn Ala Pro Ser Ile Glu Gly Thr Thr Phe
            180                 185                 190

Thr Gln Tyr Trp Ser Val Arg Gln Ser Ala Thr Ile Gln Leu Ala Val
        195                 200                 205

Ile Lys Pro Leu Thr Leu Gln Asn Ala Thr Ile Thr Phe Thr Phe Ser
    210                 215                 220

Asn His Phe Asp Ala Trp Lys Thr Met Thr Leu Glu Ala Thr His Ser
225                 230                 235                 240

Thr Glu Gly Tyr Phe Ser Ser Gly Ile Thr Tyr Glu Gln Pro His Gln
                245                 250                 255

Pro His Arg Asn Thr Trp Ala Thr Ser Leu Thr Ser Gln Thr Lys His
            260                 265                 270

Thr Ala Arg Ser Leu Pro Ile Asn
        275                 280